(12) United States Patent
Busfield et al.

(10) Patent No.: US 12,065,487 B2
(45) Date of Patent: Aug. 20, 2024

(54) ANTIGEN-BINDING MOLECULES AND USES THEREOF

(71) Applicant: Scout Bio, Inc., Philadelphia, PA (US)

(72) Inventors: Samantha J. Busfield, Victoria (AU); Matthew J. Wilson, Philadelphia, PA (US)

(73) Assignee: Scout Bio, Inc., Philadelphia, PA (US)

( * ) Notice: Subject to any disclaimer, the term of this patent is extended or adjusted under 35 U.S.C. 154(b) by 0 days.

(21) Appl. No.: 18/339,094

(22) Filed: Jun. 21, 2023

(65) Prior Publication Data

US 2023/0365670 A1    Nov. 16, 2023

Related U.S. Application Data

(63) Continuation of application No. PCT/US2022/075788, filed on Aug. 31, 2022.

(60) Provisional application No. 63/239,054, filed on Aug. 31, 2021.

(51) Int. Cl.
| | |
|---|---|
| *C07K 16/22* | (2006.01) |
| *A61P 25/00* | (2006.01) |
| *C12N 15/86* | (2006.01) |

(52) U.S. Cl.
CPC .............. *C07K 16/22* (2013.01); *A61P 25/00* (2018.01); *C12N 15/86* (2013.01); *C07K 2317/565* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,797,368 | A | 1/1989 | Carter et al. |
| 5,139,941 | A | 8/1992 | Muzyczka et al. |
| 5,478,745 | A | 12/1995 | Samulski et al. |
| 5,741,683 | A | 4/1998 | Zhou et al. |
| 5,892,019 | A | 4/1999 | Schlom et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,342,390 | B1 | 1/2002 | Wiener et al. |
| 6,491,907 | B1 | 12/2002 | Rabinowitz et al. |
| 6,660,514 | B1 | 12/2003 | Zolotukhin et al. |
| 6,821,511 | B2 | 11/2004 | Kotin et al. |
| 6,951,753 | B2 | 10/2005 | Shenk et al. |
| 7,094,604 | B2 | 8/2006 | Snyder et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 2003/0042397 | A1 | 3/2003 | Tatsuki et al. |
| 2007/0036760 | A1 | 2/2007 | Wilson et al. |
| 2009/0197338 | A1 | 8/2009 | Vandenberghe et al. |
| 2018/0155415 | A1 | 6/2018 | Pavone |
| 2023/0110287 | A1 | 4/2023 | Busfield |

FOREIGN PATENT DOCUMENTS

| | | |
|---|---|---|
| EP | 1310571 A2 | 5/2003 |
| WO | WO-03042397 A2 | 5/2003 |
| WO | WO-2005033321 A2 | 4/2005 |
| WO | WO-2006110689 A2 | 10/2006 |
| WO | WO-2006131951 A2 | 12/2006 |
| WO | WO-2011126808 A2 | 10/2011 |
| WO | WO-2012153121 A1 | 11/2012 |
| WO | WO-2012153122 A1 | 11/2012 |
| WO | WO-2012153123 A1 | 11/2012 |
| WO | WO-2012153126 A1 | 11/2012 |
| WO | WO-2013034900 A1 | 3/2013 |
| WO | WO-2013049493 A1 | 4/2013 |
| WO | WO-2017040524 A1 | 3/2017 |
| WO | 2021176362 A1 | 9/2021 |
| WO | 2022087153 A1 | 4/2022 |
| WO | 2023034880 A2 | 3/2023 |

OTHER PUBLICATIONS

International Preliminary Report on Patentability received for International Application No. PCT/IB2021/051746, issued Sep. 6, 2022, 6 pages.
International Search Report and Written Opinion for International Application No. PCT/IB2021/051746, mailed Apr. 30, 2021, 25 pages.
Supplementary European Search Report for EP 21 76 5118.1, dated Oct. 25, 2023, 7 pages.
Altschul, S. F., et al., "Gapped BLAST and PSI-BLAST: a new generation of protein database search programs", Nucleic Acids Res, Sep. 1, 1997; 25(17): 3389-402.
Büning et al. "Recent developments in adeno-associated virus vector technology", J Gene Med Jul. 2008; 10(7): 717-33.
Cattaneo, A., "Tanezumab, a recombinant humanized mAb against nerve growth factor for the treatment of acute and chronic pain", Curr Opin Mol Ther, Feb. 2010; 12(1): 94-106.
Chothia, C. et al., "Canonical Structures for the Hypervariable Regions of Immunoglobins", Journal of Molecular Biology, Aug. 1987, vol. 196, No. 4, pp. 901-917.
Enomoto et al., "Anti-nerve growth factor monoclonal antibodies for the control of pain in dogs and cats", Vet Rec, Jan. 5, 2019; 184(1): 23. Epub Oct. 27, 2018, 14 pages.
Fisher et al., "Transduction with recombinant adeno-associated virus for gene therapy is limited by leading-strand synthesis," J Virol, Jan. 1996; 70(1): 520-32.
Gribskov, M, and Burgess, RR, "Sigma factors from *E. coli*, B. subtilis, phage SP01, and phage T4 are homologous proteins," Nucleic Acids Res, Aug. 26, 1986; 14(16): 6745-63.
Grieger et al., "Adeno-associated virus as a gene therapy vector: vector development, production and clinical applications", Adv Biochem Eng Biotechnol, 2005; 99: 119-45.

(Continued)

*Primary Examiner* — Marianne P Allen
(74) *Attorney, Agent, or Firm* — COOLEY LLP

(57) ABSTRACT

The present disclosure relates to an antigen-binding molecule that specifically binds to nerve growth factor (NGF) and uses thereof.

4 Claims, 7 Drawing Sheets

Specification includes a Sequence Listing.

(56) References Cited

OTHER PUBLICATIONS

Im et al., "The AAV origin binding protein Rep68 is an ATP-dependent site-specific endonuclease with DNA helicase activity", Cell, May 4, 1990; 61(3): 447-57.
Miyatake et al., "Transcriptional targeting of herpes simplex virus for cell-specific replication", J Virol, Jul. 1997; 71(7): 5124-32.
Pereira et al., "The adeno-associated virus (AAV) Rep protein acts as both a repressor and an activator to regulate AAV transcription during a productive infection", J Virol, Feb. 1997; 71(2): 1079-88.
Sandig et al., "HBV-derived promoters direct liver-specific expression of an adenovirally transduced LDL receptor gene", Gene Ther, Nov. 1996; 3(11): 1002-9.
Smith, T.F. and Waterman, M.S., "Comparison of biosequences," Advances in Applied Mathematics 2(4), Dec. 1981, pp. 482-489.
Zhang et al., "Adenovirus-adeno-associated virus hybrid for large-scale recombinant adeno-associated virus production", Hum Gene Ther, Sep. 2009; 20(9): 922-9.
Zhang et al., "PKSolver: An add-in program for pharmacokinetic and pharmacodynamic data analysis in Microsoft Excel", Comput Methods Programs Biomed, Sep. 2010; 99(3): 306-14. Epub Feb. 21, 2010.

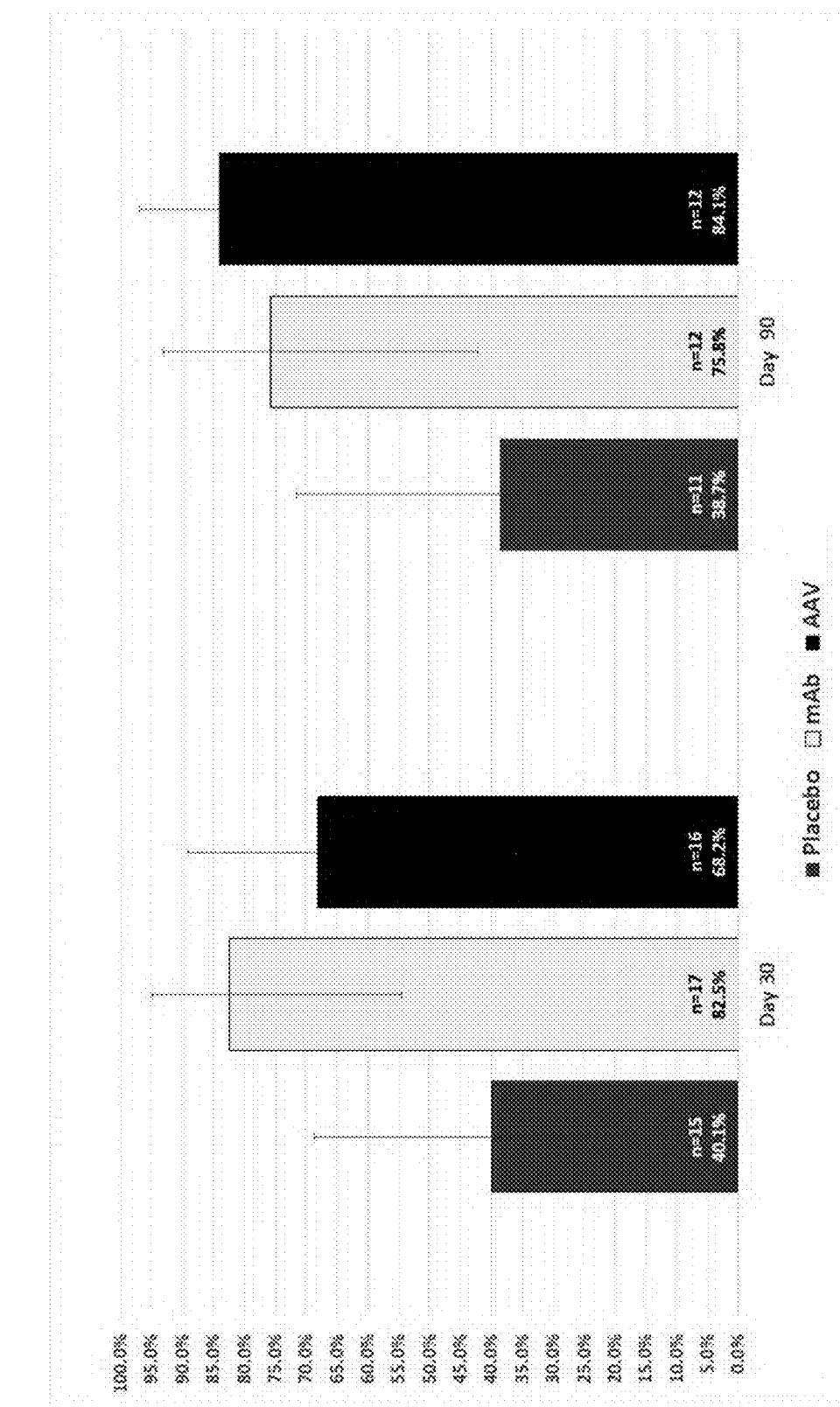

US 12,065,487 B2

ANTIGEN-BINDING MOLECULES AND USES THEREOF

RELATED APPLICATIONS

This application is a continuation of International Application No. PCT/US2022/075788, filed Aug. 31, 2022, which claims priority to, and the benefit of, U.S. Provisional Patent Application No. 63/239,054, filed Aug. 31, 2021, each of which is hereby incorporated by reference in their entirety.

STATEMENT REGARDING SEQUENCE LISTING

The Sequence Listing XML associated with this application is provided in XML file format and is hereby incorporated by reference into the specification. The name of the XML file containing the Sequence Listing XML is SCTB_013_01US_SeqList_ST26.xml. The XML file is 133,783 bytes, and created on Jun. 20, 2023, and is being submitted electronically via USPTO Patent Center.

FIELD OF INVENTION

The present disclosure relates generally to antigen-binding molecules. In particular, the invention relates to antigen-binding molecules that specifically bind to nerve growth factor (NGF) and uses thereof for the treatment of conditions associated with abnormal NGF expression and/or activity, such as pain.

BACKGROUND

All references, including any patent or patent application cited in this specification are hereby incorporated by reference to enable full understanding of the invention. Nevertheless, such references are not to be read as constituting an admission that any of these documents forms part of the common general knowledge in the art, in Australia or in any other country.

Pain, including chronic pain, can be a debilitating condition with far reaching social and economic consequences. Whilst a plethora of analgesic compounds have been prescribed for the treatment or prevention of pain in both humans and non-human animals, examples of which include local and general anaesthetics, opioid analgesics, α2 agonists, non-steroidal anti-inflammatory drugs (NSAIDs) and steroids, their efficacy can vary. Moreover, current analgesics typically require frequent administration over extended periods of time, which contributes, at least in part, to some of the adverse side effects associated with the long term use, including addiction and reduced efficacy.

As noted by Enomoto et al. (2019, *Veterinary Record;* 184(1):23), current pharmacological treatment of pain largely centres around non-steroidal anti-inflammatory drugs (NSAIDs) to relieve pain and promote functional improvement. Globally, several NSAIDs are approved for use in dogs, but only two NSAIDs are approved for use long-term in cats and only in certain countries. Despite their widespread use and obvious benefit in many cases, NSAIDs are not always sufficiently effective when used as monotherapy. Additionally, Enomoto et al. note there are safety and tolerability concerns with their use in both dogs and cats. Beyond cyclooxygenase-inhibiting NSAIDs and the recently approved piprant NSAID, a prostaglandin receptor antagonist, grapiprant, treatment options for the control of pain are very limited. Evidence for efficacy of so-called adjunctive analgesics is also limited. While the authors noted there are few proven non-drug therapies and none has been shown to provide rapid pain relief. This includes pain associated with inflammatory conditions such as osteoarthritis, which remains a challenging clinical entity to treat and is one of the most common reasons for euthanasia in dogs. Therefore, there remains an urgent need for improved analgesics that are effective for both human and veterinary applications, yet also avoid or at least partly alleviate some of the aforementioned problems associated with existing analgesics.

Nerve growth factor (NGF) is a secreted polypeptide and member of the neurotrophin family that is involved in a number of different signalling pathways. For example, NGF has been shown to promote the survival and differentiation of sensory and sympathetic neurons via two membrane bound receptors—p75, a low affinity NGF receptor, and TrkA, a transmembrane tyrosine kinase and a high affinity NGF receptor. The binding of NGF to TrkA or p75 results in an upregulation of neuropeptides in sensory neurons, which typically results in pain perception, or nociception.

NGF antagonists have been used to treat pain and pain sensitivity in humans, dogs and cats. For example, Cattaneo (2010, *Curr. Op. Mol. Ther.* 12(1):94-106) and WO 2006/131951 both describe the use of a humanised form of the rat alphaD11 (αD11) monoclonal antibody, which retains binding specificity to mouse NGF, but also binds to the human and rat forms of NGF. The primary rationale for humanising a donor antibody such as the rat αD11 monoclonal antibody is to minimise the production of neutralising antibodies that would otherwise result from a human anti-rat antibody response against rodent-derived antibodies following administration to a human subject in the course of, for example, antibody therapy. In Cattaneo (2010) and WO 2006/131951, the CDR regions of the rat-derived αD11 monoclonal antibody were grafted onto the framework regions derived from human immunoglobulin sequences, where the human framework sequences were selected for closest sequence identity to the corresponding framework regions of the rat αD11 antibody. Whilst CDR grafting removes FR sequences that would otherwise be foreign to and raise an immune response against the immunoglobulin, it is frequently associated with a loss of binding specificity and selectivity to the target antigen. The loss of binding specificity and selectivity is typically remedied by back-mutating one or more amino acid residues across the target species-derived FR sequences; that is, by replacing one or more amino acid residues across the modified framework regions of the target species with the corresponding residue from the same position in the framework region(s) of the donor antibody. However, whilst this can rescue binding specificity and selectivity, the introduction of amino acid residues within the framework regions from the donor antibody likely introduces an amino acid residue that would be foreign to the target species; that is, to the species to which the modified antibody is to be administered. The method described in WO 2012/153121 seeks to minimise the problem(s) associated with back-mutating by comparing the amino acid residues across the framework regions of a donor anti-NGF antibody (such as the rat-derived αD11 monoclonal antibody) to the corresponding framework region sequences of one or more antibodies from a target species (e.g., canine) and substituting only those residues across the framework regions that are identified as being foreign at a corresponding position having regard to the framework regions from the target species, such that the modified antibody no longer contains any amino acid residue in its framework regions that would be foreign to the target species.

However, whilst modifying the framework regions of an immunoglobulin molecule for compatibility with the target species advantageously minimises the likelihood of an immunogenic response being generated in the target species to which the modified molecule is administered, the presence of foreign epitopes remain where the CDR sequences are derived from a species other than the target species. The presence of foreign epitopes within the CDR sequences can contribute to anti-drug-antibody responses following administration, in particular where multi-dose therapy is required. Thus, there remains an urgent need for improved anti-NGF binding molecules that can be used in therapy, including for the treatment and prevention of pain in human and non-human animals, which overcome or at least partly alleviate one or more of the above-mentioned difficulties associated with existing treatment modalities.

SUMMARY

The present disclosure is predicated, at least in part, on the inventors' surprising finding that an amino acid substitution at a position corresponding to position 14 of the heavy chain CDR2 sequence of the rat αD11 anti-NGF binding molecule (SEQ ID NO:8; as previously described in WO 2006/131951) unexpectedly and markedly reduces the anti-drug-antibody response to the modified anti-NGF binding molecule when administered to a species other than rat, whilst advantageously preserving NGF-binding activity. The resultant anti-NGF binding molecule also showed clinical efficacy 60 days after dosing, suggesting the interval between doses could advantageously be not less than 60 days and could be longer, perhaps 90 days or even 120 days between doses.

Thus, in an aspect disclosed herein, there is provided an antigen-binding molecule that specifically binds to nerve growth factor (NGF), wherein the antigen-binding molecule comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO: 1, a VH CDR2 comprising the amino acid sequence of SEQ ID NO: 2 and a VH CDR3 comprising the amino acid sequence of SEQ ID NO: 3; and wherein the VL comprises a complementarity determining region 1 (VL CDR1) comprising the amino acid sequence of SEQ ID NO: 4, a VL CDR2 comprising the amino acid sequence of SEQ ID NO: 5, and a VL CDR3 comprising the amino acid sequence of SEQ ID NO: 6:

```
VH CDR1
                                   (SEQ ID NO: 1)
GFSLTNNNVN

VH CDR2
                                   (SEQ ID NO: 2)
GVWAGGATDYNSAVKS

VH CDR3
                                   (SEQ ID NO: 3)
DGGYSSSTLYAMDA

VL CDR1
                                   (SEQ ID NO: 4)
RASEDIYNALA
```

-continued

```
VL CDR2
                                   (SEQ ID NO: 5)
NTDTLHT

VL CDR3
                                   (SEQ ID NO: 6)
QHYFHYPRT
```

In an embodiment, the antigen-binding molecule comprises:

(a) a VH framework region 1 (FR1) comprising an amino acid sequence having at least 80% sequence identity to an amino acid sequence selected from the group consisting of SEQ ID NOs: 13, 36, 40, 44, 48, 52 and 72-127;
(b) a VH FR2 comprising an amino acid sequence having at least 80% sequence identity to an amino acid sequence selected from the group consisting of SEQ ID NOs: 14, 37, 41, 45, 49 and 53;
(c) a VH FR3 comprising an amino acid sequence having at least 80% sequence identity to an amino acid sequence selected from the group consisting of SEQ ID NOs: 15, 38, 42, 46, 50 and 54;
(d) a VH FR4 comprising an amino acid sequence having at least 80% sequence identity to an amino acid sequence selected from the group consisting of SEQ ID NOs: 16, 39, 43, 47, 51 and 55;
(e) a VL FR1 comprising an amino acid sequence having at least 80% sequence identity to an amino acid sequence selected from the group consisting of SEQ ID NOs: 17, 56, 60, 64, 68 and 129;
(f) a VL FR2 comprising an amino acid sequence having at least 80% sequence identity to an amino acid sequence selected from the group consisting of SEQ ID NOs: 18, 57, 61, 65 and 69;
(g) a VL FR3 comprising an amino acid sequence having at least 80% sequence identity to an amino acid sequence selected from the group consisting of SEQ ID NOs: 19, 58, 62, 66 and 70; and
(h) a VL FR4 comprising an amino acid sequence having at least 80% sequence identity to an amino acid sequence selected from the group consisting of SEQ ID NOs: 20, 59, 63, 67 and 71.

In an embodiment, (a) the VH comprises an amino acid sequence having at least 80% sequence identity to an amino acid sequence selected from the group consisting of SEQ ID NO: 12 and SEQ ID NOs: 27 to 31, and
(b) the VL comprises an amino acid sequence having at least 80% sequence identity to an amino acid sequence selected from the group consisting of SEQ ID NO: 10, 128 and SEQ ID NOs: 32 to 35.

In an embodiment, the antigen-binding molecule comprises:

(a) a VH FR1 comprising an amino acid sequence having at least 80% sequence identity to a VH FR1 amino acid sequence selected from the group consisting of SEQ ID NO: 13 and SEQ ID NOs:72-127,
(b) a VH FR2 comprising an amino acid sequence having at least 80% sequence identity to a VHFR2 amino acid of SEQ ID NO: 14,
(c) a VH FR3 comprising an amino acid sequence having at least 80% sequence identity to a VHFR3 amino acid sequence of SEQ ID NO: 15,
(d) a VH FR4 comprising an amino acid sequence having at least 80% sequence identity to a VHFR4 amino acid sequence of SEQ ID NO: 16, (e) a VL FR1 comprising an amino acid sequence having at least 80% sequence identity to a VLFR1 amino acid sequence of SEQ ID NO:17 or SEQ ID NO:129, (f) a VL FR2 comprising an amino acid sequence having at least 80% sequence identity to a VLFR2 amino acid sequence of SEQ ID NO:18, (g) a VL FR3 comprising an amino acid sequence having at least 80% sequence identity to a VLFR3 amino acid sequence of SEQ ID NO: 19, and (h) a VL FR4 comprising an amino acid sequence having at least 80% sequence identity to a VHFR4 amino acid sequence of SEQ ID NO: 20.

In an embodiment, the antigen-binding molecule comprises:
(a) the VH comprises an amino acid sequence having at least 80% sequence identity to a VH amino acid sequence of SEQ ID NO: 12, and
(b) the VL comprises an amino acid sequence having at least 80% sequence identity to a VL amino acid sequence of SEQ ID NO: 10 or SEQ ID NO:128.

In an embodiment, the antigen-binding molecule comprises:
(a) the VH comprises an amino acid sequence having at least 80% sequence identity to a VH amino acid sequence of any one of SEQ ID NOs: 27-31, and
(b) the VL comprises an amino acid sequence having at least 80% sequence identity to a VL amino acid sequence of any one of SEQ ID NOs: 32-35.

In an embodiment, the antigen-binding molecule is an antibody or an NGF-binding fragment thereof. Suitable NGF-binding fragments will be familiar to persons skilled in the art, illustrative examples of which include an Fab fragment, an scFab, an Fab', a single chain variable fragment (scFv) and a one-armed antibody. Thus, in an embodiment disclosed herein, the NGF-binding fragment is selected from the group consisting of an Fab fragment, an scFab, an Fab', a single chain variable fragment (scFv) and a one-armed antibody.

In an embodiment, the antigen-binding molecule is a humanized, a caninized, a felinized or an equinized antibody or an NGF-binding fragment thereof.

In another aspect disclosed herein, there is provided an isolated nucleic acid molecule comprising a nucleic acid sequence encoding the antigen-binding molecule as described herein.

Also disclosed herein is an expression construct comprising a nucleic acid sequence encoding the antigen-binding molecule described herein, wherein the nucleic acid sequence is operably linked to one or more regulatory sequences.

The present disclosure also extends to a host cell comprising the expression construct described herein.

The present disclosure also extends to vector comprising a nucleic acid sequence encoding the antigen-binding molecule described herein. Suitable vectors will be familiar to persons skilled in the art. In an embodiment, the vector is an AAV vector.

The present disclosure also extends to a pharmaceutical composition comprising the antigen-binding molecule described herein, and a pharmaceutically acceptable carrier.

In another aspect disclosed herein, there is provided a method of treating or preventing a condition associated with increased expression and/or increased activity of NGF, the method comprising administering to a subject in need thereof the antigen-binding molecule, the vector, or the pharmaceutical composition, as herein described.

Conditions associated with increased expression and/or increased activity of NGF will be familiar to persons skilled in the art, illustrative examples of which include pain, arthritis and cancer.

Illustrative examples of pain associated with increased expression and/or increased activity of NGF include neuropathic, inflammatory, pruritic, pen-operative, post-operative and post-surgical pain.

Illustrative examples of arthritis associated with increased expression and/or increased activity of NGF include immune mediated polyarthritis, rheumatoid arthritis and osteoarthritis.

In another aspect disclosed herein, there is provided a method of treating or preventing a tumour induced to proliferate by NGF and conditions associated therewith, the method comprising administering to a subject in need thereof the antigen-binding molecule, the vector, or the pharmaceutical composition, as herein described. An illustrative example of a tumour induced to proliferate by NGF and conditions associated therewith is osteosarcoma.

Also disclosed herein is a kit comprising the antigen-binding molecule, the vector, or the pharmaceutical composition, as herein described.

The present disclosure also extends to use of the antigen-binding molecule, or the vector, as herein described, in the manufacture of a medicament for treating or preventing a condition associated with increased expression and/or increased activity of NGF in a subject in need thereof.

The present disclosure also extends to use of the antigen-binding molecule, or the vector, as herein described, in the manufacture of a medicament for treating or preventing a tumour induced to proliferate by NGF and conditions associated therewith in a subject in need thereof.

The present disclosure also extends to the antigen-binding molecule, the vector, or the pharmaceutical composition, as herein described, for use in the treatment or prevention of a condition associated with increased expression and/or increased activity of NGF in a subject in need thereof.

The present disclosure also extends to the antigen-binding molecule, the vector, or the pharmaceutical composition, as herein described, for use in the treatment or prevention of a tumour induced to proliferate by NGF and conditions associated therewith in a subject in need thereof.

BRIEF DESCRIPTION OF DRAWINGS

Embodiments of the present invention are hereafter described, by way of non-limiting example only, with reference to the accompanying drawings in which.

DETAILED DESCRIPTION

Figure 1:
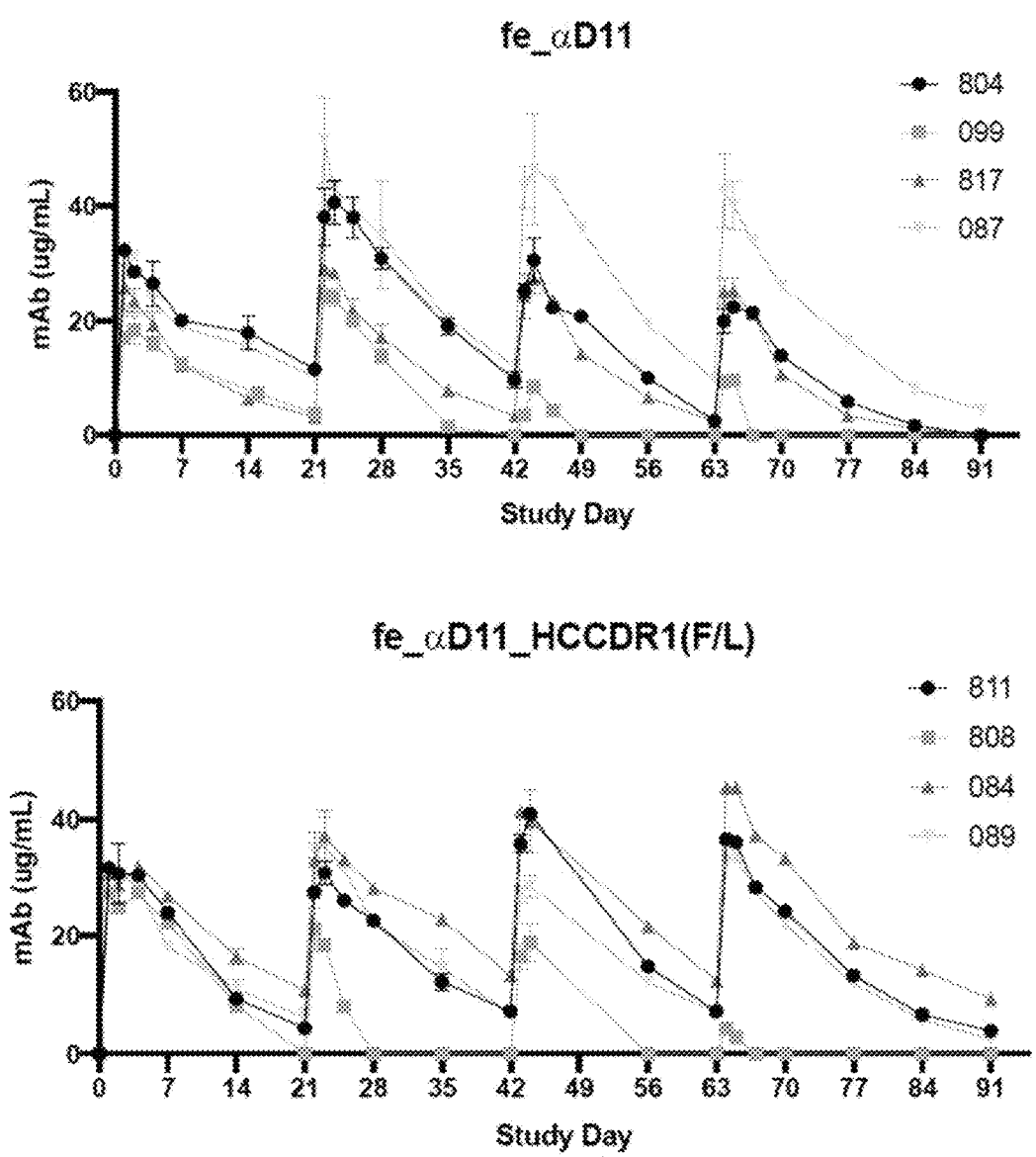
FIG. 1 shows the pharmacokinetic profile of the felinized anti-NGF monoclonal antibodies fel_αD11, fel_αD11_HCCDR1(F/L) and fel_αD11_HCCDR2(L/V) in cats following subcutaneous administration. Antibodies were administered subcutaneously twice to each of four cats at 2 mg/kg body weight on Days 0, 21, 42 and 63. The serum concentration of the felinized anti-NGF antibodies was determined at the times indicated using a quantitative NGF-binding ELISA, as described elsewhere herein. The data shown are mean+/−SD.
Figure 1:
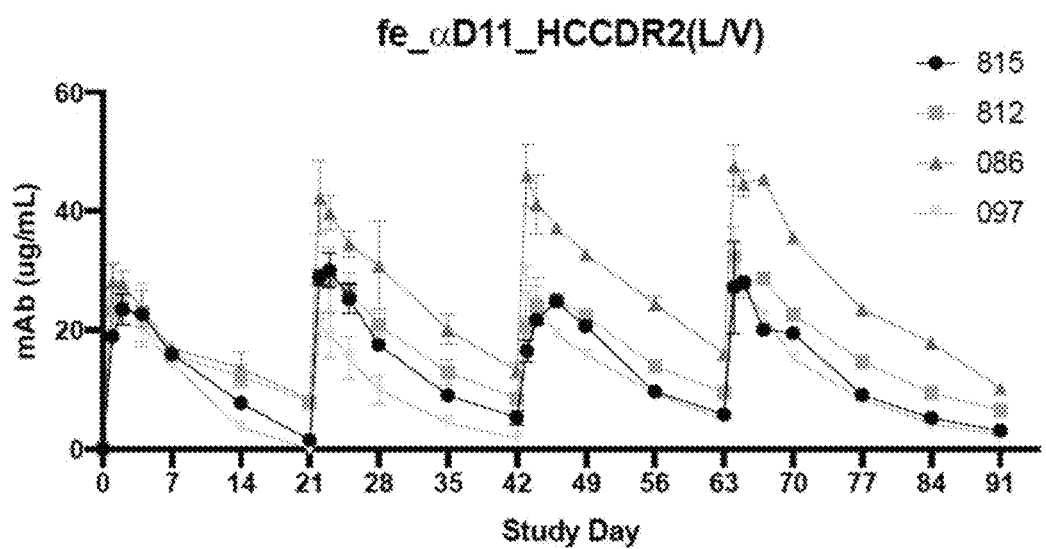

As described elsewhere herein, the present disclosure is predicated, at least in part, on the inventors' surprising finding that an amino acid substitution at a position corresponding to position 14 of the heavy chain CDR2 sequence of the rat αD11 anti-NGF binding molecule (SEQ ID NO:8; as previously described in WO 2006/131951) unexpectedly and markedly reduces the anti-drug-antibody response to the modified anti-NGF binding molecule when administered to a species other than rat, whilst advantageously preserving NGF-binding activity.

Thus, disclosed herein is an antigen-binding molecule that is capable of binding specifically to nerve growth factor (NGF), wherein the antigen-binding molecule comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO: 1, a VH CDR2 comprising the amino acid sequence of SEQ ID NO: 2 and a VH CDR3 comprising the amino acid sequence of SEQ ID NO: 3; and wherein the VL comprises a complementarity determining region 1 (VL CDR1) comprising the amino acid sequence of SEQ ID NO: 4, a VL CDR2 comprising the amino acid sequence of SEQ ID NO: 5, and a VL CDR3 comprising the amino acid sequence of SEQ ID NO: 6:

VH CDR1
    (SEQ ID NO: 1)
GFSLTNNNVN

VH CDR2
    (SEQ ID NO: 2)
GVWAGGATDYNSAVKS

VH CDR3
    (SEQ ID NO: 3)
DGGYSSSTLYAMDA

VL CDR1
    (SEQ ID NO: 4)
RASEDIYNALA

VL CDR2
    (SEQ ID NO: 5)
NTDTLHT

VL CDR3
    (SEQ ID NO: 6)
QHYFHYPRT

A "conservative amino acid substitution" is to be understood as meaning a substitution in which the amino acid residue is replaced with an amino acid residue having a similar side chain. Families of amino acid residues having similar side chains have been defined in the art, which can be generally sub-classified as shown in the table "Amino Acid Classification", below:

| AMINO ACID SUB-CLASSIFICATION | |
|---|---|
| Sub-classes | Amino acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity.

Conservative substitutions are also shown in the table below (EXEMPLARY AND PREFERRED AMINO ACID SUBSTITUTIONS). Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants can be screened for their ability to bind specifically to NGF using methods known to persons skilled in the art, including those methods described elsewhere herein.

Exemplary and Preferred Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

By "antigen-binding molecule" is meant a molecule that has binding affinity for a target antigen. It will be understood that this term extends to immunoglobulins, immunoglobulin fragments and non-immunoglobulin-derived protein frameworks that exhibit antigen-binding activity. Illustrative examples of suitable antigen-binding molecules include antibodies and antigen-binding fragments thereof. Preferably, the antigen-binding molecule binds specifically to NGF so as to neutralise, or substantially neutralise, its activity. The term "neutralise" is understood to mean that the antigen-binding molecule will bind to NGF and inhibit, reduce, abrogate, block or otherwise prevent the ability of the NGF molecule to bind to its native receptor (e.g., p75 or TrkA). In some embodiments, the antigen-binding molecule will completely neutralise the activity of NGF (in vivo or in vitro) such that there is no or negligible NGF activity when compared to the absence of the antigen-binding molecule. In other embodiments, the antigen-binding molecule will partially neutralise the activity of NGF (in vivo or in vitro) such that there is less NGF activity when compared to the absence of the antigen-binding molecule.

In an embodiment, the antigen-binding molecule, as described herein, is conjugated to another molecule or moiety, including functional moieties (e.g., toxins), detectable moieties (e.g., fluorescent molecules, radioisotopes), small molecule drugs and polypeptides.

The term "antibody", as used herein, is understood to mean any antigen-binding molecule or molecular complex comprising at least one complementarity determining region (CDR) that binds specifically to, or interacts specifically with, the target antigen. The term "antibody" includes full-length immunoglobulin molecules comprising two heavy (H) chains and two light (L) chains inter-connected by disulfide bonds, as well as multimers thereof (e.g., IgM). Each heavy chain comprises a heavy chain variable region (which may be abbreviated as HCVR, VH or $V_H$) and a heavy chain constant region. The heavy chain constant region typically comprises three domains-$C_H1$, $C_H2$ and $C_H3$. Each light chain comprises a light chain variable region (which may be abbreviated as LCVR, VL, VK, $V_K$ or $V_L$) and a light chain constant region. The light chain constant region will typically comprise one domain ($C_L1$). The $V_H$ and $V_L$ regions can be further subdivided into regions of hypervariability, termed complementarity determining regions (CDRs), interspersed with regions that are more conserved, also referred to as framework regions (FR). Each $V_H$ and $V_L$ typically comprises three CDRs and four FRs, arranged from amino-terminus to carboxy-terminus in the following order: FR1, CDR1, FR2, CDR2, FR3, CDR3, FR4. In some embodiments, the FRs of the antigen-binding molecules described herein may be identical to the FR of germline sequences of the target species (i.e., the species to which the antigen-binding molecules or antigen-binding fragments thereof, as described herein, will be administered). In some embodiments, the FR may be naturally or artificially modified. Whilst it is generally desirable that each of the FR sequences are identical to FR sequences derived from immunoglobulin molecules of the target species, including to minimize an immune response being raised against the binding molecule upon administration to a subject of the target species, in some embodiments, the antigen-binding molecule, or antigen-binding fragment thereof, may comprise one or more amino acid residues across one or more of its FR sequences that would be foreign at a corresponding position in one or more FR from the target species. Preferably, where the antigen-binding molecule, or antigen-binding fragment thereof, comprises one or more amino acid residues across one or more of its FR sequences that would be foreign at a corresponding position in the target species, that "foreign" amino acid residue will not (i) adversely impact the binding specificity of the antigen-binding molecule or antigen-binding fragment thereof to NGF, including native NGF and/or (ii) cause an immune response to be raised against the antigen-binding molecule or to the antigen-binding fragment thereof when administered to a subject of the target species.

Suitable antibodies include antibodies of any class, such as IgG, IgA, or IgM (including sub-classes thereof). There are five major classes of immunoglobulins: IgA, IgD, IgE, IgG, and IgM, characterised by heavy-chain constant regions α, δ, ε, γ, and μ, respectively. Several antibody classes may be further divided into subclasses (isotypes), e.g., IgG1, IgG2, IgG3, IgG4, IgA1 and IgA2. The subunit structures and three-dimensional configurations of different classes of immunoglobulins will be well known to persons skilled in the art.

As used herein, the term "complementarity determining region" (CDR) refers to the region of an immunoglobulin variable domain that recognizes and binds to the target antigen. Each variable domain may comprises up to three CDR sequences, identified as CDR1, CDR2 and CDR3. The amino acid sequence of each CDR is often defined by Kabat numbering (e.g., about residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health, Bethesda, Md. (1991)) and/or by Chothia numbering (e.g., about residues 26-32 (L1), 50-52 (L2) and 91-96 (L3) of the light chain variable domain and 26-32 (H1), 53-55 (H2) and 96-101 (H3) of the heavy chain variable domain; see Chothia and Lesk *J. Mol. Biol.* 196:901-917 (1987)). As disclosed elsewhere herein, the present inventor has unexpectedly shown that amino acid positions along the CDR sequences of the NGF-binding molecules may be substituted with one or more conservative or non-conservative amino acids whilst retaining the ability to bind specifically to its target antigen, NGF. Hence, the present disclosure extends to functional variants of the NGF-binding molecules disclosed herein. The term "functional variant", as used herein, is to be understood as meaning an NGF-binding molecule comprising the CDR sequences having at least 80% sequence identity to any one of SEQ ID NOs:1-6 and retaining the ability to specifically bind to and neutralise or otherwise inhibit the activity of NGF.

The present disclosure extends to antigen-binding molecules that bind specifically to NGF of any species. In an embodiment, the NGF is selected from the group consisting of human NGF, canine NGF, feline NGF and equine NGF. In an embodiment, the NGF is a human NGF. In another embodiment, the NGF is a canine NGF. In another embodiment, the NGF is a feline NGF. In yet another embodiment, the NGF is an equine NGF. The present disclosure extends to antigen binding molecules that bind specifically to native NGF (i.e., naturally-occurring NGF), as well as to variants thereof. Such variants may include NGF molecules that differ from a naturally-occurring (wild-type) molecule by one or more amino acid substitutions, deletions and/or insertions. Variant NGF molecules of this type may be naturally-occurring or synthetic (e.g., recombinant) forms. It is to be understood, however, that in a preferred embodiment, the antigen-binding molecules described herein bind specifically to a native form of NGF, whether of a human or non-human species The terms "antigen-binding fragment", "antigen-binding portion", "antigen-binding domain", "antigen-binding site" and the like are used interchangeably herein to refer to a part of an antigen-binding molecule that retains the ability to bind to the target antigen; that is, to NGF, including native NGF. These terms include naturally occurring, enzymatically obtainable, synthetic or genetically engineered (recombinant) polypeptides and glycoproteins that specifically bind to NGF to form a complex.

Antigen-binding fragments may be derived, for example, from naturally-derived immunoglobulin molecules using any suitable method known to persons skilled in the art, illustrative examples of which include proteolytic digestion or recombinant genetic engineering techniques involving the manipulation and expression of nucleic acid sequences encoding antibody variable and optionally constant domains. Suitable nucleic acid sequences are known and/or are readily available from, e.g., commercial sources, DNA libraries (including, e.g., phage-antibody libraries), or can be synthesized. The nucleic acid sequences may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of suitable antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, one-armed antibodies, diabodies, triabodies, tetrabodies, minibodies, nanobodies (e.g. monovalent nanobodies, bivalent nanobodies, etc.), and small modular immunopharmaceuticals (SMIPs), are also encompassed by the term "antigen-binding fragment," as used herein.

In an embodiment, an antigen-binding fragment comprises at least one immunoglobulin variable domain. The variable domain may comprise an amino acid sequence of any suitable length or composition and will generally comprise at least one CDR which is adjacent to or in frame with one or more framework sequences. Where the antigen-binding fragment comprises a $V_H$ domain and a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In some embodiments, an antigen-binding fragment may comprise at least one variable domain covalently linked to at least one constant domain. Non-limiting configurations of variable and constant domains that may be found within an antigen-binding fragment include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. In some embodiments, the antigen-binding fragment, as herein described, may comprise a homo-dimer or hetero-dimer (or other multimer) of any of the variable and constant domain configurations listed above in non-covalent association with one another and/or with one or more monomeric $V_H$ or $V_L$ domains (e.g., by disulfide bond(s)). A multispecific antigen-binding molecule will typically comprise at least two different variable domains, wherein each variable domain is capable of specifically binding to a separate antigen or to a different epitope on the same antigen. Any multispecific antigen-binding molecule format, including bispecific antigen-binding molecule formats, may be adapted for use in the context of an antigen-binding fragment of an antibody of the present disclosure using routine techniques available in the art.

The term "variable region" or "variable domain" refers to the domain of an immunoglobulin heavy or light chain that is involved in binding to the target antigen. The variable domains of the heavy chain and light chain ($V_H$ and $V_L$, respectively) of a native immunoglobulin molecule will generally have similar structures, with each domain comprising four conserved framework regions and three hypervariable regions (HVRs). See, e.g., Kindt et al., *Kuby Immunology*, 6th ed., W. H. Freeman and Co., page 91 (2007). A single $V_H$ or $V_L$ domain may be sufficient to confer antigen-binding specificity.

As described elsewhere herein, the amino acid substitutions identified as advantageously reducing the anti-drug-antibody response to the modified anti-NGF binding molecule in a target species other than rat, whilst preserving NGF-binding activity, are within the heavy chain CDR sequences corresponding to the CDR sequences of the rat αD11 anti-NGF binding molecule. The anti-NGF binding molecule described herein may suitably comprise further modifications, such as within its framework and/or constant regions, for compatibility with the target species. As an illustrative example, one or more of the framework regions of the modified anti-NGF binding molecule will suitably comprise amino acid sequences that are native (not foreign) to the target species to which the modified anti-NGF binding molecule is to be administered. It is to be understood that the framework regions of the anti-NGF binding molecule described herein may be modified for compatibility with any target species (other than rat). Such modified binding molecules are often referred to be reference to the species to which they are targeted. For instance, binding molecules comprising modified framework regions for compatibility with feline may be referred to as felinized antigen-binding molecules; binding molecules comprising modified framework regions for compatibility with canine may be referred to as caninized antigen-binding molecules; binding molecules comprising modified framework regions for compatibility with equine may be referred to as equinized antigen-binding molecules; binding molecules comprising modified framework regions for compatibility with human may be referred to as humanized antigen-binding molecules; and so on. Suitable target species will be familiar to persons skilled in the art, illustrative examples of which include any member of the subphylum Chordata including primates (e.g., humans, monkeys and apes, and includes species of monkeys such as from the genus *Macaca* (e.g., cynomolgus monkeys such as *Macaca fascicularis*, and/or rhesus monkeys (*Macaca* mulatta)) and baboon (*Papio ursinus*), as well as marmosets (species from the genus Callithrix), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish.

In an embodiment, the antigen-binding molecule or antigen-binding fragment thereof is humanized, caninized, felinized or equinized.

By "humanized" is meant that the antigen-binding molecule comprises an amino acid sequence that is compatible with humans, such that the amino acid sequence is unlikely to be seen as foreign by the immune system of a human subject. In an embodiment, the humanized antigen-binding molecule comprises one or more immunoglobulin framework regions derived from one or more human immunoglobulin molecules. In some embodiments, all of the framework regions of the humanized antigen-binding molecule will be derived from one or more human immunoglobulin molecules. The humanized antibody may optionally comprise an immunoglobulin heavy chain constant region derived from a human immunoglobulin molecule.

By "caninized" is meant that the antigen-binding molecule comprises an amino acid sequence that is compatible with canine, such that the amino acid sequence is unlikely to be seen as foreign by the immune system of a canine subject. In an embodiment, the caninized antigen-binding molecule comprises one or more immunoglobulin framework regions derived from one or more canine immunoglobulin molecules. In some embodiments, all of the framework regions of the caninized antigen-binding molecule will be derived from one or more canine immunoglobulin molecules. The caninized antibody may optionally comprise an immunoglobulin heavy chain constant region derived from a canine immunoglobulin molecule.

By "felinized" is meant that the antigen-binding molecule comprises an amino acid sequence that is compatible with feline, such that the amino acid sequence is unlikely to be seen as foreign by the immune system of a feline subject. In an embodiment, the felinized antigen-binding molecule comprises one or more immunoglobulin framework regions derived from one or more feline immunoglobulin molecules. In some embodiments, all of the framework regions of the felinized antigen-binding molecule will be derived from one or more feline immunoglobulin molecules. The felinized antibody may optionally comprise an immunoglobulin heavy chain constant region derived from a feline immunoglobulin molecule.

By "equinized" is meant that the antigen-binding molecule comprises an amino acid sequence that is compatible with equine, such that the amino acid sequence is unlikely to be seen as foreign by the immune system of an equine subject. In an embodiment, the equinized antigen-binding molecule comprises one or more immunoglobulin framework regions derived from one or more equine immunoglobulin molecules. In some embodiments, all of the framework regions of the equinized antigen-binding molecule will be derived from one or more equine immunoglobulin molecules. The equinized antibody may optionally comprise an immunoglobulin heavy chain constant region derived from an equine immunoglobulin molecule.

As noted elsewhere herein, the present disclosure extends to antigen-binding molecules that are compatible with species other than human, canine, feline and equine. In this context, the antigen-binding molecules can be referred to as "speciesized", referring to the target species to which the molecule will be administered.

Suitable methods of designing and producing recombinant antibodies or antigen-binding molecules that are compatible with the target species will be familiar to persons skilled in the art, illustrative examples of which are described in Cattaneo (2010; supra), WO 2006/131951, WO 2012/153122, WO 2013/034900, WO 2012/153121 and WO 2012/153123, the contents of which are incorporated herein by reference in their entirety.

The phrase "specifically binds" or "specific binding" refers to a binding reaction between two molecules that is at least two times the background and more typically more than 10 to 100 times background molecular associations under physiological conditions. When using one or more detectable binding agents that are proteins, specific binding is determinative of the presence of the protein, in a heterogeneous population of proteins and other biologics. Thus, under designated immunoassay conditions, the specified antigen-binding molecule binds to a particular antigenic determinant, thereby identifying its presence. Specific binding to an antigenic determinant under such conditions requires an antigen-binding molecule that is selected for its specificity to that determinant. This selection may be achieved by subtracting out antigen-binding molecules that cross-react with other molecules. A variety of immunoassay formats may be used to select antigen-binding molecules (e.g., immunoglobulins) [such that they are specifically immunoreactive with a particular antigen. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Methods of determining binding affinity and specificity are also well known in the art (see, for example, Harlow and Lane, supra); Friefelder, "Physical Biochemistry: Applications to biochemistry and molecular biology" (W.H. Freeman and Co. 1976))

"Affinity" or "binding affinity" refers to the strength of the sum total of non-covalent interactions between a single binding site of a molecule (e.g., an antigen-binding molecule) and its binding partner (e.g., an antigen). Unless indicated otherwise, as used herein, "binding affinity" refers to intrinsic binding affinity which reflects a 1:1 interaction between members of a binding pair e.g., an antigen-binding molecule. The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide.

As used herein, the term "modified antibody" includes synthetic forms of antibodies which are altered such that they are not naturally occurring, e.g., antibodies that comprise at least two heavy chain portions but not two complete heavy chains (such as domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen).

As note elsewhere herein, the anti-NGF binding molecule described herein may suitably comprise further modifications within its framework and/or constant regions, including for compatibility with the target species. As an illustrative example, one or more of the framework regions of the modified anti-NGF binding molecule will suitably comprise amino acid sequences that are native (not foreign) to the target species to which the modified anti-NGF binding molecule is to be administered.

In an embodiment, the antigen-binding molecule comprises a VH framework region 1 (FR1) comprising an amino acid sequence QVQLX$_1$ESGX$_2$X$_3$LVQPX$_4$X$_5$SLRLTCX$_6$AS (SEQ ID NO:74), wherein:
- (a) X$_1$ is selected from the group consisting of valine, methionine and a conservative amino acid substitution of any of the foregoing;
- (b) X$_2$ is selected from the group consisting of glycine, alanine and a conservative amino acid substitution of any of the foregoing;
- (c) X$_3$ is selected from the group consisting of aspartic acid, glutamic acid and a conservative amino acid substitution of any of the foregoing;
- (d) X$_4$ is selected from the group consisting of glycine, serine and a conservative amino acid substitution of any of the foregoing;
- (e) X$_5$ is selected from the group consisting of glycine, glutamic acid and a conservative amino acid substitution of any of the foregoing; and
- (f) X$_6$ is selected from the group consisting of valine, alanine and a conservative amino acid substitution of any of the foregoing.

In an embodiment, the antigen-binding molecule comprises a VH framework region 1 (FR1) comprising an amino acid selected from the group consisting of:

(a) QVQLVESGADLVQPSESLRLTCVAS; (SEQ ID NO: 75)

(b) QVQLVESGGDLVQPSESLRLTCVAS; (SEQ ID NO: 76)

(c) QVQLVESGADLVQPGESLRLTCVAS; (SEQ ID NO: 77)

(d) QVQLVESGADLVQPSGSLRLTCVAS; (SEQ ID NO: 78)

(e) QVQLVESGGDLVQPGESLRLTCVAS; (SEQ ID NO: 79)

(f) QVQLVESGGDLVQPSGSLRLTCVAS; (SEQ ID NO: 80)

(g) QVQLVESGGDLVQPGGSLRLTCVAS; (SEQ ID NO: 72)

(h) QVQLMESGADLVQPSESLRLTCVAS; (SEQ ID NO: 13)

(i) QVQLMESGGDLVQPSESLRLTCVAS; (SEQ ID NO: 81)

(j) QVQLMESGADLVQPGESLRLTCVAS; (SEQ ID NO: 82)

(k) QVQLMESGADLVQPSGSLRLTCVAS; (SEQ ID NO: 83)

(l) QVQLMESGGDLVQPGESLRLTCVAS; (SEQ ID NO: 84)

(m) QVQLMESGGDLVQPSGSLRLTCVAS; (SEQ ID NO: 85)

(n) QVQLMESGGDLVQPGGSLRLTCVAS; (SEQ ID NO: 86)

(o) QVQLVESGADLVQPSESLRLTCAAS; (SEQ ID NO: 87)

(p) QVQLVESGGDLVQPSESLRLTCAAS; (SEQ ID NO: 88)

(q) (SEQ ID NO: 89)
QVQLVESGADLVQPGESLRLTCAAS;

(r) (SEQ ID NO: 90)
QVQLVESGADLVQPSGSLRLTCAAS;

(s) (SEQ ID NO: 91)
QVQLVESGGDLVQPGESLRLTCAAS;

(t) (SEQ ID NO: 92)
QVQLVESGGDLVQPSGSLRLTCAAS;

(u) (SEQ ID NO: 93)
QVQLVESGGDLVQPGGSLRLTCAAS;

(v) (SEQ ID NO: 94)
QVQLMESGADLVQPSESLRLTCAAS;

(w) (SEQ ID NO: 95)
QVQLMESGGDLVQPSESLRLTCAAS;

(x) (SEQ ID NO: 96)
QVQLMESGADLVQPGESLRLTCAAS;

(y) (SEQ ID NO: 97)
QVQLMESGADLVQPSGSLRLTCAAS;

(z) (SEQ ID NO: 98)
QVQLMESGGDLVQPGESLRLTCAAS;

(aa) (SEQ ID NO: 99)
QVQLMESGGDLVQPSGSLRLTCAAS;

(bb) (SEQ ID NO: 100)
QVQLMESGGDLVQPGGSLRLTCAAS;

(cc) (SEQ ID NO: 101)
QVQLVESGAELVQPSESLRLTCVAS;

(dd) (SEQ ID NO: 102)
QVQLVESGGELVQPSESLRLTCVAS;

(ee) (SEQ ID NO: 103)
QVQLVESGAELVQPGESLRLTCVAS;

(gg) (SEQ ID NO: 105)
QVQLVESGGELVQPGESLRLTCVAS;

(hh) (SEQ ID NO: 106)
QVQLVESGGELVQPSGSLRLTCVAS;

(ii) (SEQ ID NO: 107)
QVQLVESGGELVQPGGSLRLTCVAS;

(jj) (SEQ ID NO: 108)
QVQLMESGAELVQPSESLRLTCVAS;

(kk) (SEQ ID NO: 109)
QVQLMESGGELVQPSESLRLTCVAS;

(ll) (SEQ ID NO: 110)
QVQLMESGAELVQPGESLRLTCVAS;

(mm) (SEQ ID NO: 111)
QVQLMESGAELVQPSGSLRLTCVAS;

(nn) (SEQ ID NO: 112)
QVQLMESGGELVQPGESLRLTCVAS;

(oo) (SEQ ID NO: 113)
QVQLMESGGELVQPSGSLRLTCVAS;

(pp) (SEQ ID NO: 114)
QVQLMESGGELVQPGGSLRLTCVAS;

(qq) (SEQ ID NO: 115)
QVQLVESGAELVQPSESLRLTCAAS;

(rr) (SEQ ID NO: 116)
QVQLVESGGELVQPSESLRLTCAAS;

(ss) (SEQ ID NO: 73)
QVQLVESGAELVQPGESLRLTCAAS;

(tt) (SEQ ID NO: 117)
QVQLVESGAELVQPSGSLRLTCAAS;

(uu) (SEQ ID NO: 118)
QVQLVESGGELVQPGESLRLTCAAS;

(vv) (SEQ ID NO: 119)
QVQLVESGGELVQPSGSLRLTCAAS;

(ww) (SEQ ID NO: 120)
QVQLVESGGELVQPGGSLRLTCAAS;

(xx) (SEQ ID NO: 121)
QVQLMESGAELVQPSESLRLTCAAS;

(yy) (SEQ ID NO: 122)
QVQLMESGGELVQPSESLRLTCAAS;

(zz) (SEQ ID NO: 123)
QVQLMESGAELVQPGESLRLTCAAS;

(aaa) (SEQ ID NO: 124)
QVQLMESGAELVQPSGSLRLTCAAS;

(bbb) (SEQ ID NO: 125)
QVQLMESGGELVQPGESLRLTCAAS;

(ccc) (SEQ ID NO: 126)
QVQLMESGGELVQPSGSLRLTCAAS;
and (ddd) (SEQ ID NO: 127)
QVQLMESGGELVQPGGSLRLTCAAS.

In an embodiment, the antigen-binding molecule comprises:

(a) a VH framework region 1 (FR1) comprising an amino acid sequence having at least 80% sequence identity to an amino acid sequence selected from the group consisting of SEQ ID NOs: 13, 36, 40, 44, 48, 52 and 72-127;
(b) a VH FR2 comprising an amino acid sequence having at least 80% sequence identity to an amino acid sequence selected from the group consisting of SEQ ID NOs: 14, 37, 41, 45, 49 and 53;
(c) a VH FR3 comprising an amino acid sequence having at least 80% sequence identity to an amino acid sequence selected from the group consisting of SEQ ID NOs: 15, 38, 42, 46, 50 and 54;
(d) a VH FR4 comprising an amino acid sequence having at least 80% sequence identity to an amino acid sequence selected from the group consisting of SEQ ID NOs: 16, 39, 43, 47, 51 and 55;
(e) a VL FR1 comprising an amino acid sequence having at least 80% sequence identity to an amino acid sequence selected from the group consisting of SEQ ID NOs: 17, 56, 60, 64, 68 and 129;
(f) a VL FR2 comprising an amino acid sequence having at least 80% sequence identity to an amino acid sequence selected from the group consisting of SEQ ID NOs: 18, 57, 61, 65 and 69;
(g) a VL FR3 comprising an amino acid sequence having at least 80% sequence identity to an amino acid sequence selected from the group consisting of SEQ ID NOs: 19, 58, 62, 66 and 70; and
(h) a VL FR4 comprising an amino acid sequence having at least 80% sequence identity to an amino acid sequence selected from the group consisting of SEQ ID NOs: 20, 59, 63, 67 and 71.

In an embodiment, the antigen-binding molecule comprises:
(a) a VH framework region 1 (FR1) comprising an amino acid sequence having at least 80% sequence identity to an amino acid of SEQ ID NO: 72; and
(b) a VL FR1 comprising an amino acid sequence having at least 80% sequence identity to an amino acid sequence of SEQ ID NO: 129.

In an embodiment,
(a) the VH comprises an amino acid sequence having at least 80% sequence identity to an amino acid sequence selected from the group consisting of SEQ ID NO: 12 and SEQ ID NOs: 27 to 31, and
(b) the VL comprises an amino acid sequence having at least 80% sequence identity to an amino acid sequence selected from the group consisting of SEQ ID NO: 10, SEQ ID NO: 128 and SEQ ID NOs: 32 to 35.

In another embodiment, the antigen-binding molecule comprises:
(a) a VH FR1 comprising an amino acid sequence having at least 80% sequence identity to a VHFR1 amino acid sequence selected from the group consisting of SEQ ID NO: 13 and SEQ ID NOs: 72-127,
(b) a VH FR2 comprising an amino acid sequence having at least 80% sequence identity to a VHFR2 amino acid of SEQ ID NO: 14,
(c) a VH FR3 comprising an amino acid sequence having at least 80% sequence identity to a VHFR3 amino acid sequence of SEQ ID NO: 15,
(d) a VH FR4 comprising an amino acid sequence having at least 80% sequence identity to a VHFR4 amino acid sequence of SEQ ID NO: 16,
(e) a VL FR1 comprising an amino acid sequence having at least 80% sequence identity to a VLFR1 amino acid sequence of SEQ ID NO: 17 or SEQ ID NO: 129,
(f) a VL FR2 comprising an amino acid sequence having at least 80% sequence identity to a VLFR2 amino acid sequence of SEQ ID NO: 18,
(g) a VL FR3 comprising an amino acid sequence having at least 80% sequence identity to a VLFR3 amino acid sequence of SEQ ID NO: 19, and
(h) a VL FR4 comprising an amino acid sequence having at least 80% sequence identity to a VHFR4 amino acid sequence of SEQ ID NO: 20.

In another embodiment, the antigen-binding molecule comprises:
(a) the VH comprises an amino acid sequence having at least 80% sequence identity to a VH amino acid sequence of SEQ ID NO: 12, and
(b) the VL comprises an amino acid sequence having at least 80% sequence identity to a VL amino acid sequence of SEQ ID NO: 128.

In an embodiment,
(a) the VH comprises an amino acid sequence having at least 80% sequence identity to an amino acid sequence selected from the group consisting of SEQ ID NOs: 27 to 31, and
(b) the VL comprises an amino acid sequence having at least 80% sequence identity to an amino acid sequence selected from the group consisting of SEQ ID NOs: 32 to 35.

In an embodiment, the antigen-binding molecule comprises, consists or consists essentially of:
(a) a VH framework region 1 (FR1) comprising an amino acid sequence selected from the group consisting of SEQ ID NOs: 13, 36, 40, 44, 48, 52 and 72-127;
(b) a VH FR2 comprising an amino acid sequence selected from the group consisting of SEQ ID NOs: 14, 37, 41, 45, 49 and 53;
(c) a VH FR3 comprising an amino acid sequence selected from the group consisting of SEQ ID NOs: 15, 38, 42, 46, 50 and 54;
(d) a VH FR4 comprising an amino acid sequence selected from the group consisting of SEQ ID NOs: 16, 39, 43, 47, 51 and 55;
(e) a VL FR1 comprising an amino acid sequence selected from the group consisting of SEQ ID NOs: 17, 56, 60, 64, 68 and 129;
(f) a VL FR2 comprising an amino acid sequence selected from the group consisting of SEQ ID NOs: 18, 57, 61, 65 and 69;
(g) a VL FR3 comprising an amino acid sequence selected from the group consisting of SEQ ID NOs: 19, 58, 62, 66 and 70; and
(h) a VL FR4 comprising an amino acid sequence selected from the group consisting of SEQ ID NOs: 20, 59, 63, 67 and 71.

In an embodiment,
(a) the VH comprises, consists or consists essentially of an amino acid sequence selected from the group consisting of SEQ ID NO: 12 and SEQ ID NOs: 27 to 31, and
(b) the VL comprises, consists or consists essentially of an amino acid sequence selected from the group consisting of SEQ ID NO: 10, SEQ ID NO: 128 and SEQ ID NOs: 32 to 35.

In yet another embodiment, the antigen-binding molecule comprises, consists or consists essentially of:
(a) a VH FR1 comprising an amino acid sequence of SEQ ID NO:72,
(b) a VH FR2 comprising an amino acid sequence of SEQ ID NO: 14, (c) a VH FR3 comprising an amino acid sequence of SEQ ID NO: 15,
(d) a VH FR4 comprising an amino acid sequence of SEQ ID NO: 16,
(e) a VL FR1 comprising an amino acid sequence of SEQ ID NO:17,
(f) a VL FR2 comprising an amino acid sequence of SEQ ID NO:18,
(g) a VL FR3 comprising an amino acid sequence of SEQ ID NO: 19, and
(h) a VL FR4 comprising an amino acid sequence of SEQ ID NO: 20.

In another embodiment, the antigen-binding molecule comprises, consists or consists essentially of:
(a) the VH comprises an amino acid sequence of SEQ ID NO: 12, and
(b) the VL comprises an amino acid sequence of SEQ ID NO: 128.

In an embodiment,
(a) the VH comprises, consists or consists essentially of an amino acid sequence selected from the group consisting of SEQ ID NOs: 27 to 31, and
(b) the VL comprises, consists or consists essentially of an amino acid sequence selected from the group consisting of SEQ ID NOs: 32 to 35.

Reference herein to "at least 80%" includes 80%, 85%, 86%, 87%, 88%, 89%, 90%, 91%, 92%, 93%, 94%, 95%, 96%, 97%, 98%, 99% or 100% sequence identity to any one of the recited sequences after optimal alignment or best fit analysis.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any suitable method known to persons skilled in the art. Reference also may be made to the BLAST family of programs as, for example, disclosed by Altschul et al. (1997) *Nucl. Acids. Res.* 25:3389. A detailed discussion of sequence analysis can also be found in Unit 19.3 of Ausubel et al. (1994-1998) In: Current Protocols in Molecular Biology, John Wiley & Sons Inc.

The term "sequence identity", as used herein, refers to the extent that sequences are identical or structurally similar on a nucleotide-by-nucleotide basis or an amino acid-by-amino acid basis over a window of comparison. Two or more peptide sequences may be compared by determining their "percent identity". The percent identity of two sequences may be described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable methods and computer programs for performing an alignment of two or more amino acid sequences and determining their sequence identity or homology are well known to persons skilled in the art. For example, the percentage of identity or similarity of two amino acid sequences can be readily calculated using algorithms, for example, BLAST, FASTA, or the Smith-Waterman algorithm. A "percentage of sequence identity" may therefore be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For example, "sequence identity" is the "match percentage" calculated by the DNASIS computer program (Version 2.5 for windows; available from Hitachi Software engineering Co., Ltd., South San Francisco, California, USA) using standard defaults as used in the reference manual accompanying the software.

Sequence identity includes exact identity between compared sequences at the nucleotide or amino acid level. Sequence identity, as herein described, typically relates to the percentage of amino acid residues in the candidate sequence that are identical with the residues of the corresponding peptide sequence after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology.

In another embodiment, antigen-binding molecule is an antibody or an antigen-binding fragment thereof, as described elsewhere herein. In an embodiment, the antigen-binding fragment is selected from the group consisting of a Fab fragment, scFab, Fab', a single chain variable fragment (scFv) and a one-armed antibody.

Also disclosed herein is a chimeric molecule comprising an NGF-binding molecule, as herein described, and a heterologous moiety. In some embodiments, the heterologous moiety may be a detectable moiety, a half-life extending moiety, or a therapeutic moiety. Thus, as used herein, a "chimeric" molecule is one which comprises one or more unrelated types of components or contains two or more chemically distinct regions which can be conjugated to each other, fused, linked, translated, attached via a linker, chemically synthesized, expressed from a nucleic acid sequence, etc. For example, a peptide and a nucleic acid sequence, a peptide and a detectable label, unrelated peptide sequences, and the like. In embodiments in which the chimeric molecule comprises amino acid sequences of different origin, the chimeric molecule includes (1) polypeptide sequences that are not found together in nature (i.e., at least one of the amino acid sequences is heterologous with respect to at least one of its other amino acid sequences), or (2) amino acid sequences that are not naturally adjoined. For example, a "chimeric" antibody" as used herein refers to an antibody in which a portion of the heavy and/or light chain is derived from a particular source or species, while the remainder of the heavy and/or light chain is derived from a different source or species.

The present disclosure also extends to an isolated polynucleotide comprising a nucleic acid sequence encoding the NGF-binding molecules, as described herein.

In an embodiment, the nucleic acid molecule encoding the immunoglobulin heavy chain of the NGF-binding molecule disclosed herein has at least 80% sequence identity to SEQ ID NO: 25. In an embodiment, the nucleic acid molecule encoding the immunoglobulin heavy chain of the NGF-binding molecule disclosed herein comprises, consists or consists essentially of the nucleic acid sequence of SEQ ID NO: 25.

In an embodiment, the nucleic acid molecule encoding the immunoglobulin light chain of the NGF-binding molecule disclosed herein has at least 80% sequence identity to SEQ ID NO: 26. In an embodiment, the nucleic acid molecule encoding the immunoglobulin light chain of the NGF-binding molecule disclosed herein comprises, consists or consists essentially of the nucleic acid sequence of SEQ ID NO: 26.

The term "polynucleotide" or "nucleic acid" are used interchangeably herein to refer to a polymer of nucleotides, which can be mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

Also disclosed herein is a vector that comprises a nucleic acid encoding the NGF-binding molecules, as described herein.

By "vector" is meant a nucleic acid molecule, preferably a DNA molecule derived, for example, from a plasmid, bacteriophage, or virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

In one embodiment, the vector is an adeno-associated virus (AAV) vector that enables the NGF-binding molecule, as described herein, to be safely administered to subjects and to provide a persistent expression of the NGF-binding molecule in the subject.

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

An AAV vector typically comprises an AAV protein capsid into a nucleic acid sequence is packaged for delivery to a target cell. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, AAVrh10, AAVrh64R1, AAVrh64R2, AAVrh8, AAVrh10, variants of any of the known or mentioned AAV or AAV yet to be discovered. Illustrative examples are described in US 2007/0036760A1, US 2009/0197338A1, EP 1310571, WO 2003/042397, U.S. Pat. Nos. 7,790,449, 7,282,199, WO 2005/033321, U.S. Pat. No. 7,906,111, WO 2006/110689 and WO 2003/042397, the entire contents of which are incorporated herein by reference. Alternatively, a recombinant AAV may be used as a source of the AAV capsid. In some embodiments, the AAV capsid can be generated by mutagenesis (e.g., by one or more insertions, deletions or substitutions) of one of the aforementioned AAV capsid or its encoding nucleic acid. In some embodiments, the AAV capsid is chimeric, comprising domains from two or more AAV capsid proteins. In some embodiments, the AAV capsid is a mosaic of Vp1, Vp2, and Vp3 monomers from two or more different AAV or recombinant AAV. In some embodiments, the AAV capsid shares from about 90% sequence identity to about 99.9% identity, preferably from about 95% to about 99% sequence identity or more preferably from about 97% to about 98% sequence identity to an AAV capsid provided herein and/or known in the art. In an embodiment, the AAV capsid shares at least 95% sequence identity with an AAV capsid.

In an embodiment, the AAV vector is selected from the group consisting of AAV1, AAV5, AAV6, AAV8, AAVrh64R1, AAV9, AAVrh91, AAVhu.37, AAV3b, AAV3b.AR2.12 and AAVrh10 vectors. In an embodiment, the AAV is an AAV1. In an embodiment, the AAV vector is an AAVrh91 vector.

Methods for generating and isolating AAV vectors suitable for delivery to a subject will be known to persons skilled in the art (see, e.g., U.S. Pat. Nos. 7,790,449; 7,282,199; WO 2003/042397; WO 2005/033321, WO 2006/110689; U.S. Pat. No. 7,588,772 and WO 2017/040524, the entire contents of which are incorporated herein by reference). In an embodiment, a producer cell line is transiently transfected with a construct that encodes the transgene flanked by inverted terminal repeats (ITR) and a construct(s) that encodes rep and cap. In another embodiment, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (e.g., adenovirus E1, E2a, VA, and E4 or herpesvirus UL5, ULB, UL52, and UL29, and herpesvirus polymerase) are also supplied, in trans, by the system. In these newer systems, the helper functions can be provided by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors (see, e.g., Zhang et al., 2009, *Human Gene Therapy* 20:922-929, the entire contents of which are incorporated herein by reference). Illustrative examples of suitable methods of making and using these and other AAV production systems are also described in U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065, Grieger & Samulski (2005, *Adv. Biochem. Engin/Biotechnol.* 99: 119-145) and Buning et al. (2008, *J Gene Med.* 10:717-733), the entire contents of which are incorporated herein by reference. Other illustrative examples of genetic engineering, recombinant engineering, and synthetic techniques are also described in Green and Sambrook et al, (Molecular Cloning: A Laboratory Manual, Cold Spring Harbor Press, Cold Spring Harbor, NY (2012)), the entire contents of which is incorporated herein by reference. Suitable methods of generating rAAV virions will also be well known to persons skilled in the art (see, e.g., Fisher et al. (1993) *J. Virol.*, 70:520-532 and U.S. Pat. No. 5,478,745, the entire contents of which are incorporated herein by reference). The viral vectors described herein may be delivered in a single composition or multiple compositions. Optionally, two or more different AAV may be delivered, or multiple viruses (see, e.g., WO 2011/126808 and WO 2013/049493, the entire contents of which are incorporated herein by reference).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., *Cell*, 61: 447-57 (1990)). These proteins also regulate transcription from endogenous AAV promoters and promoters within helper viruses (see, e.g., Pereira et al., *J. Virol.*, 71: 1079-1088 (1997)). The other Rep proteins modify the function of Rep78 and Rep68. The cap genes encode the capsid proteins VP1, VP2, and VP3. The cap genes are transcribed from the p40 promoter.

Also disclosed herein is an expression construct comprising a nucleic acid sequence encoding the NGF-binding molecule, as described herein, operably linked to one or more regulatory sequences.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements or regulatory sequences such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be contained within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

By "control element", "control sequence", "regulatory sequence" and the like, as used herein, is meant a nucleic acid sequence (e.g., DNA) necessary for expression of an operably linked coding sequence in a particular host cell. The control sequences that are suitable for prokaryotic cells for example, include a promoter, and optionally a cis-acting sequence such as an operator sequence and a ribosome binding site. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate mRNA stability, as well as targeting sequences that target a product encoded by a transcribed polynucleotide to an intracellular compartment within a cell or to the extracellular environment. Suitable control elements will be familiar to persons skilled in the art, illustrative examples of which include liver-specific promoters and non-tissue specific promoters (e.g., CB7). Illustrative examples of suitable liver-specific promoters include alpha 1 anti-trypsin (see, e.g., The Liver Specific Gene Promoter Database, Cold Spring Harbor, http://rulai.schl.edu/LSPD), human albumin (humAlb) (see, e.g., Miyatake et al., *J. Virol.*, 71:512432 (1997)) and hepatitis B virus core promoter (see, e.g., Sandig et al., *Gene Ther.*, 3: 10029 (1996)). In an embodiment, the liver-specific promoter thyroxin binding globulin (TBG) is used. Other suitable promoters, such as viral promoters, constitutive promoters, regulatable promoters (see, e.g., WO 2011/126808 and WO 2013/04943), or a promoter responsive to physiologic cues, may also be utilized in the vectors described herein. In an embodiment, expression of the polynucleotide encoding the antigen binding protein or NGF-binding fragment thereof, as described herein, is under the control of a liver-specific promoter (TBG). In another embodiment, expression of the polynucleotide encoding the antigen binding protein or NGF-binding fragment thereof, as described herein, is under the control of a non-tissue specific promoter (CB7).

Also disclosed herein is a host cell comprising the construct as defined herein.

The terms "host", "host cell", "host cell line" and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antigen binding molecules of the present invention. Host cells include cultured cells, e.g., mammalian cultured cells, such as CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. In one embodiment, the host cell is a CHO or HEK293 cell line.

Methods for producing a modified NGF-binding molecule, as described herein, is provided, such methods comprising culturing the host cell disclosed herein and recovering the NGF-binding molecule from the host cell or culture medium, Also disclosed herein is a pharmaceutical composition comprising the NGF-binding molecule or a vector, as described herein, and a pharmaceutically acceptable carrier.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, colouring agents, wetting or emulsifying agents, pH buffering agents, preservatives, and the like.

Representative pharmaceutically acceptable carriers include any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

The pharmaceutical compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Suitable pharmaceutical compositions may be administered intravenously, subcutaneously or intramuscularly. In some embodiments, the compositions are in the form of injectable or infusible solutions. A preferred mode of administration is parenteral (e.g., intravenous, subcutaneous, intraperitoneal, intramuscular). In specific embodiments, the pharmaceutical composition is administered by intravenous infusion or injection. In other embodiments, the pharmaceutical composition is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin and/or by the maintenance of the required particle size. In specific embodiments, an agent of the present disclosure may be conjugated to a vehicle for cellular delivery. In these embodiments, the agent may be encapsulated in a suitable vehicle to either aid in the delivery of the agent to target cells, to increase the stability of the agent, or to minimize potential toxicity of the agent. As will be appreciated by a skilled artisan, a variety of vehicles are suitable for delivering an agent of the present disclosure. Non-limiting examples of suitable structured fluid delivery systems may include nanoparticles, liposomes, microemulsions, micelles, dendrimers and other phospholipid-containing systems. Methods of incorporating agents of the present disclosure into delivery vehicles are known in the art. Although various embodiments are presented below, it will be appreciate that other methods known in the art to incorporate an antigen-binding molecule, as described herein, into a delivery vehicle are contemplated.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. An antigen-binding molecule of the present disclosure can be administered on multiple occasions. Intervals between single dosages can be daily, weekly, monthly or yearly. Intervals can also be irregular as indicated by measuring blood levels of modified polypeptide or antigen in the patient. Alternatively, the antigen-binding molecule can be administered as a sustained release formulation, in which case less frequent administration is required. Dosage and frequency vary depending on the half-life of the polypeptide in the patient.

It may be advantageous to formulate compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutically acceptable carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Dosages and therapeutic regimens of the antigen-binding molecule can be determined by a skilled artisan. In certain embodiments, the antigen-binding molecule is administered by injection (e.g., subcutaneously, intramuscularly or intravenously) at a dose of from about 0.01 to 40 mg/kg, e.g., from about 0.01 to about 0.1 mg/kg, e.g., from about 0.1 to about 1 mg/kg, from about 1 to about 5 mg/kg, from about 5 to about 25 mg/kg, from about 10 to about 40 mg/kg, or about 0.4 mg/kg. In an embodiment, the antigen-binding molecule is administered (e.g., subcutaneously, intramuscularly or intravenously) to the subject at a dose of from about 0.01 mg/kg to about 40 mg/kg, preferably from about 0.1 mg/kg to about 20 mg/kg, preferably from about 0.2 mg/kg to about 20 mg/kg, preferably from about 0.2 mg/kg to about 10 mg/kg, preferably from about 0.2 mg/kg to about 5 mg/kg, or more preferably from about 0.2 mg/kg to about 2 mg/kg body weight. In an embodiment, the antigen-binding molecule is administered (e.g., subcutaneously, intramuscularly or intravenously) to the subject at a dose of from about 0.2 mg/kg to about 0.5 mg/kg body weight (e.g., about 0.2 mg/kg, about 0.25 mg/kg, about 0.3 mg/kg, about 0.35 mg/kg, about 0.4 mg/kg, about 0.45 mg/kg, or about 0.5 mg/kg body weight). In an embodiment, the antigen-binding molecule is administered (e.g., subcutaneously, intramuscularly or intravenously) to the subject at a dose of from about 1 mg/kg to about 40 mg/kg, more preferably from about 2 mg/kg to about 20 mg/kg body weight. In an embodiment, the antigen-binding molecule is administered (e.g., subcutaneously, intramuscularly or intravenously) subcutaneously to the subject at a dose of from about 1 mg/kg to about 40 mg/kg, more preferably from about 2 mg/kg to about 20 mg/kg body weight (e.g., about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg body weight). In an embodiment, the antigen-binding molecule is administered (e.g., subcutaneously, intramuscularly or intravenously) to the subject at a dose of about 1 mg/kg body weight. In an embodiment, the antigen-binding molecule is administered subcutaneously to the subject at a dose of about 1 mg/kg body weight. In an embodiment, the antigen-binding molecule is administered (e.g., subcutaneously, intramuscularly or intravenously) to the subject at a dose of about 2 mg/kg body weight. In an embodiment, the antigen-binding molecule is administered subcutaneously to the subject at a dose of about 2 mg/kg body weight. Without being bound by theory or by a particular mode of application, the dose administered to the subject may be lower (e.g., from about 0.2-0.5 mg/kg body weight) when administered over shorter dosage intervals (e.g., about once every 1, 2, 3 or 4 weeks), or higher (e.g., from about 1-20 mg/kg body weight) when administered over longer dosage intervals (e.g., about once every 5 weeks, 6 weeks, 7 weeks, 8 weeks, 2 months, 3 months or more).

The dosing schedule can vary from, e.g., about once a week to once every 2, 3, 4, 5, 6, 7, 8, 9, 10, 11, 12 weeks or more. In an embodiment, the antigen-binding molecule or NGF-binding fragment thereof, as described herein, is administered to the subject at a dosing frequency of about once a week or less, preferably once every 2 weeks, preferably once every 3 weeks, preferably once every 4 weeks, preferably once every 5 weeks, preferably once every 6 weeks, preferably once every 7 weeks, preferably once every 8 weeks, preferably once every 9 weeks, preferably once every 10 weeks, preferably once every 11 weeks, or more preferably once every 12 weeks. In an embodiment, the antigen-binding molecule or NGF-binding fragment thereof, as described herein, is administered to the subject at a dosing frequency of about once every 2 months or more (e.g., about once every 2 months, about once every 2½ months, about once every 3 months, about once every 3½ months, about once every 4 months, about once every 4½ months, about once every 5 months, about once every 5½ months, about once every 6 months, and so on).

In an embodiment, the antigen-binding molecule is administered at a dose of from about 10 to about 20 mg/kg every other week. In an embodiment, the antigen-binding molecule is administered at a dose of from about 10 to about 20 mg/kg every other week.

As described elsewhere herein, the present inventors have also unexpectedly shown that NGF-binding antibodies, such as those described herein, are clinically effective (e.g., at pain relief) for at least 60 days (~2 months) following administration. This therapeutic benefit was independent of any modification to the Fc region of the anti-NGF antibody that would otherwise extend its serum half-life. Thus, in an embodiment, the antigen-binding molecule, the vector, or the pharmaceutical composition, as described herein, is administered to the subject about once every 2 months or more.

In an embodiment, the antigen-binding molecule is administered at a dose of from about 0.01 to about 40 mg/kg every other week, preferably from about 0.01 to about 20 mg/kg every other week, preferably from about 0.10 to about 10 mg/kg every other week, preferably from about 0.5 to about 10 mg/kg every other week, or more preferably from about 0.5 to about 50 mg/kg every other week. In one embodiment, the antigen-binding molecule is administered at a dose of about 1 mg/kg body weight every other week. An exemplary, non-limiting range for an effective amount of an antigen-binding molecule of the present disclosure is 0.01-5 mg/kg, more suitably 0.03-2 mg/kg.

Having regard to the inventors' unexpected finding that anti-NGF antibodies are therapeutically effective for at least 60 days (~2 months) following administration to a subject, as noted elsewhere herein, the present disclosure also extends to a method of treating or preventing a condition associated with increased expression and/or increased activity of NGF, the method comprising administering to a subject in need thereof an NGF-binding molecule, or an NGF-binding fragment thereof, at a dose of from about 0.5 to about 10 mg/kg body weight, preferably at a dose of about 1 mg/kg body weight, and at a dosing frequency of about once every 2 months or more. In an embodiment, the dose administered to the subject is from about 0.5 to about 5 mg/kg body weight, preferably from about 0.5 to about 2 mg/kg body weight, or more preferably about 1 mg/kg body weight. In an embodiment, the subject is a feline or a canine. In an embodiment, the NGF-binding molecule, or an NGF-binding fragment thereof, is administered to the subject subcutaneously. In an embodiment, the condition associated with increased expression and/or increased activity of NGF is pain, as described elsewhere herein. In an embodiment, the condition associated with increased expression and/or increased activity of NGF is pain associated with arthritis. In an embodiment, the condition associated with increased expression and/or increased activity of NGF is pain associated with osteoarthritis.

In another aspect, there is provided a method of treating or preventing a condition associated with increased expression and/or increased activity of NGF, the method comprising administering to a subject in need thereof an wherein the condition associated with increased expression and/or increased activity of NGF is pain, preferably pain associated with osteoarthritis, wherein the NGF-binding molecule, or the NGF-binding fragment thereof, is administered subcutaneously at a dose of from about 0.5 to about 2 mg/kg body weight, preferably about 1 mg/kg body weight, and at a dosing frequency of about 2 months or more.

The present disclosure also extends to a therapeutic anti-NGF antibody capable of delivering pain relief in a subject in need thereof for at least 60 days following administration, characterised in that said therapeutic anti-NGF antibody does not require modification to the amino acid sequence of the Fc region to achieve pain relief in the subject.

Dosages and therapeutic regimens of the polynucleotide or vector comprising a nucleic acid sequence encoding the NGF-binding molecule or NGF-binding fragment thereof described herein can also be determined by a skilled artisan. In certain embodiments, the polynucleotide or vector is administered by injection (e.g., subcutaneously, intramuscularly or intravenously) at a dose of, for example, from about $1\times10^6$ gene copy (gc)/kg body weight to about $1\times10^{16}$ gc/kg body weight (e.g., $1\times10^6$ gc/kg, $1\times10^7$ gc/kg, $1\times10^8$ gc/kg, $1\times10^9$ gc/kg, $1\times10^{10}$ gc/kg, $1\times10^{11}$ gc/kg $1\times10^{12}$ gc/kg, $1\times10^{13}$ gc/kg, $1\times10^{14}$ gc/kg, $1\times10^{15}$ gc/kg, or $1\times10^{16}$ gc/kg body weight). In an embodiment, the polynucleotide or vector described herein is administered to the subject at a dose of from about $1\times10^{10}$ gc/kg to about $1\times10^{14}$ gc/kg body weight, preferably from about $1\times10^{11}$ gc/kg to about $1\times10^{13}$ gc/kg body weight, more preferably from about $1\times10^{12}$ gc/kg to about $5\times10^{12}$ gc/kg body weight. In an embodiment, the polynucleotide or vector described herein is administered to the subject at a dose of about $1\times10^{12}$ gc/kg body weight. The dosing schedule for the polynucleotides or vectors described herein can vary from, e.g., about once a week to once every 2, 3, 4, 5, 6, 7, 8, 9, 10, 11, 12 weeks. In an embodiment, the antigen-binding molecule or NGF-binding fragment thereof, as described herein, is administered to the subject about once a week, preferably once every 2 weeks, preferably once every 3 weeks, preferably once every 4 weeks, preferably once every 5 weeks, preferably once every 6 weeks, preferably once every 7 weeks, preferably once every 8 weeks, preferably once every 9 weeks, preferably once every 10 weeks, preferably once every 11 weeks, or more preferably once every 12 weeks.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include an effective amount of agent (i.e., the NGF-binding molecule) disclosed herein. The effective amount may be a "therapeutically effective amount" or a "prophylactically effective amount". A "therapeutically effective amount" refers to an amount effective, at dosages and for periods of time necessary, to achieve the desired therapeutic result. A therapeutically effective amount of the agent may vary according to factors such as the disease state, age, sex, and weight of the individual, and the ability of the agent to elicit a desired response in the individual. A therapeutically effective amount is also one in which any toxic or detrimental effects of the agent is outweighed by the therapeutically beneficial effects. Alternatively, this property of a composition can be evaluated by examining the ability of the compound to inhibit, for example in in vitro by assays known to the skilled practitioner.

By contrast, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also disclosed herein is a method of treating, inhibiting or ameliorating pain in a subject, the method comprising the step of administering the NGF-binding molecule, or vector, as described herein, to a subject in need thereof.

The term "treating" as used herein may refer to (1) delaying the appearance of one or more symptoms of the condition; (2) inhibiting the development of the condition or one or more symptoms of the condition; (3) relieving the condition, i.e., causing regression of the condition or at least one or more symptoms of the condition; and/or (4) causing a decrease in the severity of the condition or of one or more symptoms of the condition.

The terms "treating", "treatment" and the like, are used interchangeably herein to mean relieving, reducing, alleviating, ameliorating or otherwise inhibiting the condition, including one or more symptoms of the condition. The terms "prevent", "preventing", "prophylaxis", "prophylactic", "preventative" and the like are used interchangeably herein to mean preventing or delaying the onset of the condition, or the risk of developing the condition.

The terms "treating", "treatment" and the like also include relieving, reducing, alleviating, ameliorating or otherwise inhibiting the effects of the condition for at least a period of time. It is also to be understood that terms "treating", "treatment" and the like do not imply that the condition, or a symptom thereof, is permanently relieved, reduced, alleviated, ameliorated or otherwise inhibited and therefore also encompasses the temporary relief, reduction, alleviation, amelioration or otherwise inhibition of the condition, or of a symptom thereof.

The terms "subject", "patient", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such as from the genus Macaca (e.g., cynomolgus monkeys such as Macaca fascicularis, and/or rhesus monkeys (Macaca mulatta)) and baboon (Papio ursinus), as well as marmosets (species from the genus Callithrix), squirrel monkeys (species from the genus Saimiri) and tamarins (species from the genus Saguinus), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In one embodiment, the subject is a human subject. In another embodiment, the subject is a canine subject. In another embodiment, the subject is a feline subject. In another embodiment, the subject is an equine subject.

Conditions associated with an abnormal (e.g., increased) level and/or abnormal (e.g., increased) activity of NGF will be familiar to persons skilled in the art. In an embodiment disclosed herein, the condition is pain. In an embodiment, the pain is selected from the group consisting of neuropathic pain, inflammatory pain, pruritic pain, pen-operative, post-operative and/or post-surgical pain.

As herein defined, the term "pain" typically means an unpleasant sensory and emotional experience associated with actual or potential tissue damage or described in terms of such damage.

In relation to operative or post-operative pain, the US Animal Welfare Act (Animal Welfare Act 2002. AWA regulations, CFR, Title 9 (Animals and Animal Products), Chapter 1 (Animal and Plant Health Inspection Service, Department of Agriculture). Subchapter A (Animal Welfare), Parts 1-4) defines a painful procedure as any procedure that would reasonably be expected to cause more than slight or momentary pain or distress in a subject to which that procedure was applied, that is, pain in excess of that caused by injections or other minor procedures. Therefore, if an animal (e.g. a canine, feline or porcine subject) undergoes a painful surgical procedure, the animal should receive postoperative analgesics.

A subject may be experiencing significant or chronic pain as a result of an associated medical condition such as rheumatoid arthritis, osteoarthritis, inflammation or a cancerous or malignant condition.

Also provided herein is an antigen-binding molecule, or vector, as described herein, for use in treating, inhibiting or ameliorating pain in a subject.

Also provided herein is the use of the NGF-binding molecules, or vector, as described herein, in the manufacture of a medicament for treating, inhibiting or ameliorating a condition associated with an abnormal (e.g., increased) level and/or abnormal (e.g., increased) activity of NGF in a subject in need thereof. In an embodiment, the condition is pain. In another embodiment, the condition is pain associated with arthritis. In another embodiment, the condition is arthritis. Thus, also disclosed herein is a method of treating or preventing arthritis or an arthritic condition in a subject, the method comprising the step of administering the NGF-binding molecule, or the vector, or the pharmaceutical composition, as described herein, to a subject in need thereof.

In an embodiment, the arthritis or arthritic condition is selected from the group consisting of immune mediated polyarthritis, rheumatoid arthritis and osteoarthritis.

Also provided herein is the NGF-binding molecule, or vector, as described herein, for use in the treatment or prevention of arthritis or an arthritic condition in a subject.

Also provided herein is the use of the NGF-binding molecule, or vector, as described herein, in the manufacture of a medicament for the treatment or prevention of arthritis or an arthritic condition in a subject.

Also disclosed herein is a method of treating or preventing a condition caused by, associated with, or resulting from, an increased expression of NGF or increased sensitivity to NGF in a subject in need thereof, the method comprising the step of administering the NGF-binding molecule, or vector, as described herein, to a subject in need thereof.

Also disclosed herein is the NGF-binding molecule, or the vector, or the pharmaceutical composition, as described herein, for use in the treatment of a condition caused by, associated with, or resulting from, an increased expression of NGF or increased sensitivity to NGF in a subject.

The present disclosure also extends to the use of the NGF-binding molecule, or the vector, as described herein, in the manufacture of a medicament for the treatment of a condition caused by, associated with, or resulting from, an increased expression of NGF or increased sensitivity to NGF in a subject.

The present disclosure also extends to a method for the treatment or prevention of a tumour induced to proliferate by NGF and conditions associated therewith, the method comprising administering the NGF-binding molecule, or the vector, or the pharmaceutical composition, as described herein, to a subject in need thereof.

In one embodiment, the tumour is an osteosarcoma.

Also provided herein is the NGF-binding molecule, or the vector, or the pharmaceutical composition, as described herein, for use in the treatment or prevention of a tumour induced to proliferate by NGF and conditions associated therewith, in a subject in need thereof.

The present disclosure also extends to the use of the NGF-binding molecule, or the vector, as described herein, in the manufacture of a medicament for the treatment or prevention of a tumour induced to proliferate by NGF and conditions associated therewith, in a subject in need thereof.

The present disclosure also extends to a kit comprising the NGF-binding molecule, or the vector, or the pharmaceutical composition, as described herein.

Also disclosed herein is the use of the NGF-binding molecule, or the vector, as described herein, for detecting NGF in a sample.

As used herein, "and/or" refers to and encompasses any and all possible combinations of one or more of the associated listed items, as well as the lack of combinations when interpreted in the alternative (or).

As used in this application, the singular form "a," "an," and "the" include plural references unless the context clearly dictates otherwise. For example, the term "an agent" includes a plurality of agents, including mixtures thereof.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1: Felinized Anti-NGF Antibodies

Two felinized anti-NGF monoclonal antibodies were engineered—fe_αD11_HCCDR1(F/L) and fe_αD11_HCCDR2(L/V). As shown in Tables 5 and 6, fe_αD11_HCCDR1(F/L) comprises an F to L substitution at a position corresponding to position 2 of the heavy chain CDR1 sequence of rat αD11 (as previously described in WO 2006/131951) and fe_αD11+HCCDR2(L/V) comprises an L to V substitution at a position corresponding to position 14 of the heavy chain CDR2 sequence of rat αD11. The amino acid sequences of the heavy chain and light chain variable regions of fe_αD11_HCCDR1(F/L) are shown in Table 8. The amino acid sequences of the heavy chain and light chain framework regions of fe_αD11_HCCDR1(F/L) are shown in Table 12. The amino acid sequences of the heavy chain and light chain variable regions of fe_αD11_HCCDR2(L/V) are shown in Table 9. The amino acid sequences of the heavy chain and light chain framework regions of fe_αD11_HCCDR2(L/V) are shown in Table 13. The nucleic acid sequences encoding the heavy chain and light chain variable regions of fe_αD11_HCCDR2(L/V) are shown in Table 14.

For comparison, a felinized anti-NGF monoclonal antibody (fe_αD11) was engineered using the CDR sequences derived from the rat anti-NGF monoclonal antibody, αD11. The felinized anti-NGF monoclonal antibody fe_αD11 has the heavy chain CDR sequences of SEQ ID NOs: 1, 8 and 3 and the light chain CDR sequences of SEQ ID NOs: 4-6. The amino acid sequences of the heavy chain and light chain variable regions of fe_αD11 are shown in Table 7. The amino acid sequences of the heavy chain and light chain framework regions of fe_αD11 are shown in Table 11.

The engineered felinized anti-NGF monoclonal antibodies were expressed in Chinese Hamster Ovary (CHO) cells.

Example 2: In Vivo Pharmacokinetics

Pharmacokinetic (PK) studies were conducted in healthy cats. Four animals were administered each of the felinized anti-NGF antibodies (fe_αD11, fe_αD11+HCCDR1(F/L) and fe_αD11+HCCDR2(L/V)) subcutaneously (s.c.) at 2.0 mg/kg on Days 0, 21, 42 and 63. Serum concentrations of the antibodies were assessed over 91 days. The concentration of each antibody in the serum was determined using an NGF-binding ELISA. Briefly, ELISA plates were coated with 0.1 μg/ml mouse (murine) NGF (muNGF) and blocked with PBS/0.05% Tween 20/1% BSA. muNGF-coated wells were then incubated for 1 hour at room temperature with antibody preparations, diluted in PBS/0.05% Tween 20/1% BSA (100 μl/well). Antibody concentrations ranging from 100 ng/ml to 1.56 ng/ml were used to establish a binding curve. After washing, the plates were incubated with a 1/5,000 dilution of goat anti-feline IgG-HRP in PBS/0.05% Tween 20/1% BSA. Plates were washed with PBS/0.05% Tween 20 and developed by the addition of TMB substrate. Development was stopped by the addition of 2M $H_2SO_4$, absorbance read at 450 nm and background values were subtracted from the absorbance readings. The non-compartmental pharmacokinetic parameters of the three felinized anti-NGF antibodies post-dose 1 and 4 were calculated using PKsolver. software. The data for each animal is depicted in FIG. 1 and further summarised in Table 1, below:

TABLE 1

Pharmacokinetic parameters of the felinized anti-NGF antibodies in serum following subcutaneous administration in feline:

| | fe_αD11 (n = 4) | fe_αD11_HCCDR1)(F/L) (n = 4) | fe_αD11_HCCDR2(L/V) (n = 4) |
|---|---|---|---|
| A. Post-Dose 1 | | | |
| t½ (d) | 11.39 | 7.76 | 7.91 |
| Cmax (ug/mL) | 27.02 | 30.33 | 25.28 |

TABLE 1-continued

Pharmacokinetic parameters of the felinized anti-NGF antibodies in serum following subcutaneous administration in feline:

| | fe_αD11 (n = 4) | fe_αD11_HCCDR1(F/L) (n = 4) | fe_αD11_HCCDR2(L/V) (n = 4) |
|---|---|---|---|
| AUC 0-t (µg/ml*d) | 306.65 | 350.26 | 273.64 |
| AUC 0-inf_obs (µg/ml*d) | 443.23 | 436.89 | 348.84 |
| B. Post-Dose 4 | | | |
| $t^{1/2}$ (d) | 4.39 | 6.38 | 10.11 |
| Cmax (ug/mL) | 22.57 | 23.95 | 34.53 |
| AUC 0-t (µg/ml*d) | 348.76 | 464.40 | 740.39 |
| AUC 0-inf_obs (µg/ml*d) | 367.25 | 633.75 | 829.21 |

Note that one animal from each of the fe_αD11 and fe_αD11_HCCDR1(F/L) cohorts was removed from the post-dose 4 analysis due to the rapid loss of detectable circulating antibody which was associated with anti-drug antibody (ADA) formation in those animals (see also Example 3, below).

The three felinized anti-NGF antibodies exhibited a typical pharmacokinetic (PK) profile of an antibody administered subcutaneously. Following absorption from the site of injection, peak plasma levels (Cmax) were achieved at approximately 3-4 days (Tmax). The mean elimination half-life (T½) following the first dose was calculated to be around 9 days (range ~8-11 days). The second-dose PK profile was similar to the first, with T½ estimated to be around 7 days (range ~4-10 days).

Figure 2:
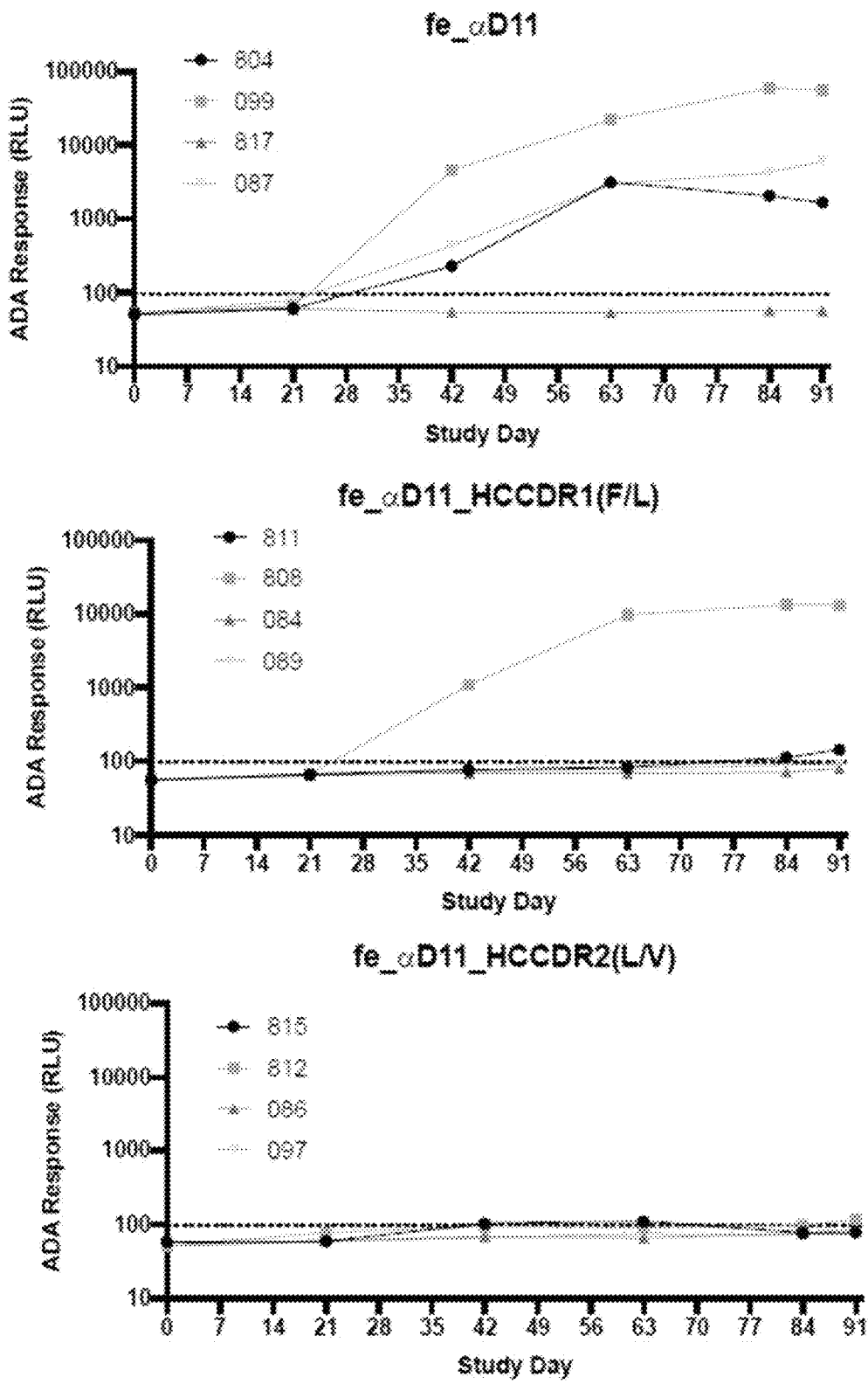
FIG. 2 shows the immunogenicity profile of the felinized anti-NGF monoclonal antibodies fel_αD11, fel_αD11_HCCDR1(F/L) and fel_αD11_HCCDR2(L/V) in cat serum following subcutaneous administration. The three felinized anti-NGF antibodies were administered at 2 mg/kg body weight subcutaneously to four cats at Day 0, 21, 42 and 63. The presence of anti-drug antibodies (ADA) at various time points was determined using a bridging immunoassay. The data for each animal is depicted.

Example 3: Immunogenicity Profile of the Felinized Anti-NGF Antibodies in Serum Following Subcutaneous Administration in Feline The three felinized anti-NGF antibodies were each administered at 2 mg/kg subcutaneously to four cats at Days 0, 21, 42 and 63. The presence of anti-drug-antibodies (ADA) at various time points was determined using a bridging immunoassay. The data for each animal is depicted in FIG. 2. A summary of the data is also set out in Table 2, below:

TABLE 2

Anti-drug-antibody (ADA) response in felines administered felinized anti-NGF antibodies fe_αD11, fe_αD11_HCCDR1(F/L) and fe_αD11_HCCDR2(L/V).

| Felinized anti-NGF antibody | ADA response |
|---|---|
| fe_αD11 | 3/4 cats (75%) |
| fe_αD11_HCCDR1(F/L) | 1/4 cats (25%) |
| fe_αD11_HCCDR2(L/V) | 0/4 cats (0%) |

These data show that the majority of animals administered fe_αD11 generated a strong ADA response, which in at least one animal was associated with a significant reduction in detectable expression of the anti-NGF antibody in serum and in a reduced T½ in the other animals. In animals administered fe_αD11_HCCDR1(F/L), one animal generated a significant ADA response that was associated with a loss of detection of the anti-NGF antibody in the serum. Advantageously, no significant ADA responses were observed in felines administered fe_αD11_HCCDR2(L/V). These data demonstrate that the V to L substitution at a position corresponding to position 14 of the heavy chain CDR2 sequence of rat αD11 (SEQ ID NO:2) unexpectedly and advantageously removed an epitope in the rat αD11 heavy chain CDR2 sequence that is otherwise immunogenic in species other than rat.

Example 4: Efficacy of Fe_αD11_HCCDR2(L/V) in Cats

A multi-center, placebo-controlled, randomized, masked (blinded) study was undertaken to evaluate the effectiveness and field safety of fe_αD11_HCCDR2(L/V) administered as a subcutaneous (SQ) monthly injection in cats for the control of pain associated with osteoarthritis (OA), in comparison with placebo.

32 cats under an established Veterinary Client Patient Relationship (VCPR) that had been diagnosed with OA by physical examination and radiography were enrolled in the study.

Day 0 was defined as the first day of dosing. Cats were randomized in a 1:1 ratio, stratified by site, in the order of enrolment following groups:

Group 1 (Placebo)—received one SQ injection of placebo on Day 0 and one SQ injection of placebo on Day 30;

Group 2 (mAb)—received one SQ injection of the anti-NGF monoclonal antibody (mAb), fe_αD11_HCCDR2 (L/V) at 2.0 mg/kg body weight) on Day 0 and a second dose on Day 30.

The primary outcome measurement was successful improvement in the owner-reported, client-specific outcome measure (CSOM) on pain. Cats were evaluated on Day 0, Day 30 and Day 90. Statistical significance was determined using an alpha of 0.1.

TABLE 3

Success was defined as a decrease in CSOM
Score of at least 2 when compared to Day 0.

| | CSOM | Placebo | fe_αD11_HCCDR2(L/V) (mAb) | p-value[b] |
|---|---|---|---|---|
| Day 30 | Success[a] | 6/15 (40.0%) | 14/17 (82.4%) | |
| | LS Means[b] | 40.1 | 82.5 | 0.0357 |
| | 95% CI[b] | 16.9, 68.8 | 54.5, 94.9 | |
| Day 90 | Success[a] | 4/11 (36.4%) | 9/12 (75.0%) | |
| | LS Means[b] | 38.7 | 75.8 | 0.1161 |
| | 95% CI[b] | 13.7, 71.6 | 42.2, 93.1 | |

[a]CSOM success defined as a reduction of at least 2 in total CSOM score compared to Day 0 with no increase in any individual activity.
[b]P-values, LS Means and LS Means Differences generated by a generalized linear mixed model, assuming a binomial distribution and logit link. Group, Day, Group-by-Day were included as fixed effects with Site and Group-by-Site interaction as random effects.

As shown in Table 3, above, a statistically significant difference was observed between mAb treatment (n=17) and placebo (n=15) groups at Day 30 (mAb: 82.5% vs. placebo: 40.1%; p=0.0357; with success defined by a reduction of at least 2 in total CSOM score compared to Day 0).

At Day 90, not all animals completed the study through that visit, reducing the total number of cats that were evaluable to 23. In any event, there was a marked difference between mAb treatment (n=12) and placebo (n=11) groups at Day 90 when success was defined by a reduction of at least 2 in total CSOM score compared to Day 0 (mAb: 75.8% vs. placebo: 38.7%; p=0.1161). This trend was also observed when a higher bar of success was applied, as defined by a reduction of at least 3 in total CSOM score compared to Day 0 (mAb: 60.1% vs. placebo: 9.9%; p=0.0608).

No treatment related adverse effects were identified in the study.

These data clearly show that fe_αD11_HCCDR2(L/V) is safe and clinically effective at reducing pain associated with OA in cats. Unexpectedly, this reduction in pain was evident up to 60 days following administration (i.e., at Day 90), which advantageously allows for the potential to administer the agents described herein as infrequently as every 2 months.

Example 5: Pharmacokinetics of Caninized Anti-NGF Antibodies in Dogs

Pharmacokinetic (PK) studies were conducted in healthy dogs. Four animals were administered purified ca_αD11_HCCDR2(L/V) subcutaneously (SC) at 1.0 mg/kg body weight on Day 0 and Day 28 of the study. The ca_αD11_HCCDR2(L/V) antibody carries the same CDR sequences as described in Tables 3 and 4, below. Serum concentrations of ca_αD11_HCCDR2(L/V) were assessed over 56 days using an NGF-binding ELISA, as detailed below. Pharmacokinetic parameters were determined using PKSolver software (Zhang Y et al. Computer Methods and Programs in Biomedicine. 2010; 99(3):306-314). The emergence of anti-drug antibodies was assessed at Days 28 and 56 using a bridging electrochemiluminescence (ECL) assay, as detailed below.

A. Quantification of Canine Anti-NGF Antibody in Dog Serum

The concentration of ca_αD11_HCCDR2(L/V) in dog serum was determined using an NGF-binding ELISA. Briefly, ELISA plates were coated with 0.1 µg/ml murine NGF (muNGF) and blocked with PBS/0.05% Tween 20/1% BSA. muNGF coated wells were incubated for 1 hour at room temperature with serum diluted in PBS/0.05% Tween 20/1% BSA (100 µl/well). Antibody concentrations ranging from 100 ng/ml to 1.56 ng/ml were used to establish a standard curve. After washing, the plates were incubated with a 1/10,000 dilution of goat anti-canine IgG-HRP in PBS/0.05% Tween 20/1% BSA. Plates were then washed with PBS/0.05% Tween 20 and developed by the addition of 3,3',5,5'-Tetramethylbenzidine (TMB) substrate. Development was stopped by the addition of 2M $H_2SO_4$ and absorbance read at 450 nm and background was subtracted.

B. Assessment of Anti-Drug Antibodies (ADA) in Dog Serum

A bridging electrochemiluminescence (ECL) assay with acid dissociation was used to evaluate the presence of ca_αD11_HCCDR2(L/V) in the dog serum at timepoints when the circulating levels of drug were at the lowest (pre-dose Day 28 and pre-dose Day 56). Samples were pre-treated with acid to disrupt any existing ADA-caNGF mAb complexes before assessment in the bridging assay. Briefly, samples were diluted to 2.5% in 300 mM acetic acid to enable ADA-drug complex dissociation before analysis. Acidified samples were incubated for 40 min with shaking at ambient temperature. 25 µL of the acidified samples were transferred to wells of a 96 well plate containing 90 µL of master-mix reagent (0.125 µg/mL of biotinylated caNGF mAb and 0.125 µg/mL of ruthenylated caNGF mAb with 1% Meso Scale Discovery (MSD) Blocker A in PBS-T) and 11 µL 1.2M Tris solution (pH 9.5). Acidified samples plus master-mix reagents were incubated at ambient temperature in the dark for 60 min with shaking. Simultaneously, Streptavidin-coated MSD plates were blocked for 60 min at ambient temperature with 200 µL/well of PBS-T buffer containing 3% (MSD) Blocker A.

The Streptavidin-coated MSD plates were then washed and 25 µL of the acidified sample plus master-mix reagent were transferred to the plates which were then incubated at ambient temperature in the dark for 60-90 min with shaking. The MSD plates were washed, 150 µL of 2×MSD Read T-Buffer was added per well before the plates were read on an MSD MESO QuickPlex SQ 120 instrument. The resulting response was recorded Relative Light Units (RLU).

C. Results

Figure 3:
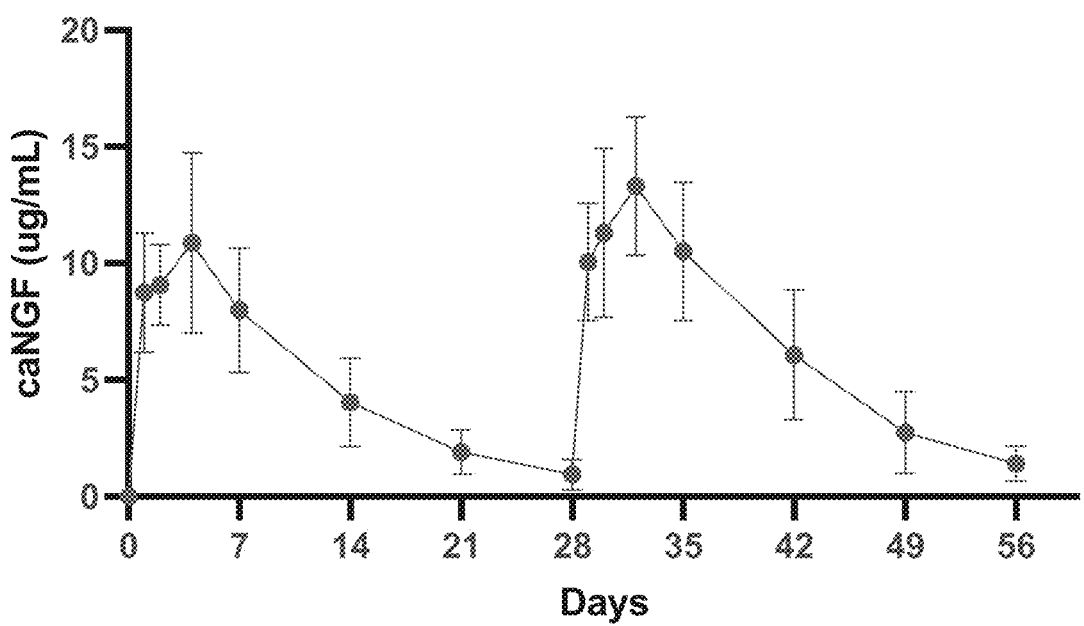
FIG. 3 shows the pharmacokinetic (PK) profile of the caninized anti-NGF antibody, ca_αD11_HCCDR2(L/V) (CaNGF), following subcutaneous administration in dogs. The ca_αD11_HCCDR2(L/V) antibody was administered subcutaneously at 1 mg/kg body weight to four dogs at Day 0 and again on Day 28. The concentration of ca_αD11_HCCDR2(L/V) was determined at the times indicated by a quantitative NGF-binding ELISA. The data is shown is the mean+/−SD.

As shown in FIG. 3, the canine anti-NGF antibody, ca_αD11_HCCDR2(L/V), exhibited a typical pharmacokinetic (PK) profile of an antibody administered SC. Following absorption from the injection, peak plasma levels (Cmax) were achieved at approximately 4 days (Tmax). The mean elimination half-life (T½) following the first dose was calculated to be 6.6 days (range 5.2-7.3 days). The second-dose PK profile was similar to the first, with T½ estimated to be 10 days (range 5.7-8 days). Following a second dose of ca_αD11_HCCDR2(L/V) at Day 28, there was no change to the PK profile, indicating that no neutralising anti-drug antibodies had developed. Furthermore, no anti-drug antibodies were detected in a bridging electrochemiluminescence (ECL) assay at Days 0, 28 and 56, demonstrating that ca_αD11_HCCDR2(L/V) was non-immunogenic following repeat dosing.

Example 6: AAV Construct Encoding fe_αD11_HCCDR2(L/V) as a Therapeutic Agent in Cats Cats were administered on Day 14 of the study a single intramuscular (IM) injection of an adeno-associated virus (AAV) vector construct comprising a nucleic acid sequence encoding the felinized anti-NGF monoclonal antibody, fe_αD11_HCCDR2(L/V), under the control of a CB7 promoter at $1 \times 10^{12}$ gc/kg body weight (AAV Group; n=18). Placebo controls received a single IM injection of saline (n=15).

The AAV used in this study was AAVrh91, as previously described in WO2021/176362, the entire contents of which is incorporated herein by reference.

Figure 4:
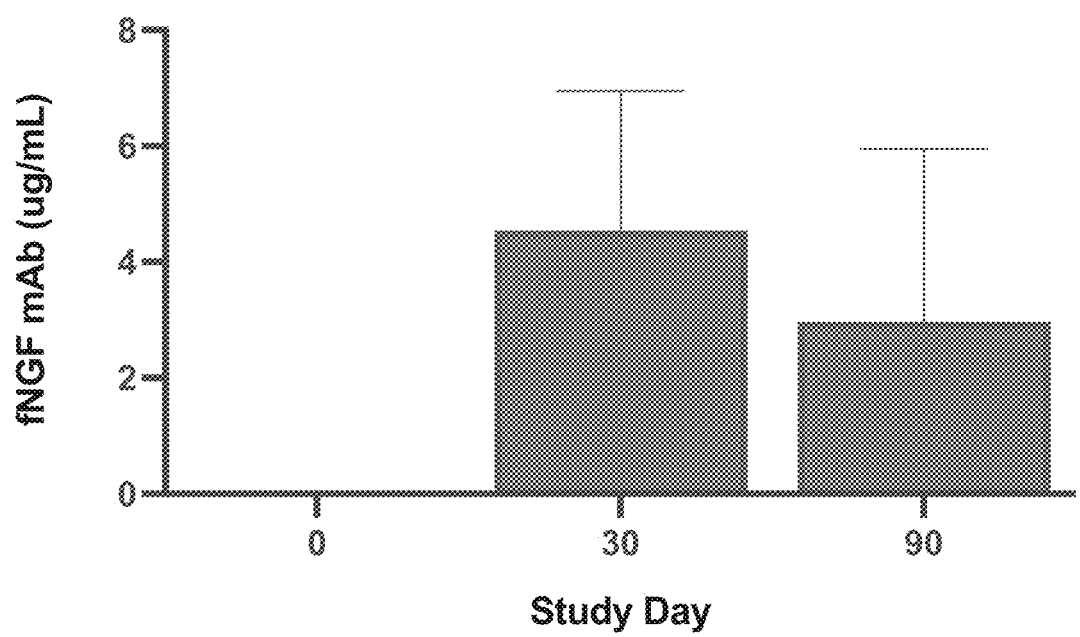
FIG. 4 shows expression of fe_αD11_HCCDR2(L/V) in cat serum following IM administration of the AAV construct comprising a transgene encoding fe_αD11_HCCDR2(L/V) at 1×10$^{12}$ gc/kg body weight on Day 14 of the study. The concentration of fe_αD11_HCCDR2(L/V) was determined at Day 30 and Day 90 by a quantitative NGF-binding ELISA. The data shown is the mean+/−SD (n=14 at Day 30 and n=6 at Day 90).

The concentration of FeNGF mAb in cat serum was determined using an NGF-binding ELISA. ELISA plates were coated with 0.1 pg/ml muNGF and blocked with PBS/0.05% Tween 20/1% BSA. muNGF coated wells were incubated for 1 h at room temperature with serum diluted in PBS/0.05% Tween 20/1% BSA in the amount of 100 pl/well. FeNGF antibody concentrations ranging from 1.56 ng/ml to 100 ng/ml were used to establish a binding curve. Well plates were washed following incubation and were then incubated with a 1/10,000 dilution of goat anti-feline IgG-HRP in PBS/0.05% Tween 20/1% BSA. Plates were washed with PBS/0.05% Tween 20 and developed by the addition of 3,3',5,5'-tetramethylbenzidine (TMB) substrate. Development was stopped by the addition of 2M $H_2SO_4$ and the absorbance read at 450 nm and background was subtracted from the resulting reading. As shown in FIG. 4, fe_αD11_HCCDR2(L/V) was detected in the serum of cats at Day 30 and Day 90 of the study following IM administration of the AAV construct.

As per Example 4, above, the primary outcome measurement was successful improvement in the owner-reported, client-specific outcome measure (CSOM). Success was defined as a decrease in CSOM Score of at least 2 or of at least 3 at Day 30 and at Day 90 of the study when compared to Day 0. Statistical significance was determined using an alpha of 0.1.

Figure 5:
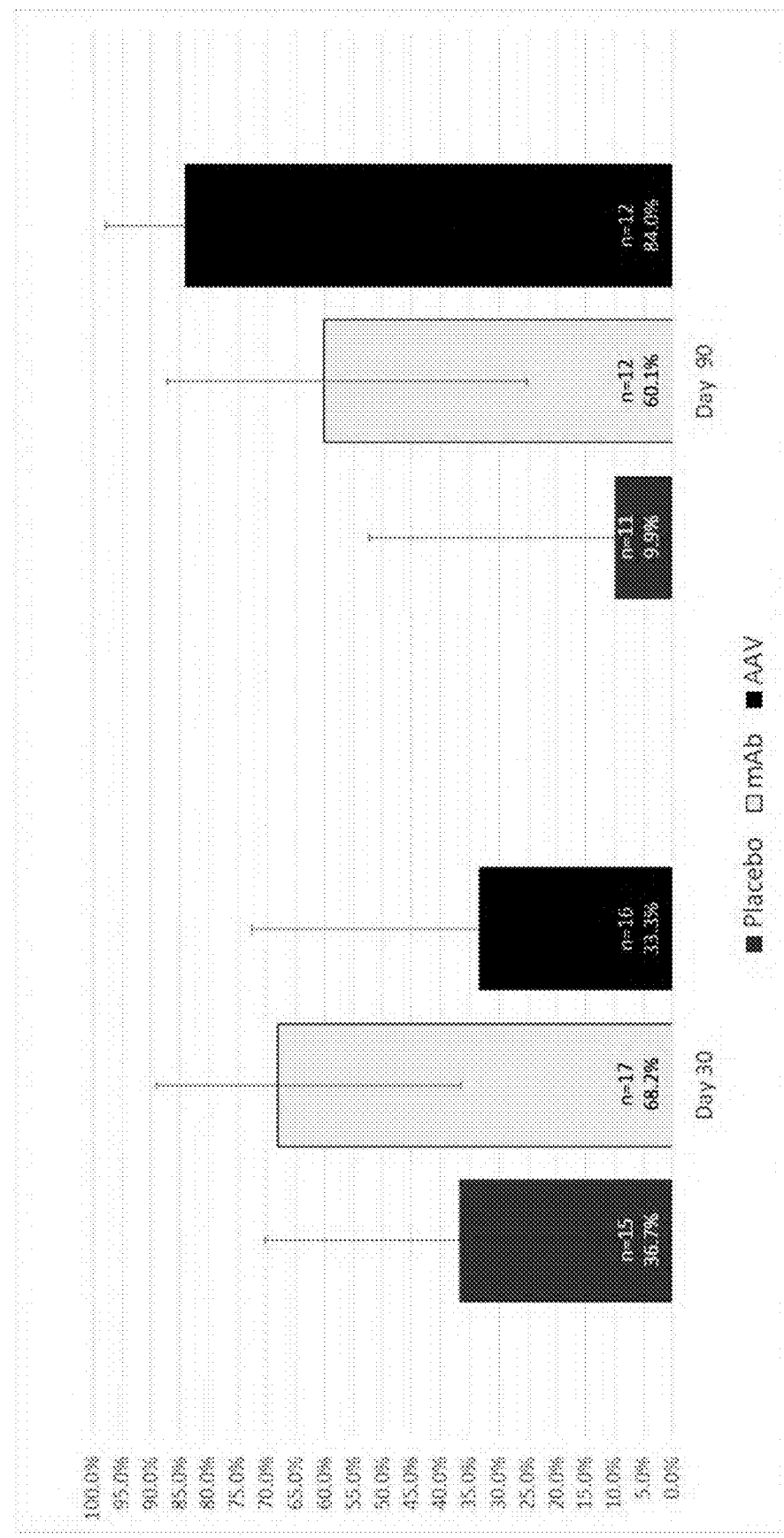
FIG. 5 shows the percentage of cats achieving clinical success following (i) subcutaneous administration of placebo at Day 0 and at Day 30 of the study; (ii) subcutaneous administration of monoclonal antibody fe_αD11_HCCDR2 (L/V) at 2 mg/kg body weight at Day 0 and at Day 30 of the study; and (iii) intramuscular administration of an AAV construct comprising a transgene encoding fe_αD11_HCCDR2(L/V), administered at 1×10$^{12}$ gc/kg body weight at Day 14 of the study; Y axis: decrease of client-specific outcome measure (CSOM) Score of ≥2 (A) or CSOM Score ≥3 (B) on Days 30 and 90 of the study (LS Mean, 95% Confidence Interval).

As shown in Table 4, below, and in FIG. 5, there was a marked difference between groups at Day 90, with the AAV construct-treated cats showing a greater success rate at Day 90 of the study when compared to placebo (see FIG. 5A: CSOM Score ≥2; AAV: 84.1%; placebo: 39.2%; p=0.0637; and FIG. 5B: CSOM Score ≥3; AAV: 84.0%; placebo: 9.9%; p=0.0215). The success rate of the AAV-treated cats was comparable to the success rate observed at Day 30 of the study in a separate cohort of cats with pain associated with osteoarthritis that were treated with the monoclonal anti-NGF antibody, fe_αD11_HCCDR2(L/V) (CSOM Score ≥2; mAb: 82.4% vs. placebo: 40.0%; p=0.0357).

TABLE 4

Success was defined as a decrease in CSOM Score of at least 2 when compared to Day 0.

| | CSOM | Placebo | fe_αD11_HCCDR2 (L/V) (mAb) | p-value | AAV construct | p-value |
|---|---|---|---|---|---|---|
| Day 30 | Success | 6/15 (40.0%) | 14/17 (82.4%) | | 11/16 (68.8%) | |
| | LS Mean | 40.1 | 82.5 | 0.0357 | 68.2 | 0.1677 |
| | 95% CI | 16.9, 68.8 | 63.0, 97.6 | | 36.0, 89.1 | |
| Day 90 | Success | 4/11 (36.4%) | 9/12 (75.0%) | | 10/12 (83.3%) | |
| | LS Mean | 38.7 | 75.8 | 0.1161 | 84.1 | 0.0.0637 |
| | 95% CI | 13.7, 71.6 | 42.2, 93.1 | | 47.0, 96.9 | |

CSOM success defined as a reduction of at least 2 in total CSOM score compared to Day 0 with no increase in any individual activity.
P-values (compared to placebo), LS Means and LS Means Differences generated by a generalized linear mixed model, assuming a binomial distribution and logit link. Group, Day, Group-by-Day were included as fixed effects with Site and Group-by-Site interaction as random effects.

These data demonstrate that treatment with a single dose of a nucleic acid construct encoding the felinized anti-NGF antibody, fe_αD11_HCCDR2(L/V), was effective at reducing pain associated with osteoarthritis in cats for at least 76 days.

TABLE 5

Amino acid sequences of the CDR of the felinized anti-NGF-binding molecule, fe_αD11 + HCCDR1(F/L), described herein (according to Kabat numbering):

| | |
|---|---|
| VH CDR1 | GLSLTNNNVN (SEQ ID NO: 7) |
| VH CDR2 | GVWAGGATDYNSALKS (SEQ ID NO: 8) |
| VH CDR3 | DGGYSSSTLYAMDA (SEQ ID NO: 3) |
| VL CDR1 | RASEDIYNALA (SEQ ID NO: 4) |
| VL CDR2 | NTDTLHT (SEQ ID NO: 5) |
| VL CDR3 | QHYFHYPRT (SEQ ID NO: 6) |

TABLE 6

Amino acid sequences of the CDR of the felinized anti-NGF-binding molecule, fe_αD11 + HCCDR2(L/V), described herein (according to Kabat numbering):

| | |
|---|---|
| VH CDR1 | GFSLTNNNVN (SEQ ID NO: 1) |
| VH CDR2 | GVWAGGATDYNSAVKS (SEQ ID NO: 2) |
| VH CDR3 | DGGYSSSTLYAMDA (SEQ ID NO: 3) |
| VL CDR1 | RASEDIYNALA (SEQ ID NO: 4) |
| VL CDR2 | NTDTLHT (SEQ ID NO: 5) |
| VL CDR3 | QHYFHYPRT (SEQ ID NO: 6) |

TABLE 7

Amino acid sequences of the heavy chain variable region (VH) and light chain variable region (VL) of the felinized anti-NGF antibody, fe_αD11, described herein (according to Kabat numbering):

VH Sequence

QVQLVESGAELVQPGESLRLTCAASGFSLTNNNVNWVRQAPGKGLEW
MGGVWAGGATDYNSALKSRLTITRDTSKNTVFLQMHSLQSEDTATYY
CARDGGYSSSTLYAMDAWGQGTTVTVSA (SEQ ID NO: 9)

VL Sequence

DIEMTQSPLSLSVTPGESVSISCRASEDIYNALAWYLQKPGRSPRLLIY**N
TDTLHTGVPDRFSGSGSGTDFTLKISRVQTEDVGVYFCQHYFHYPRT**F
GQGTKLELK (SEQ ID NO: 10)

TABLE 8

Amino acid sequences of the heavy chain variable region (VH) and light chain variable region (VL) of the felinized anti-NGF antibody, fe_αD11 HCCDR1(F/L) described herein (according to Kabat numbering):

VH Sequence

QVQLMESGADLVQPSESLRLTCVASGLSLTNNNVNWVRQAPGKGLEW
MGGVWAGGATDYNSALKSRLTITRDTSKNTVFLQMHSLQSEDTATYY
CARDGGYSSSTLYAMDAWGQGTTVTVSA (SEQ ID NO: 11)

VL Sequence

DIEMTQSPLSLSATPGETVSISCRASEDIYNALAWYLQKPGRSPRLLIY**N
TDTLHTGVPDRFSGSGSGTDFTLKISRVQTEDVGVYFCQHYFHYPRT**F
GQGTKLELK (SEQ ID NO: 128)

TABLE 9

Amino acid sequences of the heavy chain variable region (VH) and light chain variable region (VL) of the felinized anti-NGF antibody, fe_αD11_HCCDR2(L/V) described herein (according to Kabat numbering):

VH Sequence

QVQLVESGGDLVQPGGSLRLTCVASGFSLTNNNVNWVRQAPGKGLEW
MGGVWAGGATDYNSAVKSRLTITRDTSKNTVFLQMHSLQSEDTATYY
CARDGGYSSSTLYAMDAWGQGTTVTVSA (SEQ ID NO: 12)

VL Sequence

DIEMTQSPLSLSATPGETVSISCRASEDIYNALAWYLQKPGRSPRLLIY**N
TDTLHTGVPDRFSGSGSGTDFTLKISRVQTEDVGVYFCQHYFHYPRT**F
GQGTKLELK (SEQ ID NO: 128)

TABLE 10

Exemplary amino acid sequences of the heavy chain (VH) and the light chain (VL) framework regions (FR1-4) for use in felinized anti-NGF antibodies (according to Kabat numbering):

Framework Region Sequences

FR1:   QVQLMESGADLVQPSESLRLTCVAS (SEQ ID NO: 13)

FR1*:  QVQLVESGGDLVQPGGSLRLTCVAS (SEQ ID NO: 72)

FR1*:  QVQLVESGAELVQPGESLRLTCAAS (SEQ ID NO: 73)

FR2:   WVRQAPGKGLEWMG (SEQ ID NO: 14)

TABLE 10-continued

Exemplary amino acid sequences of the heavy chain (VH) and the light chain (VL) framework regions (FR1-4) for use in felinized anti-NGF antibodies (according to Kabat numbering):

FR3: RLTITRDTSKNTVFLQMHSLQSEDTATYYCAR (SEQ ID NO: 15)

FR4: WGQGTTVTVSA (SEQ ID NO: 16)

Framework Region Sequences

FR1: DIEMTQSPLSLSVTPGESVSISC (SEQ ID NO: 17)

FR1*: DIEMTQSPLSLSATPGETVSISC (SEQ ID NO: 129)

FR2: WYLQKPGRSPRLLIY (SEQ ID NO: 18)

FR3: GVPDRFSGSGSGTDFTLKISRVQTEDVGVYFC (SEQ ID NO: 19)

FR4: FGQGTKLELK (SEQ ID NO: 20)

*Alternative FR1 sequences

TABLE 11

Exemplary amino sequences of the heavy and light chains of the felinized anti-NGF antibody, fe_αD11, as expressed in CHO cells, including the signal sequence (underlined) and the constant region (italicised and underlined):

| | Heavy chain (HC) sequence |
|---|---|
| HC1 | MEWSWVFLFFLSVTTGVHSQVQLVESGAELVQPGESLRLTCAASGFSLT NNNVNWVRQAPGKGLEWMGGVWAGGATDYNSALKSRLTITRDTSKN TVFLQMHSLQSEDTATYYCARDGGYSSSTLYAMDAWGQGTTVTVSAA STTAPSVFPLAPSCGTTSGATVALACLVLGYFPEPVTVSWNSGALTSGVHTFP AVLQASGLYSLSSMVTVPSSRWLSDTFTCNVAHPPSNTKVDKTVRKTDHPPG PKPCDCPKCPPPEMLGGPSIFIFPPKPKDTLSISRTPEVTCLVVDLGPDDSD VQITWFVDNTQVYTAKTSPREEQFNSTYRVVSVLPILHQDWLKGKEFKCKVN SKSLPSPIERTISKAKGQPHEPQVYVLPPAQEELSRNKVSVTCLIKSFHPPDIA VEWEITGQPEPENNYRTTPPQLDSDGTYFVYSKLSVDRSHWQRGNTYTCSVS HEALHSHHTQKSLTQSPGK (SEQ ID NO: 21) |

| | Light chain (LC) sequence |
|---|---|
| LC1 | MSVPTQVLGLLLLWLTDARCDIEMTQSPLSLSVTPGESVSISCRASEDIY NALAWYLQKPGRSPRLLIYNTDTLHTGVPDRFSGSGSGTDFTLKISRVQ TEDVGVYFCQHYFHYPRTFGQGTKLELKRSDAQPSVFLFQPSLDELHTGS ASIVCILNDFYPKEVNVKWKVDGVVQNKGIQESTTEQNSKDSTYSLSSTLTMS STEYQSHEKFSCEVTHKSLASTLVKSFNRSECQRE (SEQ ID NO: 22) |

TABLE 12

Exemplary amino sequences of the heavy and light chains of the felinized anti-NGF antibody, fe_αD11_HCCDR1(F/L), as expressed in CHO cells, including the signal sequence (underlined) and the constant region (italicised and underlined):

| | Heavy chain (HC) sequence |
|---|---|
| HC1 | MEWSWVFLFFLSVTTGVHSQVQLMESGADLVQPSESLRLTCVASGLSL TNNNVNWVRQAPGKGLEWMGGVWAGGATDYNSALKSRLTITRDTSK NTVFLQMHSLQSEDTATYYCARDGGYSSSTLYAMDAWGQGTTVTVSA ASTTAPSVFPLAPSCGTTSGATVALACLVLGYFPEPVTVSWNSGALTSGVHTF PAVLQASGLYSLSSMVTVPSSRWLSDTFTCNVAHPPSNTKVDKTVRKTDHPP GPKPCDCPKCPPPEMLGGPSIFIFPPKPKDTLSISRTPEVTCLVVDLGPDDS DVQITWFVDNTQVYTAKTSPREEQFNSTYRVVSVLPILHQDWLKGKEFKCKV NSKSLPSPIERTISKAKGQPHEPQVYVLPPAQEELSRNKVSVTCLIKSFHPPDI AVEWEITGQPEPENNYRTTPPQLDSDGTYFVYSKLSVDRSHWQRGNTYTCSV SHEALHSHHTQKSLTQSPGK (SEQ ID NO: 23) |

TABLE 12-continued

Exemplary amino sequences of the heavy and light chains of
the felinized anti-NGF antibody, fe_αD11_HCCDR1(F/L), as expressed in
CHO cells, including the signal sequence (underlined) and the constant
region (italicised and underlined):

Light chain (LC) sequence

LC1 MSVPTQVLGLLLLWLTDARCDIEMTQSPLSLSATPGETVSISCRASEDIY
NALAWYLQKPGRSPRLLIYNTDTLHTGVPDRFSGSGSGTDFTLKISRVQ
TEDVGVYFCQHYFHYPRTFGQGTKLELK*RSDAQPSVFLFQPSLDELHTGS*
*ASIVCILNDFYPKEVNVKWKVDGVVQNKGIQESTTEQNSKDSTYSLSSTLTMS*
*STEYQSHEKESCEVTHKSLASTLVKSENRSECQRE* (SEQ ID NO: 130)

TABLE 13

Exemplary amino sequences of the heavy and light chains of
the felinized anti-NGF antibody, fe_αD11_HCCDR2(L/V), as expressed
in CHO cells, including the signal sequence (underlined) and the
constant region (italicised and underlined):

Heavy chain (HC) sequence

HC1 MEWSWVFLFFLSVTTGVHSQVQLVESGGDLVQPGGSLRLTCVASGFSL
TNNNVNWVRQAPGKGLEWMGGVWAGGATDYNSAVKSRLTITRDTSK
NTVFLQMHSLQSEDTATYYCARDGGYSSSTLYAMDAWGQGTTVTVSA
*ASTTAPSVFPLAPSCGTTSGATVALACLVLGYFPEPVTVSWNSGALTSGVHTF*
*PAVLQASGLYSLSSMVTVPSSRWLSDTFTCNVAHPPSNTKVDKTVRKTDHPP*
*GPKPCDCPKCPPPEMLGGPSIFIFPPKPKDTLSISRTPEVTCLVVDLGPDDS*
*DVQITWFVDNTQVYTAKTSPREEQFNSTYRVVSVLPILHQDWLKGKEFKCKV*
*NSKSLPSPIERTISKAKGQPHEPQVYVLPPAQEELSRNKVSVTCLIKSFHPPDI*
*AVEWEITGQPEPENNYRTTPPQLDSDGTYFVYSKLSVDRSHWQRGNTYTCSV*
*SHEALHSHHTQKSLTQSPGK* (SEQ ID NO: 24)

Light chain (LC) sequence

LC1 MSVPTQVLGLLLLWLTDARCDIEMTQSPLSLSATPGETVSISCRASEDIY
NALAWYLQKPGRSPRLLIYNTDTLHTGVPDRFSGSGSGTDFTLKISRVQ
TEDVGVYFCQHYFHYPRTFGQGTKLELK*RSDAQPSVFLFQPSLDELHTGS*
*ASIVCILNDFYPKEVNVKWKVDGVVQNKGIQESTTEQNSKDSTYSLSSTLTMS*
*STEYQSHEKFSCEVTHKSLASTLVKSFNRSECQRE* (SEQ ID NO: 130)

TABLE 14

Exemplary nucleic acid sequences encoding the heavy and
light chains of the felinized anti-NGF antibody,
fe_αD11_HCCDR2(L/V), for expression in CHO cells, including
nucleic acid sequences encoding the signal sequence
(underlined) and the constant region (italicised and underlined):

Heavy chain (HC) sequence

HC1 ATGGAATGGTCTTGGGTGTTCCTGTTCTTCCTGTCCGTGACCACCGGC
GTGCACTCTCAGGTTCAGCTGGTTGAATCTGGCGGCGACCTTGTTCA
GCCTGGCGGATCTCTGAGACTGACCTGTGTGGCCTCTGGCTTCTCCCT
GACCAACAACAACGTGAACTGGGTCCGACAGGCCCCTGGCAAAGGA
CTGGAATGGATGGGCGGAGTTTGGGCTGGCGGCGCTACCGATTACA
ACTCCGCCGTGAAGTCCCGGCTGACCATCACCAGAGACACCTCCAAG
AACACCGTGTTTCTGCAGATGCACTCCCTGCAGTCTGAGGACACCGC
CACCTACTACTGTGCTAGAGATGGCGGCTACTCCAGCAGCACCCTGT
ACGCTATGGATGCTTGGGGCCAGGGCACCACCGTGACAGTTTCTGCC
*GCTTCTACCACCGCTCCTAGCGTGTTCCCTCTGGCTCCTTCTTGTGGCAC*
*CACCTCTGGTGCTACAGTGGCTCTGGCATGTCTGGTGCTGGGCTACTTTC*
*CTGAGCCTGTGACCGTGTCCTGGAACTCTGGCGCTCTGACATCTGGCGT*
*GCACACCTTTCCAGCTGTGCTGCAGGCTTCCGGCCTGTACTCTCTGTCCT*
*CTATGGTCACCGTGCCTTCCAGCAGATGGCTGTCCGACACCTTCACCTGT*
*AACGTGGCCCATCCTCCTAGCAACACCAAGGTGGACAAGACCGTGCGCA*
*AGACCGATCATCCTCCTGGACCTAAGCCTTGCGACTGCCCTAAGTGTCCT*
*CCACCTGAGATGCTCGGCGGACCCAGCATCTTCATCTTCCCACCTAAGCC*
*AAAGGACACCCTGTCCATCTCTCGGACCCCTGAAGTGACCTGCCTGGTG*
*GTTGATCTGGGCCCTGACGACTCTGACGTGCAGATCACTTGGTTTGTGGA*
*CAACACCCAGGTGTACACAGCCAAGACCTCTCCAAGAGAGGAACAGTTCA*
*ACTCCACCTACAGAGTGGTGTCCGTGCTGCCCATCCTGCACCAGGATTG*
*GCTGAAGGGCAAAGAATTCAAGTGCAAAGTGAACTCCAAGAGCCTGCCTT*
*CTCCAATCGAGCGGACCATCTCCAAGGCTAAGGGCCAGCCTCATGAGCC*
*TCAGGTGTACGTTCTGCCTCCTGCTCAAGAGGAACTGTCCCGGAACAAAG*

TABLE 14-continued

Exemplary nucleic acid sequences encoding the heavy and light chains of the felinized anti-NGF antibody, fe_αD11_HCCDR2(L/V), for expression in CHO cells, including nucleic acid sequences encoding the signal sequence (underlined) and the constant region (italicised and underlined):

*TGTCTGTGACCTGTCTGATCAAGAGCTTTCACCCTCCTGATATCGCCGTG*
*GAATGGGAGATCACCGGACAGCCTGAGCCAGAGAACAACTACCGGACCA*
*CACCTCCTCAGCTGGACTCCGATGGCACCTACTTCGTGTACTCCAAGCTG*
*TCCGTGGACAGATCCCACTGGCAGCGGGGCAATACCTACACCTGTTCCG*
*TGTCTCACGAGGCCCTGCACTCCCATCACACCCAGAAGTCCCTGACTCAG*
*AGCCCCGGCAAG* (SEQ ID NO: 25)

Light chain (LC) sequence

LC1  ATGTCTGTGCCTACACAGGTTCTGGGACTGCTGCTGCTGTGGCTGAC
CGACGCCAGATGCGACATCGAGATGACCCAGTCTCCACTGAGCCTGT
CTGCTACCCCTGGCGAGACAGTGTCCATCTCCTGTAGAGCCTCCGAG
GACATCTACAACGCCCTGGCTGGTATCTGCAGAAGCCTGGCAGATC
CCCTCGGCTGCTGATCTACAACACCGACACACTGCATACCGGCGTGC
CCGACAGATTTTCCGGCTCTGGCTCTGGCACCGACTTCACCCTGAAG
ATTTCTCGGGTGCAGACCGAGGACGTGGGCGTGTACTTTTGCCAGCA
CTACTTTCACTACCCTCGGACCTTTGGCCAGGGCACCAAGCTGGAAC
TGAAG*AGATCCGACGCTCAGCCCTCCGTGTTCCTGTTCCAGCCTTCTCT*
*GGATGAGCTGCACACCGGCTCCGCCTCTATCGTGTGCATCCTGAACGAC*
*TTCTACCCCAAAGAAGTGAACGTGAAGTGGAAGGTGGACGGCGTGGTGC*
*AGAACAAGGGCATCCAAGAGTCTACCACCGAGCAGAACTCCAAGGACTC*
*CACCTACAGCCTGAGCAGCACCCTGACCATGTCCTCCACCGAGTACCAG*
*AGCCACGAGAAGTTCAGCTGCGAAGTGACCCACAAGTCCCTGGCTTCTA*
*CCCTGGTCAAGTCCTTCAACAGATCCGAGTGCCAGCGCGAG* (SEQ ID NO: 26)

TABLE 15

A comparison of the CDR sequences of the heavy chain variable regions of the felinized anti-NGF antibodies fe_αD11, fe_αD11_HCCDR1(F/L) and fe_αD11_HCCDR2(L/V). The amino acid substitutions when compared to the rat aD11 are highlighted by bold and underlined text:

|  | HC_CDR1 | HC_CDR2 | HC_CDR3 |
| --- | --- | --- | --- |
| fe_αD11 | GFSLTNNNVN (SEQ ID NO: 1) | GVWAGGATDYNSALKS (SEQ ID NO: 8) | DGGYSSSTLYAMDA (SEQ ID NO: 3) |
| fe_αD11_HC CDR1(F/L) | GLSLTNNNVN (SEQ ID NO: 7) | GVWAGGATDYNSALKS (SEQ ID NO: 8) | DGGYSSSTLYAMDA (SEQ ID NO: 3) |
| fe_αD11_HC CDR2(L/V) | GFSLTNNNVN (SEQ ID NO: 1) | GVWAGGATDYNSAVKS (SEQ ID NO: 2) | DGGYSSSTLYAMDA (SEQ ID NO: 3) |

TABLE 16

Exemplary amino acid sequences of the heavy chain (VH) and light chain (VL) variable regions of caninized anti-NGF antibodies comprising the L to V substitution in the heavy chain CDR2 sequence relative to the corresponding CDR2 sequence of the rat αD11 (the CDR sequences are highlighted by bold and underlined text):

Caninized VH Sequences

VH1  QVQLQESGPGLVKPSQTLSLTCTVSGFSLTNNNVNWVRQRTGRGLEW
MGGVWAGGATDYNSAVKSRLSITRDTAKSQVSLQMSSMTTEDTATYY
CARDGGYSSSTLYAMDAWGQGTSVTSS (SEQ ID NO: 27)

VH2  QVQLQESGPGLVKPSQTLSLTCTVSGFSLTNNNVNWVRQRPGRGLEW
MGGVWAGGATDYNSAVKSRLSITRDTAKSQVSLQMSSMTTEDTATYY
CARDGGYSSSTLYAMDAWGQGTLVTVSS (SEQ ID NO: 28)

VH3  QVQLQESGPGLVKPSQTLSLTCTVSGFSLTNNNVNWVRQRPGRGLEW
MGGVWAGGATDYNSAVKSRSITRDTAKSQVSLQLSSMTTEDTATYY
CARDGGYSSSTLYAMDAWGQGTLVTVSS (SEQ ID NO: 29)

TABLE 16-continued

Exemplary amino acid sequences of the heavy chain (VH) and light chain (VL) variable regions of caninized anti-NGF antibodies comprising the L to V substitution in the heavy chain CDR2 sequence relative to the corresponding CDR2 sequence of the rat αD11 (the CDR sequences are highlighted by bold and underlined text):

VH4  EVTLQESGPGLVKPSQTLSLTCTVSGFSLTNNNVNWVRQRPGRGLEWM
     GGVWAGGATDYNSAVKSRISITRDTAKNQVSLQLSSMTTEDTATYYC
     ARDGGYSSSTLYAMDAWGQGTLVTVSS (SEQ ID NO: 30)

VH5  EVTLQESGPGLVKPSQTLSLTCVVSGFSLTNNNVNWVRQRPGRGLEW
     MGGVWAGGATDYNSAVKSRISITRDTAKNQVSLQLSSMTTEDTAVYY
     CARDGGYSSSTLYAMDAWGQGTLVTVSS (SEQ ID NO: 31)

Caninized VL Sequences

VL1  DIQMTQSPASLSLSQEEKVTITCRASEDIYNALAWYQQKPGQAPKLLIY
     NTDTLHTGVPSRFSGSGSGTDYSFTISSLESEDVASYFCQHYFHYPRTF
     GAGTKVELK (SEQ ID NO: 32)

VL2  DIQMTQSPASLSLSQEEKVTITCRASEDIYNALAWYQQKPGQAPKLLIY
     NTDTLHTGVPSRFSGSGSGTDYSFTISSLEPEDVASYFCQHYFHYPRTF
     GAGTKVELK (SEQ ID NO: 33)

VL3  EIVMTQSPASLSLSQEEKVTITCRASEDIYNALAWYQQKPGQAPKLLIY
     NTDTLHTGVPSRFSGSGSGTDYSFTISSLEPEDVASYFCQHYFHYPRTF
     GAGTKVELK (SEQ ID NO: 34)

VL4  EIVMTQSPASLSLSQEEKVTITCRASEDIYNALAWYQQKPGQAPKLLIY
     NTDTLHTGVPSRFSGSGSGTDYSFTISSLEPEDVAVYFCQHYFHYPRTF
     GAGTKVELK (SEQ ID NO: 35)

TABLE 17

Exemplary framework region sequences of caninized VH and VL:

Caninized VH Framework Region Sequences

VH1  FR1 QVQLQESGPGLVKPSQTLSLTCTVS (SEQ ID NO: 36)
     FR2 WVRQRTGRGLEWMG (SEQ ID NO: 37)
     FR3 RLSITRDTAKSQVSLQMSSMTTEDTATYYCAR (SEQ ID NO: 38)
     FR4 WGQGTSVTVSS (SEQ ID NO: 39)

VH2  FR1 QVQLQESGPGLVKPSQTLSLTCTVS (SEQ ID NO: 40)
     FR2 WVRQRPGRGLEWMG (SEQ ID NO: 41)
     FR3 RLSITRDTAKSQVSLQMSSMTTEDTATYYCAR (SEQ ID NO: 42)
     FR4 WGQGTLVTVSS (SEQ ID NO: 43)

VH3  FR1 QVQLQESGPGLVKPSQTLSLTCTVS (SEQ ID NO: 44)
     FR2 WVRQRPGRGLEWMG (SEQ ID NO: 45)
     FR3 RISITRDTAKSQVSLQLSSMTTEDTATYYCAR (SEQ ID NO: 46)
     FR4 WGQGTLVTVSS (SEQ ID NO: 47)

VH4  FR1 EVTLQESGPGLVKPSQTLSLTCTVS (SEQ ID NO: 48)
     FR2 WVRQRPGRGLEWMG (SEQ ID NO: 49)
     FR3 RISITRDTAKNQVSLQLSSMTTEDTATYYCAR (SEQ ID NO: 50)
     FR4 WGQGTLVTVSS (SEQ ID NO: 51)

VH5  FR1 EVTLQESGPGLVKPSQTLSLTCVVS (SEQ ID NO: 52)
     FR2 WVRQRPGRGLEWMG (SEQ ID NO: 53)
     FR3 RISITRDTAKNQVSLQLSSMTTEDTAVYYCAR (SEQ ID NO: 54)
     FR4 WGQGTLVTVSS (SEQ ID NO: 55)

Caninized VL Framework Region Sequences

VL1  FR1 DIQMTQSPASLSLSQEEKVTITC (SEQ ID NO: 56)
     FR2 WYQQKPGQAPKLLIY (SEQ ID NO: 57)
     FR3 GVPSRFSGSGSGTDYSFTISSLESEDVASYFC (SEQ ID NO: 58)
     FR4 FGAGTKVELK (SEQ ID NO: 59)

VL2  FR1: DIQMTQSPASLSLSQEEKVTITC (SEQ ID NO: 60)
     FR2: WYQQKPGQAPKLLIY (SEQ ID NO: 61)
     FR3: GVPSRFSGSGSGTDYSFTISSLEPEDVASYFC (SEQ ID NO: 62)
     FR4: FGAGTKVELK (SEQ ID NO: 63)

TABLE 17-continued

Exemplary framework region sequences of caninized VH and VL:

VL3  FR1: EIVMTQSPASLSLSQEEKVTITC (SEQ ID NO: 64)
     FR2: WYQQKPGQAPKLLIY (SEQ ID NO: 65)
     FR3: GVPSRFSGSGSGTDYSFTISSLEPEDVASYFC (SEQ ID NO: 66)
     FR4: FGAGTKVELK (SEQ ID NO: 67)

VL4  FR1: EIVMTQSPASLSLSQEEKVTITC (SEQ ID NO: 68)
     FR2: WYQQKPGQAPKLLIY(SEQ ID NO: 69)
     FR3: GVPSRFSGSGSGTDYSFTISSLEPEDVAVYFC(SEQ ID NO: 70)
     FR4: FGAGTKVELK (SEQ ID NO: 71)

TABLE 18

Amino acid sequences of the heavy chain (VH) and light chain (VL) variable regions of caninized anti-NGF antibody, ca_αD11_HCCDR2(L/V), comprising the L to V substitution in the heavy chain CDR2 sequence relative to the corresponding CDR2 sequence of the rat aD11 (the CDR sequences are highlighted by bold and underlined text):

VH  EVTLQESGPGLVKPSQTLSLTCVVSGFSLTNNNVNWVRQRPGRGL
    EWMGGVWAGGATDYNSAVKSRISITRDTAKNQVSLQLSSMTTED
    TAVYYCARDGGYSSSTLYAMDAWGQGTLVTVSS (SEQ ID NO: 131)

VL  EIVMTQSPASLSLSQEEKVTITCRASEDIYNALAWYQQKPGQAPKL
    LIYNTDTLHTGVPSRFSGSGSGTDYSFTISSLEPEDVAVYFCQHYFH
    YPRTFGAGTKVELK (SEQ ID NO: 132)

TABLE 19

Exemplary nucleic acid sequences encoding the heavy chain (HC) and light chain (LC) of the caninized anti-NGF antibody, ca_αD11_HCCDR2(L/V), optimized for codon usage in human cells, excluding the nucleic acid sequences encoding the signal sequences. The nucleic acid sequences encoding the CDR sequences are highlighted by bold and underlined text:

Heavy chain (HC) sequence

HC  GAAGTGACCCTGCAAGAGTCTGGCCCTGGCCTGGTTAAGCCTAGCCA
    GACACTGAGCCTGACCTGTGTGGTGTCCGGCTTCAGCCTGACCAAC
    AACAACGTGAACTGGGTCCGACAGAGGCCTGGCAGAGGACTGGAA
    TGGATGGGCGGAGTTTGGGCTGGCGGAGCCACCGATTACAACAG
    CGCCGTGAAGTCCCGGATCAGCATCACCAGAGACACCGCCAAGAA
    CCAGGTGTCCCTGCAGCTGAGCAGCATGACCACAGAGGATACCGCC
    GTGTACTACTGCGCCAGAGATGGCGGCTACAGCAGCAGCACACTG
    TACGCCATGGATGCCTGGGGACAGGGCACACTGGTTACAGTGTCTA
    GCGCCAGCACAACAGCCCCTAGCGTTTTCCCTCTGGCTCCATCTTGT
    GGCAGCACCAGCGGATCTACAGTGGCTCTGGCTTGTCTGGTGTCAGG
    CTACTTCCCTGAGCCTGTGACCGTGTCCTGGAATAGCGGCTCTCTGA
    CAAGCGGCGTGCACACATTTCCAAGCGTGCTGCAGTCTAGCGGCCTG
    CACTCTCTGTCCAGCATGGTCACAGTGCCCAGCAGCAGATGGCCCAG
    CGAGACATTCACCTGTAACGTGGTGCACCCCGCCAGCAACACCAAG
    GTGGACAAGCCCGTGTTCAACGAGTGCAGATGCACCGACACACCTC
    CATGTCCTGTGCCTGAACCTCTCGGCGGACCTAGCGTGCTGATCTTC
    CCACCTAAGCCTAAGGACATCCTGCGGATCACCCGGACACCTGAAGT
    GACATGCGTGGTGCTGGATCTGGGCAGAAGATCCCGAGGTGCAG
    ATCAGTTGGTTCGTGGACGGCAAAGAGGTGCACACCGCTAAGACCC
    AGAGCAGAGAGCAGCAGTTCAACGGCACCTACAGAGTGGTGTCTGT
    GCTGCCCATCGAGCACCAGGATTGGCTGACCGGCAAGAATTCAAG
    TGCCGCGTGAACCACATCGACCTGCCTTCTCCAATCGAGCGGACCAT
    CAGCAAGGCCAGAGGCAGAGCCCACAAGCCTTCCGTGTATGTCCTG
    CCTCCATCTCCTAAAGAGCTGTCCAGCTCCGACACCGTGTCCATCAC
    CTGTCTGATCAAGGACTTCTACCCTCCTGACATCGACGTGGAATGGC
    AGAGCAACGGCCAGCAAGAGCCCGAGAGAAAGCACAGAATGACCC
    CTCCACAGCTGGACGAGGACGGCAGCTACTTCCTGTACAGCAAGCTG
    AGCGTGGACAAGAGCCGATGGCAGCAGGGCGATCCTTTTACCTGTG
    CCGTGATGCACGAGACACTGCAGAACCACTACACCGATCTGTCCCTG
    TCTCACAGCCCCGGCTGA (SEQ ID NO: 133)

Light chain (LC) sequence

LC  GAGATCGTGATGACACAGTCTCCAGCCAGCCTGAGCCTGTCTCAAGA
    GGAAAAAGTGACCATCACCTGTCGGGCCAGCGAGGACATCTATAA

TABLE 19-continued

Exemplary nucleic acid sequences encoding the heavy chain (HC) and light chain (LC) of the caninized anti-NGF antibody, ca_αD11_HCCDR2(L/V), optimized for codon usage in human cells, excluding the nucleic acid sequences encoding the signal sequences. The nucleic acid sequences encoding the CDR sequences are highlighted by bold and underlined text:

TGCCCTGGCCTGGTATCAGCAGAAGCCCGGACAAGCCCCTAAGCTG
CTGATCTACAACACCGACACACTGCACACCGGCGTGCCCAGCAGA
TTTTCTGGCTCTGGCAGCGGCACCGACTACAGCTTTACAATCAGCAG
CCTGGAACCTGAGGACGTGGCCGTGTACTTCTGC**CAGCACTACTTT
CACTACCCCAGAACC**TTCGGAGCCGGCACCAAGGTGGAACTGAAG
AGAAACGATGCCCAGCCTGCCGTGTACCTGTTCCAGCCTTCTCCAGA
TCAGCTGCACACAGGCTCTGCCAGCGTTGTGTGCCTGCTGAACAGCT
TCTACCCCAAGGACATCAACGTGAAGTGGAAGGTGGACGGCGTGAT
CCAGGACACCGGCATCCAAGAGTCTGTGACCGAGCAGGACAAGGAC
AGCACCTACAGCCTGTCTAGCACCCTGACCATGAGCAGCACCGAGTA
CCTGAGCCACGAGCTGTACTCTTGCGAGATCACCCACAAGAGCCTGC
CAAGCACACTGATCAAGAGCTTCCAGCGGAGCGAGTGCCAGAGAGT
GGATTGA (SEQ ID NO: 134)

TABLE 20

Exemplary nucleic acid sequences encoding the heavy chain (HC) and light chain (LC) of the caninized anti-NGF antibody, ca αD11_HCCDR2(L/V), optimized for codon usage in Chinese Hamster cells, excluding the nucleic acid sequences encoding the signal sequences. The nucleic acid sequences encoding the CDR sequences are highlighted by bold and underlined text:

Heavy chain (HC) sequence

HC GAAGTGACCCTGCAAGAGTCTGGCCCTGGCCTGGTTAAGCCCTCTCA
GACCCTGTCTCTGACCTGCGTGGTGTCC**GGCTTCTCCCTGACCAAC
AACAACGTGAAC**TGGGTCCGACAGAGGCCTGGCAGAGGACTGGAA
TGGATGGGC**GGAGTTTGGGCTGGCGGCGCTACCGATTACAACTC
CGCCGTGAAGTCC**CGGATCAGCATCACCAGAGACACCGCCAAGAA
CCAGGTGTCCCTGCAGCTGTCCTCTATGACCACCGAGGATACCGCCG
TGTACTACTGCGCTAGA**GATGGCGGCTACTCCAGCTCTACCCTGT
ACGCCATGGATGCT**TGGGGCCAGGGAACACTGGTCACCGTGTCCTC
CGCTTCTACCACCGCTCCATCTGTGTTCCCTCTGGCTCCTTCTTGCGG
CTCTACCTCCGGATCTACAGTGGCTCTGGCCTGTCTGGTGTCTGGCTA
CTTTCCTGAGCCTGTGACCGTGTCTTGGAACTCCGGCTCTCTGACATC
CGGCGTGCACACCTTTCCATCCGTGCTGCAGTCTAGCGGCCTGCACT
CTCTGAGTTCTATGGTTACCGTGCCTTCCAGCCGGTGGCCTTCCGAG
ACATTCACCTGTAACGTGGTGCACCCCGCCTCCAACACCAAGGTGGA
CAAGCCTGTGTTCAACGAGTGCAGATGCACCGACACACCTCCATGTC
CTGTGCCTGAACCTCTCGGCGGACCTTCCGTGCTGATCTTCCCACCTA
AGCCTAAGGACATCCTGCGGATCACCCGGACACCTGAAGTGACATG
TGTGGTGCTGGACCTGGGCCGAGAGGATCCTGAAGTGCAGATCAGTT
GGTTCGTGGACGGCAAAGAGGTGCACACCGCTAAGACCCAGTCCAG
AGAGCAGCAGTTCAACGGCACCTACAGAGTGGTGTCTGTGCTGCCCA
TCGAGCACCAGGATTGGCTGACCGGCAAAGAATTCAAGTGCCGCGT
GAACCACATCGACCTGCCTTCTCCAATCGAGCGGACCATCTCCAAGG
CTAGAGGCAGAGCCCACAAGCCTTCCGTGTATGTCCTGCCTCCATCT
CCTAAAGAGCTGTCCAGCTCCGACACCGTGTCTATCACCTGTCTGAT
CAAGGACTTCTACCCTCCTGACATCGACGTGGAATGGCAGTCCAACG
GCCAGCAAGAGCCCGAGAGAAAGCACAGAATGACCCCTCCACAGCT
GGACGAGGACGGCTCCTACTTCCTGTACTCCAAGCTGTCCGTGGACA
AGTCCAGATGGCAGCAAGGCGACCCTTTCACCTGTGCCGTGATGCAC
GAGACACTGCAGAACCACTACACCGATCTGTCCCTGTCTCACTCCCC
TGGCTGA (SEQ ID NO: 135)

Light chain (LC) sequence

LC GAGATCGTGATGACCCAGTCTCCTGCCTCTCTGTCCCTGAGCCAAGA
GGAAAAAGTGACCATCACCTGT**CGGGCCTCCGAGGACATCTACAA
TGCCCTGGCT**TGGTATCAGCAGAAGCCCGGCCAGGCTCCTAAGCTG
CTGATCTACAACACCGACACACTGCACACCGGCGTGCCCTCTAGAT
TTTCCGGCTCTGGCTCTGGCACCGACTACAGCTTTACCATCTCCAGCC
TGGAACCTGAGGACGTGGCCGTGTACTTCTGC**CAGCACTACTTTCA
CTACCCTCGGACC**TTTGGCGCTGGCACCAAGGTGGAACTGAAGCGG
AATGATGCCCAGCCTGCCGTGTACCTGTTCCAGCCTTCCAGATCA
GCTGCATACCGGCTCTGCCTCCTCGTGTGTCTGCTGAACAGCTTCTA
CCCCAAGGACATCAACGTGAAGTGGAAGGTGGACGGCGTGATCCAG
GACACCGGCATCCAAGAGTCTGTGACCGAGCAGGACAAGGACTCCA
CCTACAGCCTGTCTAGCACCCTGACCATGTCCTCCACCGAGTACCTG

TABLE 20-continued

Exemplary nucleic acid sequences encoding the heavy chain
(HC) and light chain (LC) of the caninized anti-NGF antibody,
ca αD11_HCCDR2(L/V), optimized for codon usage in Chinese Hamster
cells, excluding the nucleic acid sequences encoding the signal
sequences. The nucleic acid sequences encoding the CDR sequences
are highlighted by bold and underlined text:

AGCCACGAGCTGTACTCTTGCGAGATCACCCACAAGTCCCTGCCTTC
CACACTGATCAAGTCCTTCCAGCGGAGCGAGTGCCAGAGAGTGGAT
TGA (SEQ ID NO: 136)

TABLE 21

Exemplary nucleic acid sequences encoding the heavy chain
(HC) and light chain (LC) of the caninized anti-NGF antibody,
ca_αD11_HCCDR2(L/V), optimized for codon usage in canine cells,
excluding the nucleic acid sequences encoding the signal sequences.
The nucleic acid sequences encoding the CDR sequences are
highlighted by bold and underlined text:

Heavy chain (HC) sequence

| HC | GAAGTGACCCTGCAAGAGTCTGGCCCTGGCCTGGTCAAACCTTCTCA<br>GACCCTGAGCCTGACCTGCGTGGTGTCTGGATTCAGCCTGACCAAC<br>AACAACGTGAACTGGGTCCGACAGAGGCCTGGCAGAGGACTGGAA<br>TGGATGGGCGGAGTTTGGGCTGGCGGAGCCACCGATTACAACAG<br>CGCCGTGAAGTCCAGGATCAGCATCACCAGAGACACCGCCAAGAA<br>CCAGGTGTCCCTGCAGCTGTCTAGCATGACCACCGAAGATACCGCCG<br>TGTACTACTGCGCCAGAGATGGCGGCTACAGCAGCTCTACCCTGT<br>ACGCCATGGATGCCTGGGGACAGGGAACACTGGTCACAGTGTCTA<br>GCGCCAGCACAACAGCCCCTAGCGTTTTCCCTCTGGCTCCTTCTTGCG<br>GCTCTACCTCTGGATCTACAGTGGCTCTGGCCTGTCTGGTGTCCGGCT<br>ACTTTCCTGAACCTGTGACCGTGTCCTGGAACAGCGGCTCTCTGACA<br>TCTGGCGTGCACACATTCCCTAGCGTGCTGCAGTCTAGCGGCCTGCA<br>CTCTCTGAGCAGCATGGTCACCGTGCCTAGCAGCAGATGGCCCAGCG<br>AAACCCTTCACCTGTAACGTGGTGCACCCCGCCAGCAACACCAAGGTG<br>GACAAGCCTGTGTTCAACGAGTGCAGATGCACCGACACACCTCCATG<br>TCCTGTGCCTGAACCTCTCGGCGGACCTTCCGTGCTGATCTTCCCACC<br>TAAGCCTAAGGACATCCTGAGGATCACCAGGACTCCCGAAGTGACA<br>TGTGTGGTGCTGGACCTGGGCAGAGAAGATCCCGAGGTGCAGATCA<br>GTTGGTTCGTGGACGGCAAAGAGGTGCACACCGCTAAGACCCAGAG<br>CAGAGAGCAGCAGTTCAACGGCACCTACAGAGTGGTGTCCGTGCTG<br>CCTATCGAGCACCAGGATTGGCTGACCGGCAAAGAATTCAAGTGCC<br>GCGTGAACCACATCGACCTGCCTTCTCCAATCGAGAGGACCATCAGC<br>AAGGCCAGAGGCAGGGCCCACAAACCTAGTGTGTATGTGCTGCCTC<br>CATCTCCTAAAGAGCTGAGCAGCTCCGACACCGTGTCCATCACCTGT<br>CTGATCAAGGACTTCTACCCTCCTGACATCGACGTGGAATGGCAGAG<br>CAACGGCCAGCAAGAGCCCGAGAGAAAGCACAGGATGACCCCTCCA<br>CAGCTGGACGAGGACGGCAGCTACTTCCTGTACAGCAAGCTGAGCG<br>TGGACAAGAGCCGATGGCAGCAGGGCGATCCTTTTACCTGTGCCGTG<br>ATGCACGAAACCCTGCAGAACCACTACACCGACCTGTCTCTGAGCCA<br>CTCTCCTGGCTGA (SEQ ID NO: 137) |

Light chain (LC) sequence

| LC | GAGATCGTGATGACCCAGTCTCCTGCCAGCCTGAGCCTGTCTCAAGA<br>GGAAAAAGTGACCATCACCTGTAGGGCCAGCGAGGACATCTACAA<br>TGCCCTGGCCTGGTATCAGCAGAAGCCTGGACAGGCCCCTAAGCTG<br>CTGATCTACAACACCGACACACTGCACACCGGCGTGCCCTCTAGAT<br>TCAGCGGATCTGGCTCTGGCACCGACTACACTTTACAATCAGCAGC<br>CTGGAACCTGAGGACGTGGCCGTGTACTTCTGCCAGCACTACTTTC<br>ACTACCCCAGAACCTTCGGAGCCGGCACCAAGGTGGAACTGAAGA<br>GGAATGATGCCCAGCCTGCCGTGTACCTGTTCCAGCCTTCTCCAGAT<br>CAGCTGCACACAGGCTCTGCCAGCGTTGTGTGCCTGCTGAACAGCTT<br>CTACCCCAAGGACATCAACGTGAAGTGGAAGGTGGACGGCGTGATC<br>CAGGACACCGGCATCCAAGAGTCTGTGACCGAGCAGGACAAGGACA<br>GCACCTACAGCCTGTCTAGCACCCTGACCATGAGCAGCACCGAGTAC<br>CTGAGCCACGAGCTGTACTCTTGCGAGATCACCCACAAGAGCCTGCC<br>TTCCACACTGATCAAGAGCTTCCAGCGGAGCGAGTGCCAGAGAGTG<br>GATTGA (SEQ ID NO: 138) |

The invention claimed is:

1. An antibody or an antigen-binding fragment thereof that specifically binds to nerve growth factor (NGF), wherein the antibody or an antigen-binding fragment thereof comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO: 1, a VH CDR2 comprising the amino acid sequence of SEQ ID NO: 2 and a VH CDR3 comprising the amino acid sequence of SEQ ID NO: 3; and wherein the VL comprises a complementarity determining region 1 (VL CDR1) comprising the amino acid sequence of SEQ ID NO: 4, a VL CDR2 comprising the amino acid sequence of SEQ ID NO: 5, and a VL CDR3 comprising the amino acid sequence of SEQ ID NO: 6.

2. The anti-NGF antibody or antigen-binding fragment thereof of claim 1, wherein the anti-NGF antibody or antigen-binding fragment thereof is:

i. an anti-NGF-antigen binding fragment thereof selected from the group consisting of a Fab fragment, an scFab, a Fab', a single chain variable fragment (scFv), and a one-armed antibody; or ii. a humanized, caninized, felinized or equinized anti-NGF antibody or antigen-binding fragment thereof.

3. A pharmaceutical composition comprising the anti-NGF antibody or antigen-binding fragment thereof of claim 1, and a pharmaceutically acceptable carrier.

4. The anti-NGF antibody or antigen-binding fragment thereof of claim 1 wherein the antibody or antigen-binding fragment comprises: (a) a VH comprising the amino acid sequence of SEQ ID NO: 12 and, (b) a VL comprising the amino acid sequence of SEQ ID NO: 128.

* * * * *

SEQUENCE LISTING

```
Sequence total quantity: 138
SEQ ID NO: 1                moltype = AA  length = 10
FEATURE                     Location/Qualifiers
source                      1..10
                            mol_type = protein
                            organism = synthetic construct
SEQUENCE: 1
GFSLTNNNVN                                                                    10

SEQ ID NO: 2                moltype = AA  length = 16
FEATURE                     Location/Qualifiers
source                      1..16
                            mol_type = protein
                            organism = synthetic construct
SEQUENCE: 2
GVWAGGATDY NSAVKS                                                             16

SEQ ID NO: 3                moltype = AA  length = 14
FEATURE                     Location/Qualifiers
source                      1..14
                            mol_type = protein
                            organism = synthetic construct
SEQUENCE: 3
DGGYSSSTLY AMDA                                                               14

SEQ ID NO: 4                moltype = AA  length = 11
FEATURE                     Location/Qualifiers
source                      1..11
                            mol_type = protein
                            organism = synthetic construct
SEQUENCE: 4
RASEDIYNAL A                                                                  11

SEQ ID NO: 5                moltype = AA  length = 7
FEATURE                     Location/Qualifiers
source                      1..7
                            mol_type = protein
                            organism = synthetic construct
SEQUENCE: 5
NTDTLHT                                                                       7

SEQ ID NO: 6                moltype = AA  length = 9
FEATURE                     Location/Qualifiers
source                      1..9
                            mol_type = protein
                            organism = synthetic construct
SEQUENCE: 6
QHYFHYPRT                                                                     9

SEQ ID NO: 7                moltype = AA  length = 10
FEATURE                     Location/Qualifiers
source                      1..10
                            mol_type = protein
                            organism = synthetic construct
SEQUENCE: 7
GLSLTNNNVN                                                                    10

SEQ ID NO: 8                moltype = AA  length = 16
FEATURE                     Location/Qualifiers
source                      1..16
                            mol_type = protein
                            organism = synthetic construct
SEQUENCE: 8
GVWAGGATDY NSALKS                                                             16

SEQ ID NO: 9                moltype = AA  length = 122
FEATURE                     Location/Qualifiers
source                      1..122
                            mol_type = protein
                            organism = synthetic construct
SEQUENCE: 9
QVQLVESGAE LVQPGESLRL TCAASGFSLT NNNVNWVRQA PGKGLEWMGG VWAGGATDYN             60
SALKSRLTIT RDTSKNTVFL QMHSLQSEDT ATYYCARDGG YSSSTLYAMD AWGQGTTVTV            120
SA                                                                          122

SEQ ID NO: 10               moltype = AA  length = 107
FEATURE                     Location/Qualifiers
source                      1..107
```

```
                              mol_type = protein
                              organism = synthetic construct
SEQUENCE: 10
DIEMTQSPLS LSVTPGESVS ISCRASEDIY NALAWYLQKP GRSPRLLIYN TDTLHTGVPD    60
RFSGSGSGTD FTLKISRVQT EDVGVYFCQH YFHYPRTFGQ GTKLELK                 107

SEQ ID NO: 11              moltype = AA   length = 122
FEATURE                    Location/Qualifiers
source                     1..122
                           mol_type = protein
                           organism = synthetic construct
SEQUENCE: 11
QVQLMESGAD LVQPSESLRL TCVASGLSLT NNNVNWVRQA PGKGLEWMGG VWAGGATDYN    60
SALKSRLTIT RDTSKNTVFL QMHSLQSEDT ATYYCARDGG YSSSTLYAMD AWGQGTTVTV   120
SA                                                                 122

SEQ ID NO: 12              moltype = AA   length = 122
FEATURE                    Location/Qualifiers
source                     1..122
                           mol_type = protein
                           organism = synthetic construct
SEQUENCE: 12
QVQLVESGGD LVQPGGSLRL TCVASGFSLT NNNVNWVRQA PGKGLEWMGG VWAGGATDYN    60
SAVKSRLTIT RDTSKNTVFL QMHSLQSEDT ATYYCARDGG YSSSTLYAMD AWGQGTTVTV   120
SA                                                                 122

SEQ ID NO: 13              moltype = AA   length = 25
FEATURE                    Location/Qualifiers
source                     1..25
                           mol_type = protein
                           organism = synthetic construct
SEQUENCE: 13
QVQLMESGAD LVQPSESLRL TCVAS                                         25

SEQ ID NO: 14              moltype = AA   length = 14
FEATURE                    Location/Qualifiers
source                     1..14
                           mol_type = protein
                           organism = synthetic construct
SEQUENCE: 14
WVRQAPGKGL EWMG                                                     14

SEQ ID NO: 15              moltype = AA   length = 32
FEATURE                    Location/Qualifiers
source                     1..32
                           mol_type = protein
                           organism = synthetic construct
SEQUENCE: 15
RLTITRDTSK NTVFLQMHSL QSEDTATYYC AR                                 32

SEQ ID NO: 16              moltype = AA   length = 11
FEATURE                    Location/Qualifiers
source                     1..11
                           mol_type = protein
                           organism = synthetic construct
SEQUENCE: 16
WGQGTTVTVS A                                                        11

SEQ ID NO: 17              moltype = AA   length = 23
FEATURE                    Location/Qualifiers
source                     1..23
                           mol_type = protein
                           organism = synthetic construct
SEQUENCE: 17
DIEMTQSPLS LSVTPGESVS ISC                                           23

SEQ ID NO: 18              moltype = AA   length = 15
FEATURE                    Location/Qualifiers
source                     1..15
                           mol_type = protein
                           organism = synthetic construct
SEQUENCE: 18
WYLQKPGRSP RLLIY                                                    15

SEQ ID NO: 19              moltype = AA   length = 32
FEATURE                    Location/Qualifiers
source                     1..32
                           mol_type = protein
                           organism = synthetic construct
```

```
SEQUENCE: 19
GVPDRFSGSG SGTDFTLKIS RVQTEDVGVY FC                                    32

SEQ ID NO: 20          moltype = AA  length = 10
FEATURE                Location/Qualifiers
source                 1..10
                       mol_type = protein
                       organism = synthetic construct
SEQUENCE: 20
FGQGTKLELK                                                             10

SEQ ID NO: 21          moltype = AA  length = 476
FEATURE                Location/Qualifiers
source                 1..476
                       mol_type = protein
                       organism = synthetic construct
SEQUENCE: 21
MEWSWVFLFF LSVTTGVHSQ VQLVESGAEL VQPGESLRLT CAASGFSLTN NNVNWVRQAP      60
GKGLEWMGGV WAGGATDYNS ALKSRLTITR DTSKNTVFLQ MHSLQSEDTA TYYCARDGGY     120
SSSSTLYAMDA WGQGTTVTVS AASTTAPSVF PLAPSCGTTS GATVALACLV LGYFPEPVTV    180
SWNSGALTSG VHTFPAVLQA SGLYSLSSMV TVPSSRWLSD TFTCNVAHPP SNTKVDKTVR     240
KTDHPPGPKP CDCPKCPPPE MLGGPSIFIF PPKPKDTLSI SRTPEVTCLV VDLGPDDSDV     300
QITWFVDNTQ VYTAKTSPRE EQFNSTYRVV SVLPILHQDW LKGKEFKCKV NSKSLPSPIE     360
RTISKAKGQP HEPQVYVLPP AQEELSRNKV SVTCLIKSFH PPDIAVEWEI TGQPEPENNY     420
RTTPPQLDSD GTYFVYSKLS VDRSHWQRGN TYTCSVSHEA LHSHHTQKSL TQSPGK         476

SEQ ID NO: 22          moltype = AA  length = 237
FEATURE                Location/Qualifiers
source                 1..237
                       mol_type = protein
                       organism = synthetic construct
SEQUENCE: 22
MSVPTQVLGL LLLWLTDARC DIEMTQSPLS LSVTPGESVS ISCRASEDIY NALAWYLQKP      60
GRSPRLLIYN TDTLHTGVPD RFSGSGSGTD FTLKISRVQT EDVGVYFCQH YPHYPRTFGQ    120
GTKLELKRSD AQPSVFLFQP SLDELHTGSA SIVCILNDFY PKEVNVKWKV DGVVQNKGIQ    180
ESTTEQNSKD STYSLSSTLT MSSTEYQSHE KFSCEVTHKS LASTLVKSFN RSECQRE       237

SEQ ID NO: 23          moltype = AA  length = 476
FEATURE                Location/Qualifiers
source                 1..476
                       mol_type = protein
                       organism = synthetic construct
SEQUENCE: 23
MEWSWVFLFF LSVTTGVHSQ VQLMESGADL VQPSESLRLT CVASGLSLTN NNVNWVRQAP      60
GKGLEWMGGV WAGGATDYNS ALKSRLTITR DTSKNTVFLQ MHSLQSEDTA TYYCARDGGY    120
SSSSTLYAMDA WGQGTTVTVS AASTTAPSVF PLAPSCGTTS GATVALACLV LGYFPEPVTV   180
SWNSGALTSG VHTFPAVLQA SGLYSLSSMV TVPSSRWLSD TFTCNVAHPP SNTKVDKTVR    240
KTDHPPGPKP CDCPKCPPPE MLGGPSIFIF PPKPKDTLSI SRTPEVTCLV VDLGPDDSDV    300
QITWFVDNTQ VYTAKTSPRE EQFNSTYRVV SVLPILHQDW LKGKEFKCKV NSKSLPSPIE    360
RTISKAKGQP HEPQVYVLPP AQEELSRNKV SVTCLIKSFH PPDIAVEWEI TGQPEPENNY    420
RTTPPQLDSD GTYFVYSKLS VDRSHWQRGN TYTCSVSHEA LHSHHTQKSL TQSPGK        476

SEQ ID NO: 24          moltype = AA  length = 476
FEATURE                Location/Qualifiers
source                 1..476
                       mol_type = protein
                       organism = synthetic construct
SEQUENCE: 24
MEWSWVFLFF LSVTTGVHSQ VQLVESGGDL VQPGGSLRLT CVASGFSLTN NNVNWVRQAP      60
GKGLEWMGGV WAGGATDYNS AVKSRLTITR DTSKNTVFLQ MHSLQSEDTA TYYCARDGGY    120
SSSSTLYAMDA WGQGTTVTVS AASTTAPSVF PLAPSCGTTS GATVALACLV LGYFPEPVTV   180
SWNSGALTSG VHTFPAVLQA SGLYSLSSMV TVPSSRWLSD TFTCNVAHPP SNTKVDKTVR    240
KTDHPPGPKP CDCPKCPPPE MLGGPSIFIF PPKPKDTLSI SRTPEVTCLV VDLGPDDSDV    300
QITWFVDNTQ VYTAKTSPRE EQFNSTYRVV SVLPILHQDW LKGKEFKCKV NSKSLPSPIE    360
RTISKAKGQP HEPQVYVLPP AQEELSRNKV SVTCLIKSFH PPDIAVEWEI TGQPEPENNY    420
RTTPPQLDSD GTYFVYSKLS VDRSHWQRGN TYTCSVSHEA LHSHHTQKSL TQSPGK        476

SEQ ID NO: 25          moltype = DNA  length = 1428
FEATURE                Location/Qualifiers
source                 1..1428
                       mol_type = other DNA
                       organism = Felis catus
SEQUENCE: 25
atggaatggt cttgggtgtt cctgttcttc ctgtccgtga ccaccggcgt gcactctcag      60
gttcagctgg ttgaatctgg cggcgacctt gttcagcctg gcggatctct gagactgacc    120
tgtgtggcct ctggcttctc cctgaccaac aacaacgtga actgggtccg acaggccct     180
ggcaaaggac tggaatggat gggcggagtt tgggctggcg cgctaccga ttacaactcc     240
gccgtgaagt cccggctgac catcaccaga gacacctcca agaacaccgt gtttctgcag    300
atgcactccc tgcagtctga ggacaccgcc acctactact gtgctagaga tggcggctac    360
```

```
tccagcagca ccctgtacgc tatggatgct tggggccagg gcaccaccgt gacagtttct    420
gccgcttcta ccaccgctcc tagcgtgttc cctctggctc cttcttgtgg caccaccctct   480
ggtgctacag tggctctggc atgtctggtg ctgggctact ttcctgagcc tgtgaccgtg    540
tcctggaact ctggcgctct gacatctggc gtgcacacct ttccagctgt gctgcaggct    600
tccggcctgt actctctgtc ctctatggtc accgtgcctc ccagcagatg gctgtccgac    660
accttcacct gtaacgtggc ccatcctcct agcaacacca aggtggacaa gaccgtgcgc    720
aagaccgatc atcctcctgg acctaagcct tgcgactgcc ctaagtgtcc tccacctgag    780
atgctcggcg gacccagcat cttcatcttc ccacctaagc caaaggacac cctgtccatc    840
tctcggaccc ctgaagtgac ctgcctggtg gtttgatctgg gcctgaacga ctctgacgtg    900
cagatcactt ggtttgtgga caacacccag gtgtacacga ccaagacctc tccaagagag    960
gaacagttca actccaccta cagagtggtg tccgtgctgc ccatcctgca ccaggattgg   1020
ctgaagggca agaattcaa gtgcaaagtg aactccaaga gcctgccttc tccaatcgag   1080
cggaccatct ccaaggctaa gggccagcct catgagcctc aggtctacgt tctgcctcct   1140
gctcaagagg aactgtcccg gaacaaagtg tctgtgactt gtctgatcaa gagctttcac   1200
cctcctgata tcgccgtgga atgggagatc accggacagc tgagccagaa gaacaactac   1260
cggaccacac tcctcagct ggactccgat ggcacctact tcgtgtactc caagctgtcc   1320
gtggacagat cccactggca gcggggcaat acctacacct gttccgtgtc tcacgaggcc   1380
ctgcactccc atcacaccca gaagtccctg actcagagcc ccggcaag              1428

SEQ ID NO: 26          moltype = DNA   length = 711
FEATURE                Location/Qualifiers
source                 1..711
                       mol_type = other DNA
                       organism = Felis catus
SEQUENCE: 26
atgtctgtgc ctacacaggt tctgggactg ctgctgctgt ggctgaccga cgccagatgc    60
gacatcgaga tgacccagtc tccactgagc ctgtctgcta ccctggcga gacagtgtcc   120
atctcctgta gagcctccga ggacatctac aacgccctgg cctggtatct gcagaagcct   180
ggcagatccc ctcggctgct gatctacaac accgacacac tgcataccgg cgtgcccgac   240
agattttccg gctctggctc tggcaccgac ttcaccctga gatttctcg ggtgcagacc   300
gaggacgtgg gcgtgtactt ttgccagcac tactttcact accctcggac ctttggccag   360
ggcaccaagc tggaactgaa agatccgac gctcagccct ccgtgttcct gttccagcct   420
tctctggatg agctgcacac cggctccgcc tctatcgtgt gcatcctgaa cgacttctac   480
cccaaagaag tgaacgtgaa gtggaaggtg gacggcgtgg tgcagaacaa gggcatccaa   540
gagtctacca ccgagcagaa ctccaaggac tccacctaca gcctgagcag caccctgacc   600
atgtcctcca ccgagtacca gagccacgag aagttcagct gcgaagtgac ccacaagtcc   660
ctggcttcta ccctggtcaa gtccttcaac agatccgagt gccagcgcga g           711

SEQ ID NO: 27          moltype = AA   length = 122
FEATURE                Location/Qualifiers
source                 1..122
                       mol_type = protein
                       organism = synthetic construct
SEQUENCE: 27
QVQLQESGPG LVKPSQTLSL TCTVSGFSLT NNNVNWVRQR TGRGLEWMGG VWAGGATDYN    60
SAVKSRLSIT RDTAKSQVSL QMSSMTTEDT ATYYCARDGG YSSSTLYAMD AWGQGTSVTV   120
SS                                                                 122

SEQ ID NO: 28          moltype = AA   length = 122
FEATURE                Location/Qualifiers
source                 1..122
                       mol_type = protein
                       organism = synthetic construct
SEQUENCE: 28
QVQLQESGPG LVKPSQTLSL TCTVSGFSLT NNNVNWVRQR PGRGLEWMGG VWAGGATDYN    60
SAVKSRLSIT RDTAKSQVSL QMSSMTTEDT ATYYCARDGG YSSSTLYAMD AWGQGTLVTV   120
SS                                                                 122

SEQ ID NO: 29          moltype = AA   length = 122
FEATURE                Location/Qualifiers
source                 1..122
                       mol_type = protein
                       organism = synthetic construct
SEQUENCE: 29
QVQLQESGPG LVKPSQTLSL TCTVSGFSLT NNNVNWVRQR PGRGLEWMGG VWAGGATDYN    60
SAVKSRISIT RDTAKSQVSL QLSSMTTEDT ATYYCARDGG YSSSTLYAMD AWGQGTLVTV   120
SS                                                                 122

SEQ ID NO: 30          moltype = AA   length = 122
FEATURE                Location/Qualifiers
source                 1..122
                       mol_type = protein
                       organism = synthetic construct
SEQUENCE: 30
EVTLQESGPG LVKPSQTLSL TCTVSGFSLT NNNVNWVRQR PGRGLEWMGG VWAGGATDYN    60
SAVKSRISIT RDTAKNQVSL QLSSMTTEDT ATYYCARDGG YSSSTLYAMD AWGQGTLVTV   120
SS                                                                 122

SEQ ID NO: 31          moltype = AA   length = 122
```

```
FEATURE                 Location/Qualifiers
source                  1..122
                        mol_type = protein
                        organism = synthetic construct
SEQUENCE: 31
EVTLQESGPG LVKPSQTLSL TCVVSGFSLT NNNVNWVRQR PGRGLEWMGG VWAGGATDYN      60
SAVKSRISIT RDTAKNQVSL QLSSMTTEDT AVYYCARDGG YSSSTLYAMD AWGQGTLVTV     120
SS                                                                    122

SEQ ID NO: 32           moltype = AA   length = 107
FEATURE                 Location/Qualifiers
source                  1..107
                        mol_type = protein
                        organism = synthetic construct
SEQUENCE: 32
DIQMTQSPAS LSLSQEEKVT ITCRASEDIY NALAWYQQKP GQAPKLLIYN TDTLHTGVPS      60
RFSGSGSGTD YSFTISSLES EDVASYFCQH YFHYPRTFGA GTKVELK                  107

SEQ ID NO: 33           moltype = AA   length = 107
FEATURE                 Location/Qualifiers
source                  1..107
                        mol_type = protein
                        organism = synthetic construct
SEQUENCE: 33
DIQMTQSPAS LSLSQEEKVT ITCRASEDIY NALAWYQQKP GQAPKLLIYN TDTLHTGVPS      60
RFSGSGSGTD YSFTISSLEP EDVASYFCQH YFHYPRTFGA GTKVELK                  107

SEQ ID NO: 34           moltype = AA   length = 107
FEATURE                 Location/Qualifiers
source                  1..107
                        mol_type = protein
                        organism = synthetic construct
SEQUENCE: 34
EIVMTQSPAS LSLSQEEKVT ITCRASEDIY NALAWYQQKP GQAPKLLIYN TDTLHTGVPS      60
RFSGSGSGTD YSFTISSLEP EDVAVYFCQH YFHYPRTFGA GTKVELK                  107

SEQ ID NO: 35           moltype = AA   length = 107
FEATURE                 Location/Qualifiers
source                  1..107
                        mol_type = protein
                        organism = synthetic construct
SEQUENCE: 35
EIVMTQSPAS LSLSQEEKVT ITCRASEDIY NALAWYQQKP GQAPKLLIYN TDTLHTGVPS      60
RFSGSGSGTD YSFTISSLEP EDVAVYFCQH YFHYPRTFGA GTKVELK                  107

SEQ ID NO: 36           moltype = AA   length = 25
FEATURE                 Location/Qualifiers
source                  1..25
                        mol_type = protein
                        organism = synthetic construct
SEQUENCE: 36
QVQLQESGPG LVKPSQTLSL TCTVS                                            25

SEQ ID NO: 37           moltype = AA   length = 14
FEATURE                 Location/Qualifiers
source                  1..14
                        mol_type = protein
                        organism = synthetic construct
SEQUENCE: 37
WVRQRTGRGL EWMG                                                        14

SEQ ID NO: 38           moltype = AA   length = 32
FEATURE                 Location/Qualifiers
source                  1..32
                        mol_type = protein
                        organism = synthetic construct
SEQUENCE: 38
RLSITRDTAK SQVSLQMSSM TTEDTATYYC AR                                    32

SEQ ID NO: 39           moltype = AA   length = 11
FEATURE                 Location/Qualifiers
source                  1..11
                        mol_type = protein
                        organism = synthetic construct
SEQUENCE: 39
WGQGTSVTVS S                                                           11

SEQ ID NO: 40           moltype = AA   length = 25
FEATURE                 Location/Qualifiers
```

```
source                  1..25
                        mol_type = protein
                        organism = synthetic construct
SEQUENCE: 40
QVQLQESGPG LVKPSQTLSL TCTVS                                        25

SEQ ID NO: 41           moltype = AA   length = 14
FEATURE                 Location/Qualifiers
source                  1..14
                        mol_type = protein
                        organism = synthetic construct
SEQUENCE: 41
WVRQRPGRGL EWMG                                                    14

SEQ ID NO: 42           moltype = AA   length = 32
FEATURE                 Location/Qualifiers
source                  1..32
                        mol_type = protein
                        organism = synthetic construct
SEQUENCE: 42
RLSITRDTAK SQVSLQMSSM TTEDTATYYC AR                                32

SEQ ID NO: 43           moltype = AA   length = 11
FEATURE                 Location/Qualifiers
source                  1..11
                        mol_type = protein
                        organism = synthetic construct
SEQUENCE: 43
WGQGTLVTVS S                                                       11

SEQ ID NO: 44           moltype = AA   length = 25
FEATURE                 Location/Qualifiers
source                  1..25
                        mol_type = protein
                        organism = synthetic construct
SEQUENCE: 44
QVQLQESGPG LVKPSQTLSL TCTVS                                        25

SEQ ID NO: 45           moltype = AA   length = 14
FEATURE                 Location/Qualifiers
source                  1..14
                        mol_type = protein
                        organism = synthetic construct
SEQUENCE: 45
WVRQRPGRGL EWMG                                                    14

SEQ ID NO: 46           moltype = AA   length = 32
FEATURE                 Location/Qualifiers
source                  1..32
                        mol_type = protein
                        organism = synthetic construct
SEQUENCE: 46
RISITRDTAK SQVSLQLSSM TTEDTATYYC AR                                32

SEQ ID NO: 47           moltype = AA   length = 11
FEATURE                 Location/Qualifiers
source                  1..11
                        mol_type = protein
                        organism = synthetic construct
SEQUENCE: 47
WGQGTLVTVS S                                                       11

SEQ ID NO: 48           moltype = AA   length = 25
FEATURE                 Location/Qualifiers
source                  1..25
                        mol_type = protein
                        organism = synthetic construct
SEQUENCE: 48
EVTLQESGPG LVKPSQTLSL TCTVS                                        25

SEQ ID NO: 49           moltype = AA   length = 14
FEATURE                 Location/Qualifiers
source                  1..14
                        mol_type = protein
                        organism = synthetic construct
SEQUENCE: 49
WVRQRPGRGL EWMG                                                    14

SEQ ID NO: 50           moltype = AA   length = 32
```

```
FEATURE           Location/Qualifiers
source            1..32
                  mol_type = protein
                  organism = synthetic construct
SEQUENCE: 50
RISITRDTAK NQVSLQLSSM TTEDTATYYC AR                              32

SEQ ID NO: 51     moltype = AA  length = 11
FEATURE           Location/Qualifiers
source            1..11
                  mol_type = protein
                  organism = synthetic construct
SEQUENCE: 51
WGQGTLVTVS S                                                     11

SEQ ID NO: 52     moltype = AA  length = 25
FEATURE           Location/Qualifiers
source            1..25
                  mol_type = protein
                  organism = synthetic construct
SEQUENCE: 52
EVTLQESGPG LVKPSQTLSL TCVVS                                      25

SEQ ID NO: 53     moltype = AA  length = 14
FEATURE           Location/Qualifiers
source            1..14
                  mol_type = protein
                  organism = synthetic construct
SEQUENCE: 53
WVRQRPGRGL EWMG                                                  14

SEQ ID NO: 54     moltype = AA  length = 32
FEATURE           Location/Qualifiers
source            1..32
                  mol_type = protein
                  organism = synthetic construct
SEQUENCE: 54
RISITRDTAK NQVSLQLSSM TTEDTAVYYC AR                              32

SEQ ID NO: 55     moltype = AA  length = 11
FEATURE           Location/Qualifiers
source            1..11
                  mol_type = protein
                  organism = synthetic construct
SEQUENCE: 55
WGQGTLVTVS S                                                     11

SEQ ID NO: 56     moltype = AA  length = 23
FEATURE           Location/Qualifiers
source            1..23
                  mol_type = protein
                  organism = synthetic construct
SEQUENCE: 56
DIQMTQSPAS LSLSQEEKVT ITC                                        23

SEQ ID NO: 57     moltype = AA  length = 15
FEATURE           Location/Qualifiers
source            1..15
                  mol_type = protein
                  organism = synthetic construct
SEQUENCE: 57
WYQQKPGQAP KLLIY                                                 15

SEQ ID NO: 58     moltype = AA  length = 32
FEATURE           Location/Qualifiers
source            1..32
                  mol_type = protein
                  organism = synthetic construct
SEQUENCE: 58
GVPSRFSGSG SGTDYSFTIS SLESEDVASY FC                              32

SEQ ID NO: 59     moltype = AA  length = 10
FEATURE           Location/Qualifiers
source            1..10
                  mol_type = protein
                  organism = synthetic construct
SEQUENCE: 59
FGAGTKVELK                                                       10
```

```
SEQ ID NO: 60              moltype = AA   length = 23
FEATURE                    Location/Qualifiers
source                     1..23
                           mol_type = protein
                           organism = synthetic construct
SEQUENCE: 60
DIQMTQSPAS LSLSQEEKVT ITC                                                  23

SEQ ID NO: 61              moltype = AA   length = 15
FEATURE                    Location/Qualifiers
source                     1..15
                           mol_type = protein
                           organism = synthetic construct
SEQUENCE: 61
WYQQKPGQAP KLLIY                                                           15

SEQ ID NO: 62              moltype = AA   length = 10
FEATURE                    Location/Qualifiers
source                     1..10
                           mol_type = protein
                           organism = synthetic construct
SEQUENCE: 62
FGAGTKVELK                                                                 10

SEQ ID NO: 63              moltype = AA   length = 10
FEATURE                    Location/Qualifiers
source                     1..10
                           mol_type = protein
                           organism = synthetic construct
SEQUENCE: 63
FGAGTKVELK                                                                 10

SEQ ID NO: 64              moltype = AA   length = 15
FEATURE                    Location/Qualifiers
source                     1..15
                           mol_type = protein
                           organism = synthetic construct
SEQUENCE: 64
WYQQKPGQAP KLLIY                                                           15

SEQ ID NO: 65              moltype = AA   length = 15
FEATURE                    Location/Qualifiers
source                     1..15
                           mol_type = protein
                           organism = synthetic construct
SEQUENCE: 65
WYQQKPGQAP KLLIY                                                           15

SEQ ID NO: 66              moltype = AA   length = 32
FEATURE                    Location/Qualifiers
source                     1..32
                           mol_type = protein
                           organism = synthetic construct
SEQUENCE: 66
GVPSRFSGSG SGTDYSFTIS SLEPEDVASY FC                                        32

SEQ ID NO: 67              moltype = AA   length = 10
FEATURE                    Location/Qualifiers
source                     1..10
                           mol_type = protein
                           organism = synthetic construct
SEQUENCE: 67
FGAGTKVELK                                                                 10

SEQ ID NO: 68              moltype = AA   length = 23
FEATURE                    Location/Qualifiers
source                     1..23
                           mol_type = protein
                           organism = synthetic construct
SEQUENCE: 68
EIVMTQSPAS LSLSQEEKVT ITC                                                  23

SEQ ID NO: 69              moltype = AA   length = 15
FEATURE                    Location/Qualifiers
source                     1..15
                           mol_type = protein
                           organism = synthetic construct
SEQUENCE: 69
WYQQKPGQAP KLLIY                                                           15
```

| SEQ ID NO: 70 | moltype = AA  length = 32 |
| FEATURE | Location/Qualifiers |
| source | 1..32 |
| | mol_type = protein |
| | organism = synthetic construct |

SEQUENCE: 70
GVPSRFSGSG SGTDYSFTIS SLEPEDVAVY FC                              32

| SEQ ID NO: 71 | moltype = AA  length = 10 |
| FEATURE | Location/Qualifiers |
| source | 1..10 |
| | mol_type = protein |
| | organism = synthetic construct |

SEQUENCE: 71
FGAGTKVELK                                                       10

| SEQ ID NO: 72 | moltype = AA  length = 26 |
| FEATURE | Location/Qualifiers |
| source | 1..26 |
| | mol_type = protein |
| | organism = synthetic construct |

SEQUENCE: 72
GQVQLVESGG DLVQPGGSLR LTCVAS                                     26

| SEQ ID NO: 73 | moltype = AA  length = 27 |
| FEATURE | Location/Qualifiers |
| source | 1..27 |
| | mol_type = protein |
| | organism = synthetic construct |

SEQUENCE: 73
SSQVQLVESG AELVQPGESL RLTCAAS                                    27

| SEQ ID NO: 74 | moltype = AA  length = 25 |
| FEATURE | Location/Qualifiers |
| source | 1..25 |
| | mol_type = protein |
| | organism = synthetic construct |

SEQUENCE: 74
QVQLXESGXX LVQPXXSLRL TCXAS                                      25

| SEQ ID NO: 75 | moltype = AA  length = 25 |
| FEATURE | Location/Qualifiers |
| source | 1..25 |
| | mol_type = protein |
| | organism = synthetic construct |

SEQUENCE: 75
QVQLVESGAD LVQPSESLRL TCVAS                                      25

| SEQ ID NO: 76 | moltype = AA  length = 25 |
| FEATURE | Location/Qualifiers |
| source | 1..25 |
| | mol_type = protein |
| | organism = synthetic construct |

SEQUENCE: 76
QVQLVESGGD LVQPSESLRL TCVAS                                      25

| SEQ ID NO: 77 | moltype = AA  length = 25 |
| FEATURE | Location/Qualifiers |
| source | 1..25 |
| | mol_type = protein |
| | organism = synthetic construct |

SEQUENCE: 77
QVQLVESGAD LVQPGESLRL TCVAS                                      25

| SEQ ID NO: 78 | moltype = AA  length = 25 |
| FEATURE | Location/Qualifiers |
| source | 1..25 |
| | mol_type = protein |
| | organism = synthetic construct |

SEQUENCE: 78
QVQLVESGAD LVQPSGSLRL TCVAS                                      25

| SEQ ID NO: 79 | moltype = AA  length = 25 |
| FEATURE | Location/Qualifiers |
| source | 1..25 |
| | mol_type = protein |
| | organism = synthetic construct |

SEQUENCE: 79

QVQLVESGGD LVQPGESLRL TCVAS                                                    25

SEQ ID NO: 80           moltype = AA  length = 25
FEATURE                 Location/Qualifiers
source                  1..25
                        mol_type = protein
                        organism = synthetic construct
SEQUENCE: 80
QVQLVESGGD LVQPSGSLRL TCVAS                                                    25

SEQ ID NO: 81           moltype = AA  length = 25
FEATURE                 Location/Qualifiers
source                  1..25
                        mol_type = protein
                        organism = synthetic construct
SEQUENCE: 81
QVQLMESGGD LVQPSESLRL TCVAS                                                    25

SEQ ID NO: 82           moltype = AA  length = 25
FEATURE                 Location/Qualifiers
source                  1..25
                        mol_type = protein
                        organism = synthetic construct
SEQUENCE: 82
QVQLMESGAD LVQPGESLRL TCVAS                                                    25

SEQ ID NO: 83           moltype = AA  length = 25
FEATURE                 Location/Qualifiers
source                  1..25
                        mol_type = protein
                        organism = synthetic construct
SEQUENCE: 83
QVQLMESGAD LVQPSGSLRL TCVAS                                                    25

SEQ ID NO: 84           moltype = AA  length = 25
FEATURE                 Location/Qualifiers
source                  1..25
                        mol_type = protein
                        organism = synthetic construct
SEQUENCE: 84
QVQLMESGGD LVQPGESLRL TCVAS                                                    25

SEQ ID NO: 85           moltype = AA  length = 25
FEATURE                 Location/Qualifiers
source                  1..25
                        mol_type = protein
                        organism = synthetic construct
SEQUENCE: 85
QVQLMESGGD LVQPSGSLRL TCVAS                                                    25

SEQ ID NO: 86           moltype = AA  length = 25
FEATURE                 Location/Qualifiers
source                  1..25
                        mol_type = protein
                        organism = synthetic construct
SEQUENCE: 86
QVQLMESGGD LVQPGGSLRL TCVAS                                                    25

SEQ ID NO: 87           moltype = AA  length = 25
FEATURE                 Location/Qualifiers
source                  1..25
                        mol_type = protein
                        organism = synthetic construct
SEQUENCE: 87
QVQLVESGAD LVQPSESLRL TCAAS                                                    25

SEQ ID NO: 88           moltype = AA  length = 25
FEATURE                 Location/Qualifiers
source                  1..25
                        mol_type = protein
                        organism = synthetic construct
SEQUENCE: 88
QVQLVESGGD LVQPSESLRL TCAAS                                                    25

SEQ ID NO: 89           moltype = AA  length = 25
FEATURE                 Location/Qualifiers
source                  1..25
                        mol_type = protein
                        organism = synthetic construct

```
SEQUENCE: 89
QVQLVESGAD LVQPGESLRL TCAAS                                              25

SEQ ID NO: 90          moltype = AA  length = 25
FEATURE                Location/Qualifiers
source                 1..25
                       mol_type = protein
                       organism = synthetic construct
SEQUENCE: 90
QVQLVESGAD LVQPSGSLRL TCAAS                                              25

SEQ ID NO: 91          moltype = AA  length = 25
FEATURE                Location/Qualifiers
source                 1..25
                       mol_type = protein
                       organism = synthetic construct
SEQUENCE: 91
QVQLVESGGD LVQPGESLRL TCAAS                                              25

SEQ ID NO: 92          moltype = AA  length = 25
FEATURE                Location/Qualifiers
source                 1..25
                       mol_type = protein
                       organism = synthetic construct
SEQUENCE: 92
QVQLVESGGD LVQPSGSLRL TCAAS                                              25

SEQ ID NO: 93          moltype = AA  length = 25
FEATURE                Location/Qualifiers
source                 1..25
                       mol_type = protein
                       organism = synthetic construct
SEQUENCE: 93
QVQLVESGGD LVQPGGSLRL TCAAS                                              25

SEQ ID NO: 94          moltype = AA  length = 25
FEATURE                Location/Qualifiers
source                 1..25
                       mol_type = protein
                       organism = synthetic construct
SEQUENCE: 94
QVQLMESGAD LVQPSESLRL TCAAS                                              25

SEQ ID NO: 95          moltype = AA  length = 25
FEATURE                Location/Qualifiers
source                 1..25
                       mol_type = protein
                       organism = synthetic construct
SEQUENCE: 95
QVQLMESGGD LVQPSESLRL TCAAS                                              25

SEQ ID NO: 96          moltype = AA  length = 25
FEATURE                Location/Qualifiers
source                 1..25
                       mol_type = protein
                       organism = synthetic construct
SEQUENCE: 96
QVQLMESGAD LVQPGESLRL TCAAS                                              25

SEQ ID NO: 97          moltype = AA  length = 25
FEATURE                Location/Qualifiers
source                 1..25
                       mol_type = protein
                       organism = synthetic construct
SEQUENCE: 97
QVQLMESGAD LVQPSGSLRL TCAAS                                              25

SEQ ID NO: 98          moltype = AA  length = 25
FEATURE                Location/Qualifiers
source                 1..25
                       mol_type = protein
                       organism = synthetic construct
SEQUENCE: 98
QVQLMESGGD LVQPGESLRL TCAAS                                              25

SEQ ID NO: 99          moltype = AA  length = 25
FEATURE                Location/Qualifiers
source                 1..25
                       mol_type = protein
```

```
                    organism = synthetic construct
SEQUENCE: 99
QVQLMESGGD LVQPSGSLRL TCAAS                                           25

SEQ ID NO: 100          moltype = AA   length = 25
FEATURE                 Location/Qualifiers
source                  1..25
                        mol_type = protein
                        organism = synthetic construct
SEQUENCE: 100
QVQLMESGGD LVQPGGSLRL TCAAS                                           25

SEQ ID NO: 101          moltype = AA   length = 25
FEATURE                 Location/Qualifiers
source                  1..25
                        mol_type = protein
                        organism = synthetic construct
SEQUENCE: 101
QVQLVESGAE LVQPSESLRL TCVAS                                           25

SEQ ID NO: 102          moltype = AA   length = 25
FEATURE                 Location/Qualifiers
source                  1..25
                        mol_type = protein
                        organism = synthetic construct
SEQUENCE: 102
QVQLVESGGE LVQPSESLRL TCVAS                                           25

SEQ ID NO: 103          moltype = AA   length = 25
FEATURE                 Location/Qualifiers
source                  1..25
                        mol_type = protein
                        organism = synthetic construct
SEQUENCE: 103
QVQLVESGAE LVQPGESLRL TCVAS                                           25

SEQ ID NO: 104          moltype = AA   length = 25
FEATURE                 Location/Qualifiers
source                  1..25
                        mol_type = protein
                        organism = synthetic construct
SEQUENCE: 104
QVQLVESGAE LVQPSGSLRL TCVAS                                           25

SEQ ID NO: 105          moltype = AA   length = 25
FEATURE                 Location/Qualifiers
source                  1..25
                        mol_type = protein
                        organism = synthetic construct
SEQUENCE: 105
QVQLVESGGE LVQPGESLRL TCVAS                                           25

SEQ ID NO: 106          moltype = AA   length = 25
FEATURE                 Location/Qualifiers
source                  1..25
                        mol_type = protein
                        organism = synthetic construct
SEQUENCE: 106
QVQLVESGGE LVQPSGSLRL TCVAS                                           25

SEQ ID NO: 107          moltype = AA   length = 25
FEATURE                 Location/Qualifiers
source                  1..25
                        mol_type = protein
                        organism = synthetic construct
SEQUENCE: 107
QVQLVESGGE LVQPGGSLRL TCVAS                                           25

SEQ ID NO: 108          moltype = AA   length = 25
FEATURE                 Location/Qualifiers
source                  1..25
                        mol_type = protein
                        organism = synthetic construct
SEQUENCE: 108
QVQLMESGAE LVQPSESLRL TCVAS                                           25

SEQ ID NO: 109          moltype = AA   length = 25
FEATURE                 Location/Qualifiers
source                  1..25
```

```
                        mol_type = protein
                        organism = synthetic construct
SEQUENCE: 109
QVQLMESGGE LVQPSESLRL TCVAS                                              25

SEQ ID NO: 110          moltype = AA  length = 25
FEATURE                 Location/Qualifiers
source                  1..25
                        mol_type = protein
                        organism = synthetic construct
SEQUENCE: 110
QVQLMESGAE LVQPGESLRL TCVAS                                              25

SEQ ID NO: 111          moltype = AA  length = 25
FEATURE                 Location/Qualifiers
source                  1..25
                        mol_type = protein
                        organism = synthetic construct
SEQUENCE: 111
QVQLMESGAE LVQPSGSLRL TCVAS                                              25

SEQ ID NO: 112          moltype = AA  length = 25
FEATURE                 Location/Qualifiers
source                  1..25
                        mol_type = protein
                        organism = synthetic construct
SEQUENCE: 112
QVQLMESGGE LVQPGESLRL TCVAS                                              25

SEQ ID NO: 113          moltype = AA  length = 25
FEATURE                 Location/Qualifiers
source                  1..25
                        mol_type = protein
                        organism = synthetic construct
SEQUENCE: 113
QVQLMESGGE LVQPSGSLRL TCVAS                                              25

SEQ ID NO: 114          moltype = AA  length = 25
FEATURE                 Location/Qualifiers
source                  1..25
                        mol_type = protein
                        organism = synthetic construct
SEQUENCE: 114
QVQLMESGGE LVQPGGSLRL TCVAS                                              25

SEQ ID NO: 115          moltype = AA  length = 25
FEATURE                 Location/Qualifiers
source                  1..25
                        mol_type = protein
                        organism = synthetic construct
SEQUENCE: 115
QVQLVESGAE LVQPSESLRL TCAAS                                              25

SEQ ID NO: 116          moltype = AA  length = 25
FEATURE                 Location/Qualifiers
source                  1..25
                        mol_type = protein
                        organism = synthetic construct
SEQUENCE: 116
QVQLVESGGE LVQPSESLRL TCAAS                                              25

SEQ ID NO: 117          moltype = AA  length = 25
FEATURE                 Location/Qualifiers
source                  1..25
                        mol_type = protein
                        organism = synthetic construct
SEQUENCE: 117
QVQLVESGAE LVQPSGSLRL TCAAS                                              25

SEQ ID NO: 118          moltype = AA  length = 25
FEATURE                 Location/Qualifiers
source                  1..25
                        mol_type = protein
                        organism = synthetic construct
SEQUENCE: 118
QVQLVESGAE LVQPSGSLRL TCAAS                                              25

SEQ ID NO: 119          moltype = AA  length = 25
FEATURE                 Location/Qualifiers
```

```
source                        1..25
                              mol_type = protein
                              organism = synthetic construct
SEQUENCE: 119
QVQLVESGGE LVQPSGSLRL TCAAS                                              25

SEQ ID NO: 120                moltype = AA  length = 25
FEATURE                       Location/Qualifiers
source                        1..25
                              mol_type = protein
                              organism = synthetic construct
SEQUENCE: 120
QVQLVESGGE LVQPGGSLRL TCAAS                                              25

SEQ ID NO: 121                moltype = AA  length = 25
FEATURE                       Location/Qualifiers
source                        1..25
                              mol_type = protein
                              organism = synthetic construct
SEQUENCE: 121
QVQLMESGAE LVQPSESLRL TCAAS                                              25

SEQ ID NO: 122                moltype = AA  length = 25
FEATURE                       Location/Qualifiers
source                        1..25
                              mol_type = protein
                              organism = synthetic construct
SEQUENCE: 122
QVQLMESGGE LVQPSESLRL TCAAS                                              25

SEQ ID NO: 123                moltype = AA  length = 25
FEATURE                       Location/Qualifiers
source                        1..25
                              mol_type = protein
                              organism = synthetic construct
SEQUENCE: 123
QVQLMESGAE LVQPGESLRL TCAAS                                              25

SEQ ID NO: 124                moltype = AA  length = 25
FEATURE                       Location/Qualifiers
source                        1..25
                              mol_type = protein
                              organism = synthetic construct
SEQUENCE: 124
QVQLMESGAE LVQPSGSLRL TCAAS                                              25

SEQ ID NO: 125                moltype = AA  length = 25
FEATURE                       Location/Qualifiers
source                        1..25
                              mol_type = protein
                              organism = synthetic construct
SEQUENCE: 125
QVQLMESGGE LVQPGESLRL TCAAS                                              25

SEQ ID NO: 126                moltype = AA  length = 25
FEATURE                       Location/Qualifiers
source                        1..25
                              mol_type = protein
                              organism = synthetic construct
SEQUENCE: 126
QVQLMESGGE LVQPSGSLRL TCAAS                                              25

SEQ ID NO: 127                moltype = AA  length = 25
FEATURE                       Location/Qualifiers
source                        1..25
                              mol_type = protein
                              organism = synthetic construct
SEQUENCE: 127
QVQLMESGGE LVQPGGSLRL TCAAS                                              25

SEQ ID NO: 128                moltype = AA  length = 107
FEATURE                       Location/Qualifiers
source                        1..107
                              mol_type = protein
                              organism = synthetic construct
SEQUENCE: 128
DIEMTQSPLS LSATPGETVS ISCRASEDIY NALAWYLQKP GRSPRLLIYN TDTLHTGVPD         60
RFSGSGSGTD FTLKISRVQT EDVGVYFCQH YFHYPRTFGQ GTKLELK                     107
```

| SEQ ID NO: 129 | moltype = AA length = 23 |
| --- | --- |
| FEATURE | Location/Qualifiers |
| source | 1..23 |
| | mol_type = protein |
| | organism = synthetic construct |

SEQUENCE: 129
```
DIEMTQSPLS LSATPGETVS ISC                                             23
```

| SEQ ID NO: 130 | moltype = AA length = 237 |
| --- | --- |
| FEATURE | Location/Qualifiers |
| source | 1..237 |
| | mol_type = protein |
| | organism = synthetic construct |

SEQUENCE: 130
```
MSVPTQVLGL LLLWLTDARC DIEMTQSPLS LSATPGETVS ISCRASEDIY NALAWYLQKP      60
GRSPRLLIYN TDTLHTGVPD RFSGSGSGTD FTLKISRVQT EDVGVYFCQH YFHYPRTFGQ     120
GTKLELKRSD AQPSVFLFQP SLDELHTGSA SIVCILNDFY PKEVNVKWKV DGVVQNKGIQ     180
ESTTEQNSKD STYSLSSTLT MSSTEYQSHE KFSCEVTHKS LASTLVKSFN RSECQRE       237
```

| SEQ ID NO: 131 | moltype = AA length = 122 |
| --- | --- |
| FEATURE | Location/Qualifiers |
| source | 1..122 |
| | mol_type = protein |
| | organism = synthetic construct |

SEQUENCE: 131
```
EVTLQESGPG LVKPSQTLSL TCVVSGFSLT NNNVNWVRQR PGRGLEWMGG VWAGGATDYN      60
SAVKSRISIT RDTAKNQVSL QLSSMTTEDT AVYYCARDGG YSSSTLYAMD AWGQGTLVTV     120
SS                                                                   122
```

| SEQ ID NO: 132 | moltype = AA length = 107 |
| --- | --- |
| FEATURE | Location/Qualifiers |
| source | 1..107 |
| | mol_type = protein |
| | organism = synthetic construct |

SEQUENCE: 132
```
EIVMTQSPAS LSLSQEEKVT ITCRASEDIY NALAWYQQKP GQAPKLLIYN TDTLHTGVPS      60
RFSGSGSGTD YSFTISSLEP EDVAVYFCQH YFHYPRTFGA GTKVELK                  107
```

| SEQ ID NO: 133 | moltype = DNA length = 1359 |
| --- | --- |
| FEATURE | Location/Qualifiers |
| source | 1..1359 |
| | mol_type = other DNA |
| | organism = Canis lupus familiaris |

SEQUENCE: 133
```
gaagtgaccc tgcaagagtc tggccctggc ctggttaagc ctagccagac actgagcctg      60
acctgtgtgt gtccggcttt cagcctgacc aacaacaacg tgaactgggt ccgacagagg     120
cctggcagag gactggaatg gatggcggca gtttgggctg gcggagccac cgattacaac     180
agcgccgtga agtcccggat cagcatcacc agagacaccg ccaagaacca ggtgtccctg     240
cagctgagca gcatgaccac agaggatacc gccgtgtact actgcgccag agatggcggc     300
tacagcagca gcacactgta cgccatggat gcctggggac agggcacact ggttacagtg     360
tctagcggcc gcacaacagc ccctagcgtt ttccctctgg ctccatcttg tggcagcacc     420
agcggatcta cagtgctcct ggcttgtctg gtgtcaggct acttccctga gcctgtgacc     480
gtgtcctgga atagcggctc tctgacaagc ggcgtgcaca catttccaag cgtgctgcag     540
tctagcggcc tgcactctct gtccagcatg gtcacagtgc ccagcagcag atggcccagc     600
gagacattca cctgtaacgt ggtgcacccc gccagcaaca caaggtgga caagcccgtg      660
ttcaacgagt gcagatgcac cgacacacct ccatgtcctg tgcctgaacc tctcggcgga     720
cctagcgtgc tgatcttccc acctaagcct aaggacatcc tgcggatcac ccggacacct     780
gaagtgacat cgctggtgct ggatctgggc agagaagatc ccgaggtgca gatcagttgg     840
ttcgtggacg gcaaagaggt gcacaccgct aagacccaga gcagagagca gcagttcaac     900
ggcacctaca gagtggtgtc tgtgctgccc atcgagcacc aggattggct gaccggcaaa     960
gaattcaagt gccgcgtgaa ccacatcgac ctgcccttct caatcgagcg gaccatcagc    1020
aaggccagag cagagcccca aagccttcc gtgtatgtcc tgcctccatc tcctaaagag     1080
ctgtccagct ccgacaccgt gtccatcacc tgtctgatca aggacttcta ccctcctgac    1140
atcgacgtgg aatggcagag caacggccag caagagcccg agagaaagca cagaatgacc    1200
cctccacagc tggacgagga cggcagctac ttcctgtaca gcaagctgag cgtggacaag    1260
agccgatggc agcagggcga tcctttttacc tgtgccgtga tgcacgagac actgcagaac    1320
cactacaccg atctgtccct gtctcacagc ccggctga                           1359
```

| SEQ ID NO: 134 | moltype = DNA length = 654 |
| --- | --- |
| FEATURE | Location/Qualifiers |
| source | 1..654 |
| | mol_type = other DNA |
| | organism = Canis lupus familiaris |

SEQUENCE: 134
```
gagatcgtga tgacacagtc tccagccagc ctgagcctgt ctcaagagga aaaagtgacc      60
atcacctgtc gggccagcga ggacatctat aatgcccttgg cctggtatca gcagaagccc    120
ggacaagccc ctaagctgct gatctacaac accgacacac tgcacaccgg cgtgcccagc    180
agattttctg gctctggcag cggcaccgac tacagcttta caatcagcag cctggaacct    240
gaggacgtgg ccgtgtactt ctgccagcac tactttcact accccagaac cttcggagcc    300
```

```
ggcaccaagg tggaactgaa gagaaacgat gcccagcctg ccgtgtacct gttccagcct    360
tctccagatc agctgcacac aggctctgcc agcgttgtgt gcctgctgaa cagcttctac    420
cccaaggaca tcaacgtgaa gtggaaggtg gacggcgtga tccaggacac cggcatccaa    480
gagtctgtga ccgagcagga caaggacagc acctacagcc tgtctagcac cctgaccatg    540
agcagcaccg agtacctgag ccacgagctg tactcttgcg agatcaccca aagagcctg     600
ccaagcacac tgatcaagag cttccagcgg agcgagtgcc agagagtgga ttga           654

SEQ ID NO: 135           moltype = DNA    length = 1359
FEATURE                  Location/Qualifiers
source                   1..1359
                         mol_type = other DNA
                         organism = Canis lupus familiaris
SEQUENCE: 135
gaagtgaccc tgcaagagtc tggccctggc ctggttaagc cctctcagac cctgtctctg    60
acctgcgtgg tgtccggctt ctccctgacc aacaacaacg tgaactgggt ccgacagagg   120
cctggcagag gactgaatg gatgggcgga gtttgggctg cggcgctac cgattacaac    180
tccgccgtga agtcccggat cagcatcacc agagacaccg ccaagaacca ggtgtccctg   240
cagctgtcct ctatgaccac cgaggatacc gccgtgtact actgcgctag agatggcggc   300
tactccagct ctaccctgta cgccatggat gcttggggcc agggaacact ggtcaccgtg   360
tcctccgctt ctaccaccgc tccatctgtg ttccctctgg ctccttcttg cggctctacc   420
tccggatcta cagtggctct ggcctgtctg gtgtctggct actttcctga gcctgtgacc   480
gtgtcttgga actccggctc tctgacatcc ggcgtgcaca ccttccatc cgtgctgcag   540
tctagcggcc tgcactctct gagttctatg gttaccgtgc cttccagccg gtggccttcc   600
gagacattca cctgtaacgt ggtgcacccc gcctccaaca ccaaggtgga caagcctgtg   660
ttcaacgagt gcagatgcac cgacacacct ccatgtcctg tgcctgaacc tctcggcgga   720
ccttccgtgc tgatcttccc acctaagcct aaggacatcc tcggatcac cggacacct    780
gaagtgacat gtgtggtgct ggacctgggc cgagaggatc ctgaagtgca gatcagttgg   840
ttcgtggacg gcaaagaggt gcacaccgct aagacccagt ccagagagca gcagttcaac   900
ggcacctaca gagtggtgtc tgtgctgccc atcgagcacc aggattggct gaccggcaaa   960
gaattcaagt gccgcgtgaa ccacatcgac ctgccttctc caatcgagag gaccatctcc  1020
aaggctagag gcagagccca caagccttcc gtgtatgtcc tgcctccatc tcctaaagag  1080
ctgtccagct ccgacaccgt gtctatcacc tgtctgatca aggacttcta ccctcctgac  1140
atcgacgtga atggcagtc caacggccag caagagcccg agaaagca cagaatgacc  1200
cctccacagc tggacgagga cggctcctac ttcctgtact ccaagctgtc cgtggacaag  1260
tccagatggc agcaaggcga ccctttcacc tgtgccgtga tgcacgagac actgcagaac  1320
cactacaccg atctgtccct gtctcactcc cctggctga                          1359

SEQ ID NO: 136           moltype = DNA    length = 654
FEATURE                  Location/Qualifiers
source                   1..654
                         mol_type = other DNA
                         organism = Canis lupus familiaris
SEQUENCE: 136
gagatcgtga tgacccagtc tcctgcctct ctgtccctga gccaagagga aaaagtgacc    60
atcacctgtc gggcctccga ggacatctac aatgcctgg cttggtatca gcagaagccc   120
ggccaggctc ctaagctgct gatctacaac accgacacac tgcacaccgg cgtgccctct   180
agattttccg gctctggctc tggcaccgac tacagcttta ccatctccag cctgaacct   240
gaggacgtgg ccgtgtactt ctgccagcac tactttcact accctcggac ctttggcgct   300
ggcaccaagg tggaactgaa gcggaatgat gcccagcctg ccgtgtacct gttccagcct   360
tctccagatc agctgcatac cggctctgcc tccgtcgtgt gtctgctgaa cagcttctac   420
cccaaggaca tcaacgtgaa gtggaaggtg gacggcgtga tccaggacac cggcatccaa   480
gagtctgtga ccgagcagga caaggactcc acctacagcc tgtctagcac cctgaccatg   540
tcctccaccg agtacctgag ccacgagctg tactcttgcg agatcaccca caagtccctg   600
ccttccacac tgatcaagtc cttccagcgg agcgagtgcc agagagtgga ttga          654

SEQ ID NO: 137           moltype = DNA    length = 1359
FEATURE                  Location/Qualifiers
source                   1..1359
                         mol_type = other DNA
                         organism = Canis lupus familiaris
SEQUENCE: 137
gaagtgaccc tgcaagagtc tggccctggc ctggtcaaac cttctcagac cctgagcctg    60
acctgcgtgg tgtctggatt cagcctgacc aacaacaacg tgaactgggt ccgacagagg   120
cctggcagag gactggaatg gatgggcgga gtttgggctg gcggagccac cgattacaac   180
agcgccgtga agtccaggat cagcatcacc agagacaccg ccaagaacca ggtgtccctg   240
cagctgtcta gcatgaccac cgaagatacc gccgtgtact actgcgccag agatggcggc   300
tacagcagct ctaccctgta cgccatggat gcctggggac agggaacact ggtcacagtg   360
tctgcgcca gcacaacagc ccctagcgtt ttccctctgg ctccttcttg cggctctacc   420
tctggatcta cagtggctct ggcctgtctg gtgtccgcat actttcctga acctgtgacc   480
gtgtcctgga acagcggctc tctgacatct ggcgtgcaca cattcccag cgtgctgcag   540
tctagcggcc tgcactctct gagcagcatg gtcaccgtgc ctagcagcag atggcccagc   600
gaaaccttca cctgtaacgt ggtgcacccc gccagcaaca ccaaggtgga caagcctgtg   660
ttcaacgagt gcagatgcac cgacacacct ccatgtcctg tgcctgaacc tctcggcgga   720
ccttccgtgc tgatcttccc acctaagcct aaggacatca caggatcac cggacacct    780
gaagtgacat gtgtggtgct ggacctgggc agagaagatc ccgaggtgca gatcagttgg   840
ttcgtggacg gcaaagaggt gcacaccgct aagacccaga gcagagagca gcagttcaac   900
ggcacctaca gagtggtgtc cgtgctgcct atcgagcacc aggattggct gaccggcaaa   960
gaattcaagt gccgcgtgaa ccacatcgac ctgccttctc caatcgagag gaccatcagc  1020
aaggccagag caggcccca aaacctagt gtgtatgtgc tgcctccatc tcctaaagag    1080
```

```
ctgagcagct ccgacaccgt gtccatcacc tgtctgatca aggacttcta ccctcctgac 1140
atcgacgtgg aatggcagag caacggccag caagagcccg agagaaagca caggatgacc 1200
cctccacagc tggacgagga cggcagctac ttcctgtaca gcaagctgag cgtggacaag 1260
agccgatggc agcagggcga tccttttacc tgtgccgtga tgcacgaaac cctgcagaac 1320
cactacaccg acctgtctct gagccactct cctggctga                        1359

SEQ ID NO: 138        moltype = DNA  length = 654
FEATURE               Location/Qualifiers
source                1..654
                      mol_type = other DNA
                      organism = Canis lupus familiaris
SEQUENCE: 138
gagatcgtga tgacccagtc tcctgccagc ctgagcctgt ctcaagagga aaaagtgacc  60
atcacctgta gggccagcga ggacatctac aatgccctgg cctggtatca gcagaagcct 120
ggacaggccc ctaagctgct gatctacaac accgacacac tgcacaccgg cgtgccctct 180
agattcagcg gatctggctc tggcaccgac tacagcttta caatcagcag cctggaacct 240
gaggacgtgg ccgtgtactt ctgccagcac tactttcact accccagaac cttcggagcc 300
ggcaccaagg tggaactgaa gaggaatgat gcccagcctg ccgtgtacct gttccagcct 360
tctccagatc agctgcacac aggctctgcc agcgttgtgt gcctgctgaa cagcttctac 420
cccaaggaca tcaacgtgaa gtggaaggtg gacggcgtga tccaggacac cggcatccaa 480
gagtctgtga ccgagcagga caaggacagc acctacagcc tgtctagcac cctgaccatg 540
agcagcaccg agtacctgag ccacgagctg tactcttgcg agatcaccca caagagcctg 600
ccttccacac tgatcaagag cttccagcgg agcgagtgcc agagagtgga ttga       654
```